(12) United States Patent
Denker et al.

(10) Patent No.: US 11,081,652 B2
(45) Date of Patent: Aug. 3, 2021

(54) ORGANIC LIGHT-EMITTING DIODE COMPRISING DIFFERENT MATRIX COMPOUNDS IN THE FIRST AND SECOND ELECTRON TRANSPORT LAYER

(71) Applicant: Novaled GmbH, Dresden (DE)

(72) Inventors: Ulrich Denker, Dresden (DE); Mike Zöllner, Dresden (DE); Katja Gräf, Dresden (DE); Volodymyr Senkovskyy, Dresden (DE); Bodo Wallikewitz, Dresden (DE); Johannes Scholz, Dohna (DE); Julien Frey, Dresden (DE)

(73) Assignee: Novaled GmbH, Dresden (DE)

( * ) Notice: Subject to any disclaimer, the term of this patent is extended or adjusted under 35 U.S.C. 154(b) by 462 days.

(21) Appl. No.: 15/572,336

(22) PCT Filed: May 11, 2016

(86) PCT No.: PCT/EP2016/060582
§ 371 (c)(1),
(2) Date: Nov. 7, 2017

(87) PCT Pub. No.: WO2016/180891
PCT Pub. Date: Nov. 17, 2016

(65) Prior Publication Data
US 2018/0145263 A1    May 24, 2018

(30) Foreign Application Priority Data

May 12, 2015   (EP) .................................... 15162788

(51) Int. Cl.
*H01L 51/00* (2006.01)
*C07D 401/14* (2006.01)
(Continued)

(52) U.S. Cl.
CPC ........ *H01L 51/0072* (2013.01); *C07D 401/04* (2013.01); *C07D 401/14* (2013.01);
(Continued)

(58) Field of Classification Search
CPC .. C07D 401/04; C07D 401/14; C07D 405/14; C09K 2211/1007; C09K 2211/1029;
(Continued)

(56) References Cited

U.S. PATENT DOCUMENTS

| 2010/0039027 A1 | 2/2010 | Takashima et al. |
| 2010/0193773 A1* | 8/2010 | Yamamoto ........... C07D 235/18 257/40 |

(Continued)

FOREIGN PATENT DOCUMENTS

| EP | 2372803 A1 | 10/2011 |
| EP | 2700695 A1 | 2/2014 |

(Continued)

OTHER PUBLICATIONS

PCT International Search Report and Written Opinion for PCT Application No. PCT/EP2016/060582 dated Jun. 23, 2016 (14 pages).

(Continued)

*Primary Examiner* — Dawn L Garrett
(74) *Attorney, Agent, or Firm* — Eversheds Sutherland (US) LLP

(57) ABSTRACT

The present invention is directed to matrix compounds and an organic light-emitting diode (OLED) comprising an emission layer and an electron transport layer stack of at least two electron transport layers, wherein a first electron transport layer and a second electron transport layer comprises at least one matrix compound, wherein the matrix compound or compounds of the first electron transport layer (Continued)

is/are different to the matrix compound or compounds of the second electron transport layer; and in addition, the first electron transport layer comprises a dopant of a lithium halide and/or lithium organic complex; and the second electron transport layer is free of a dopant; wherein at least one matrix compound of the second electron transport layer having the chemical formula Ia, Ib and/or Ic: (Ia) (Ib) (Ic) wherein Ar=substituted or unsubstituted arylene with 6 to 20 ring-forming carbon atoms; or carbazolylene; ET=substituted or unsubstituted aryl group with 13 to 40 ring-forming carbon atoms; or a substituted or unsubstituted heteroaryl group with 14 to 40 ring-forming atoms.

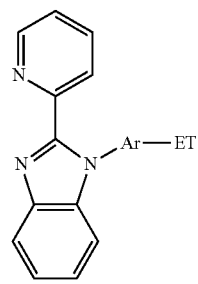

(Ia)

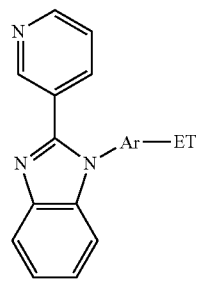

(Ib)

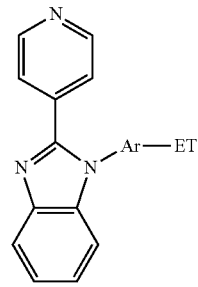

(Ic)

17 Claims, 3 Drawing Sheets

(51) Int. Cl.
*C07D 405/14* (2006.01)
*C07D 401/04* (2006.01)
*H01L 51/50* (2006.01)
*H01L 51/56* (2006.01)

(52) U.S. Cl.
CPC ........ *C07D 405/14* (2013.01); *H01L 51/0052* (2013.01); *H01L 51/0054* (2013.01); *H01L 51/0058* (2013.01); *H01L 51/0067* (2013.01); *H01L 51/0073* (2013.01); *H01L 51/0077* (2013.01); *C09K 2211/1007* (2013.01); *C09K 2211/1029* (2013.01); *C09K 2211/185* (2013.01); *H01L 51/001* (2013.01); *H01L 51/0003* (2013.01); *H01L 51/508* (2013.01); *H01L 51/5076* (2013.01); *H01L 51/56* (2013.01); *H01L 2251/301* (2013.01)

(58) Field of Classification Search
CPC ........ C09K 2211/185; H01L 2251/301; H01L 51/0003; H01L 51/001; H01L 51/0052; H01L 51/0054; H01L 51/0058; H01L 51/0067; H01L 51/0072; H01L 51/0073; H01L 51/0077; H01L 51/5076; H01L 51/508; H01L 51/56
See application file for complete search history.

(56) References Cited

U.S. PATENT DOCUMENTS

| | | | |
|---|---|---|---|
| 2014/0103306 A1 | 4/2014 | Moon et al. | |
| 2015/0329772 A1* | 11/2015 | Heil | C09K 11/025 252/500 |
| 2018/0261784 A1* | 9/2018 | Wallikewitz | H01L 51/5096 |

FOREIGN PATENT DOCUMENTS

| | | | |
|---|---|---|---|
| EP | 2 790 236 A1 * | 10/2014 | |
| JP | 2007049055 A | 2/2007 | |
| KR | 20140012920 A | 2/2014 | |
| KR | 20140141337 A | 12/2014 | |
| WO | 2013/009095 A1 | 1/2013 | |

OTHER PUBLICATIONS

Shan et al., "Enhancing the Luminescence Properties and Stability of Cationic Iridium(III) Complexes Based on Phenylbenzoimidazole Ligand: A Combined Experimental and Theoretical Study," Dalton Trans., 2013, 42:11056-11065.
Sun et al., "TD-DFT and LDM Studies of the Electronic Spectrum Properties of 2-(2'pyridyl)benzimidazole Derivatives and Their Related Complexes," Journal of Molecular Structure, 2010, 995:(1-3)7-13.
Wang et al., Ru—Pt and Ru—Pd Heterobimetallic Complexes Based on a New Ligand with Two Distinct Chelate Sites, Dalton Trans., 2012, 41(18):5553-5554.
Wu et al., "Ruthenium (II) Polypyridyl Complexes Based on Bipyridine and Two Novel Diimine Ligands with Carrier-Transporting Unit: Synthesis, Photoluminescence and Redox Properties," Journal of Organometallic Chemistry, 2010, 695(17):2048-2056.

* cited by examiner

ORGANIC LIGHT-EMITTING DIODE COMPRISING DIFFERENT MATRIX COMPOUNDS IN THE FIRST AND SECOND ELECTRON TRANSPORT LAYER

CROSS REFERENCE TO RELATED APPLICATIONS

This application is a U.S. national stage application of PCT/EP2016/060582, filed May 11, 2016, which claims priority to European Application No. 15162788.2, filed May 12, 2015. The contents of these applications are hereby incorporated by reference.

The present invention relates to an organic light-emitting diode containing electron transport layers with different matrix compounds in the first and second electron transport layer and a method of manufacturing the same.

DESCRIPTION OF THE RELATED ART

Organic light-emitting diodes (OLEDs), which are self-emitting devices, have a wide viewing angle, excellent contrast, quick response, high brightness, excellent driving voltage characteristics, and color reproduction. A typical OLED includes an anode, a hole transport layer (HTL), an emission layer (EML), an electron transport layer (ETL), and a cathode, which are sequentially stacked on a substrate. In this regard, the HTL, the EML, and the ETL are thin films formed from organic and/or organometallic compounds.

When a voltage is applied to the anode and the cathode, holes injected from the anode move to the EML, via the HTL, and electrons injected from the cathode move to the EML, via the ETL. The holes and electrons recombine in the EML to generate excitons. When the excitons drop from an excited state to a ground state, light is emitted. The injection and flow of holes and electrons should be balanced, so that an OLED having the above-described structure has excellent efficiency. However, there is a continuously need to improve the conductivity and to reduce the voltage to operate an OLED more efficiently.

SUMMARY

It is one object to provide an organic light-emitting diode with a reduced low voltage to efficiently operate an OLED, especially for blue emitting OLEDs but also, for example, for red, green or white emitting OLEDs, in particular for top and/or bottom emission organic light-emitting diodes (OLED).

According to one aspect, there is provided an organic light-emitting diode (OLED) comprising an emission layer and an electron transport layer stack of at least two electron transport layers, wherein a first electron transport layer and a second electron transport layer comprises at least one matrix compound, wherein
   the matrix compound or compounds of the first electron transport layer is/are different to the matrix compound or compounds of the second electron transport layer; and in addition,
   the first electron transport layer comprises a dopant of a lithium halide and/or lithium organic complex; and
   the second electron transport layer is free of a dopant; wherein
   at least one matrix compound of the second electron transport layer having the chemical formula Ia, Ib and/or Ic;

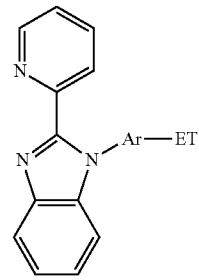
(Ia)

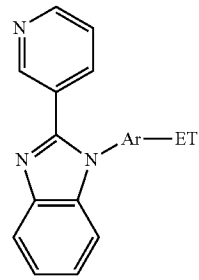
(Ib)

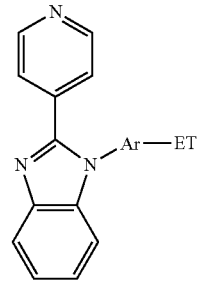
(Ic)

wherein
Ar=substituted or unsubstituted arylene with 6 to 20 ring-forming carbon atoms; or carbazolylene;
ET=substituted or unsubstituted aryl group with 13 to 40 ring-forming carbon atoms; or a substituted or unsubstituted heteroaryl group with 14 to 40 ring-forming atoms.
  The pyridinyl moiety can be bonded to the 2-position in benzimidazole in such a way, that the nitrogen atom is in 2'-, 3'-, or 4'-position:

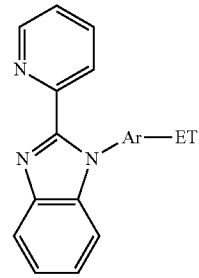
(Ia)

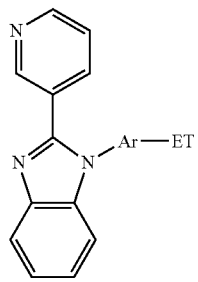

(Ib)

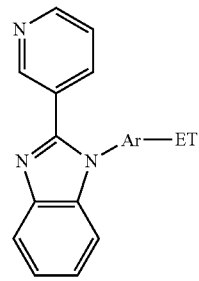

(Ib)

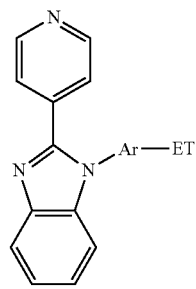

(Ic)

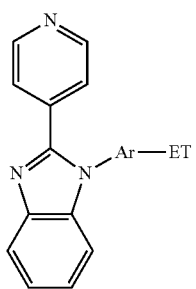

(Ic)

According to another aspect, there is provided an organic light-emitting diode (OLED) comprising an emission layer and an electron transport layer stack of at least two electron transport layers, wherein a first electron transport layer and a second electron transport layer comprises at least one matrix compound, wherein the matrix compound or compounds of the first electron transport layer is/are a phosphine oxide compound substituted with aryl, heteroaryl or alkyl groups and different to the matrix compound or compounds of the second electron transport layer; and in addition, the first electron transport layer comprises a dopant of a lithium halide and/or lithium organic complex; and the second electron transport layer is free of a dopant; wherein at least one matrix compound of the second electron transport layer having the chemical formula Ia, Ib and/or Ic;

wherein

Ar=substituted or unsubstituted arylene with 6 to 20 ring-forming carbon atoms; or carbazolylene;

ET=substituted or unsubstituted aryl group with 13 to 40 ring-forming carbon atoms; or a substituted or unsubstituted heteroaryl group with 14 to 40 ring-forming atoms.

According to another aspect, there is provided an organic light-emitting diode (OLED) comprising an emission layer and an electron transport layer stack of at least two electron transport layers, wherein a first electron transport layer and a second electron transport layer comprises at least one matrix compound, wherein oxide compound substituted with aryl, heteroaryl or alkyl groups and different to the the matrix compound or compounds of the first electron transport layer is/are a phospine oxide compound substituted with aryl, heteroaryl or alkyl groups and different to the matrix compound or compounds of the second electron transport layer; and in addition, the first electron transport layer comprises a dopant of a lithium halide and/or lithium organic complex; and the second electron transport layer is free of a dopant; wherein at least one matrix compound of the second electron transport layer having the chemical formula Ia, Ib and/or Ic;

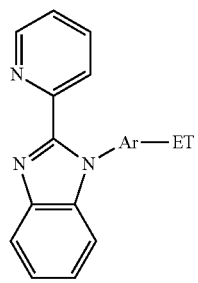

(Ia)

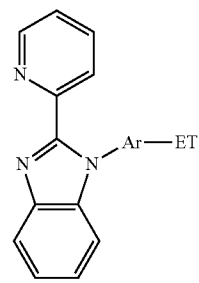

(Ia)

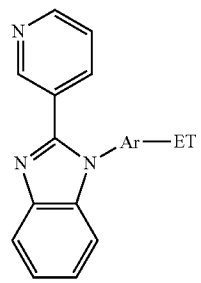

(Ib)

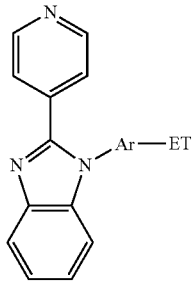

(Ic)

wherein

Ar=substituted or unsubstituted arylene with 6 to 20 ring-forming carbon atoms, preferably 6 to 18 ring-forming carbon atoms, and more preferred 6 to 13 ring-forming carbon atoms;

ET=a substituted or unsubstituted heteroaryl group with 20 to 24 ring-forming atoms.

According to another aspect, there is provided an organic light-emitting diode (OLED) comprising an emission layer and an electron transport layer stack of at least two electron transport layers, wherein a first electron transport layer and a second electron transport layer comprises at least one matrix compound, wherein the matrix compound or compounds of the first electron transport layer is/are selected from:

(3-(dibenzo[c,h]acridin-7-yl)phenyl)diphenylphosphine oxide, 3-phenyl-3H-benzo[b]dinaphtho[2,1-d: 1',2'-f]phosphepine-3-oxide, phenyldi(pyren-1-yl) phosphine oxide, bis(4-(anthracen-9-yl)phenyl) (phenyl)phosphine oxide, (3-(9,10-di(naphthalen-2-yl)anthracen-2-yl)phenyl)diphenylphosphine oxide, phenyldi(pyren-1-yl)phosphine oxide, diphenyl(5-(pyren-1-yl)pyridin-2-yl)phosphine oxide, diphenyl (4'-(pyren-1-yl)-[1,1'-biphenyl]-3-yl)phosphine oxide, diphenyl(4'-(pyren-1-yl)-[1,1'-biphenyl]-3-yl) phosphine oxide, (3'-(dibenzo[c,h]acridin-7-yl)-[1, 1'-biphenyl]-4-yl)diphenylphosphine oxide, (3-(10-(naphthalen-2-yl)anthracen-9-yl)phenyl)-diphenylphosphine oxide and/or phenyl bis(3-(pyren-1-yl)phenyl)phosphine oxide, and different to the matrix compound or compounds of the second electron transport layer; and in addition, the first electron transport layer comprises a dopant of a lithium halide and/or lithium organic complex; and the second electron transport layer is free of a dopant; wherein at least one matrix compound of the second electron transport layer having the chemical formula Ia, Ib and/or Ic;

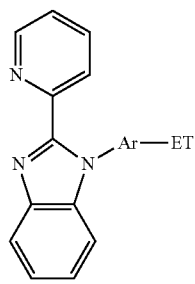

(Ia)

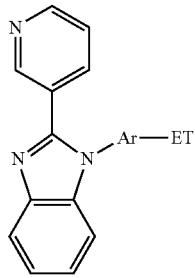

(Ib)

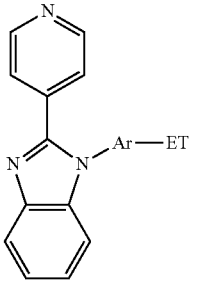

(Ic)

wherein

Ar=substituted or unsubstituted arylene with 6 to 20 ring-forming carbon atoms, preferably 6 to 18 ring-forming carbon atoms, and more preferred 6 to 13 ring-forming carbon atoms;

ET=substituted or unsubstituted aryl group with 13 to 40 ring-forming carbon atoms; or a substituted or unsubstituted heteroaryl group with 14 to 40 ring-forming atoms, preferably with 20 to 24 ring-forming atoms.

According to another aspect, there is provided an organic light-emitting diode (OLED) comprising an emission layer and an electron transport layer stack of at least two electron transport layers, wherein a first electron transport layer and a second electron transport layer comprises at least one matrix compound, wherein the matrix compound or compounds of the first electron transport layer is/are selected from:

(3-(dibenzo[c,h]acridin-7-yl)phenyl)diphenylphosphine oxide, 3-phenyl-3H-benzo[b]dinaphtho[2,1-d: 1'2'-f]phosphepine-3-oxide, phenyldi(pyren-1-yl) phosphine oxide, bis(4-(anthracen-9-yl)phenyl) (phenyl)phosphine oxide, (3-(9,10-di(naphthalen-2-yl)anthracen-2-yl)phenyl)diphenylphosphine oxide, phenyldi(pyren-1-yl)phosphine oxide, diphenyl(5-(pyren-1-yl)pyridin-2-yl)phosphine oxide, diphenyl (4'-(pyren-1-yl)-[1,1'-biphenyl]-3-yl)phosphine oxide, diphenyl(4'-(pyren-1-yl)[1,1'-biphenyl]-3-yl) phosphine oxide, (3'-(dibenzo[c,h]acridin-7-yl)-[1, 1'-biphenyl]-4-yl)diphenylphosphine oxide, (3-(10-(naphthalen-2-yl)anthracen-9-yl)phenyl)- diphenylphosphine oxide and/or phenyl bis(3-(pyren-1-yl)phenyl)phosphine oxide, and different to the matrix compound or compounds of the second electron transport layer; and in addition, the first electron transport layer comprises a dopant of a lithium halide and/or lithium organic complex; and the second electron transport layer is free of a dopant; wherein at least one matrix compound of the second electron transport layer having the chemical formula Ia, Ib and/or Ic;

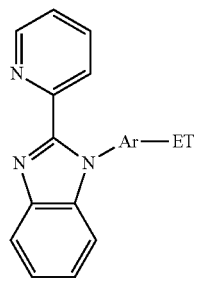

(Ia)

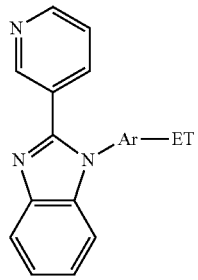

(Ib)

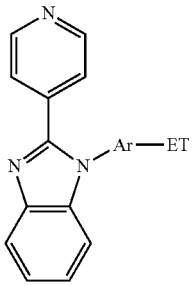

(Ic)

, wherein

Ar=substituted or unsubstituted arylene with 6 to 20 ring-forming carbon atoms, preferably 6 to 18 ring-forming carbon atoms, and more preferred 6 to 13 ring-forming carbon atoms;

ET=a substituted or unsubstituted heteroaryl group with 20 to 24 ring-forming atoms.

According to another aspect, there is provided an organic light-emitting diode (OLED) comprising an emission layer and an electron transport layer stack of at least two electron transport layers, wherein a first electron transport layer and a second electron transport layer comprises at least one matrix compound, wherein the matrix compound or compounds of the first electron transport layer is/are selected from:
(3-(dibenzo[c,h]acridin-7-yl)phenyl)diphenylphosphine oxide, 3-phenyl-3H-benzo[b]dinaphtho[2,1-d:1',2'-f]phosphepine-3-oxide, phenyldi(pyren-1-yl)phosphine oxide, bis(4-(anthracen-9-yl)phenyl)(phenyl)phosphine oxide, (3-(9,10-di(naphthalen-2-yl)anthracen-2-yl)phenyl)diphenylphosphine oxide, phenyldi(pyren-1-yl)phosphine oxide, diphenyl(5-(pyren-1-yl)pyridin-2-yl)phosphine oxide, diphenyl(4'-(pyren-1-yl)-[1,1'-biphenyl]-3-yl)phosphine oxide, diphenyl(4'-(pyren-1-yl)-[1,1'-biphenyl]-3-yl)phosphine oxide, (3'-(dibenzo[c,h]acridin-7-yl)-[1,1'-biphenyl]-4-yl)diphenylphosphine oxide, (3-(10-(naphthalen-2-yl)anthracen-9-yl)phenyl)-diphenylphosphine oxide and/or phenyl bis(3-(pyren-1-yl)phenyl)phosphine oxide, and different to the matrix compound or compounds of the second electron transport layer; and in addition, the first electron transport layer comprises a dopant of a lithium halide and/or lithium organic complex; and the second electron transport layer is free of a dopant; wherein at least one matrix compound of the second electron transport layer having the chemical formula Ia, Ib and/or Ic;

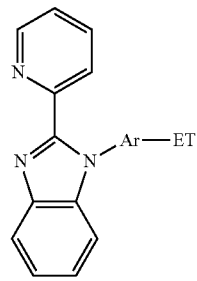

(Ia)

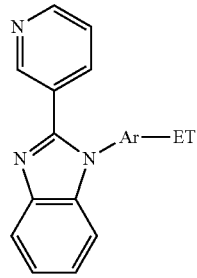

(Ib)

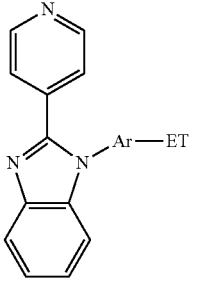

(Ic)

, wherein

Ar=unsubstituted arylene:
o-phenylene, m-phenylene, p-phenylene, biphenyl-2,2'-diyl, biphenyl-3,3'diyl, biphenyl-4,4'diyl, biphenyl-3,4'-diyl, p-terphenyl-4,4'-diyl, p-terphenyl-3,3'-diyl, p-terphenyl-2,2'-diyl, m-terphenyl-4,4'-diyl, m-terphenyl-3,3'-diyl, m-terphenyl-2,2'-diyl, o-terphenyl-4,4'-diyl, o-terphenyl-3,3'-diyl, o-terphenyl-2,2'-diyl; naphthalen-2,6-diyl, naphthalen-1,4-diyl; or substituted arylene or carbazolylene:
o-phenylene, m-phenylene, p-phenylene, biphenyl-2,2'-diyl, biphenyl-3,3'diyl, biphenyl-4,4'diyl, biphenyl-3,4'-diyl, fluoren-2,7-diyl, fluoren-3,6-diyl, carbazolen-3,6-diyl, carbazolen-2,7-diyl, p-terphenyl-4,4'-diyl, p-terphenyl-3,3'-diyl, p-terphenyl-2,2'-diyl, m-terphenyl-4,4'-diyl, m-terphenyl-3,3'-diyl, m-terphenyl-2,2'-diyl, o-terphenyl-4,4'-diyl, o-terphenyl-3,3'-diyl, o-terphenyl-2,2'-diyl; naphthalen-2,6-diyl, naphthalen-1,4-diyl; and wherein the substituent of the substituted arylene or carbazolylene is selected from the group of an alkyl group with 1 to 15 carbon atoms, preferably 1 to 12 carbon atoms, more preferred 1 to 4 carbon atoms; an alkoxy group with 1 to 15 carbon atoms, preferably 1 to 5 carbon atoms and more preferred 1 to 2 carbon atoms;

ET=-an unsubstituted aryl group with 13 to 40 ring-forming carbon atoms; or a unsubstituted heteroaryl group with 14 to 40 ring-forming atoms, preferably ET is selected from a group comprising anthrancen-2-yl, anthracen-9yl, pyren-1-yl, pyren-2-yl, phenanthren-9-yl, perylen-2-yl, perylen-3-yl, triphenylen-1-yl, triphenylen-2-yl, benzo[f]tetraphen-4-yl, benzo[e]pyren-4-yl, cyclopenta[cd]fluoranthen-6-yl, benzo[f]tetraphen-10-yl, benzo[e]pyren-3-yl, chrysene-1-yl, rubicen-5-yl, fluoranthen-3-yl, dibenzo[j,l]fluoranthen-3-yl, dibenzo[j,l]fluoranthen-9-yl, dibenzo[j,l]fluoranthen-10-yl, benzo[k]tetraphen-1-yl, benzo[k]tetraphen-3-yl, benzo[k]tetraphen-4-yl, benzo[k]tetraphen-7-yl, coronen-1-yl, dibenzo[ghi,mno]fluoranthen-1-yl, dinaptho[2,1-b:1',2'-d]furan-6-yl, acridin-9-yl, dibenzo[c,h]acridin-7-yl; or a substituted aryl group with 13 to 40 ring-forming carbon atoms; or a substituted heteroaryl group with 14 to 40 ring-forming atoms; preferably ET is selected from a group comprising anthrancen-2-yl, anthracen-9yl, pyren-1-yl, pyren-2-yl, phenanthren-9-yl, perylen-2-yl, perylen-3-yl, dinaptho[2,1-b:1',2'-d]furan-6-yl, acridin-9-yl, dibenzo[c,h]acridin-7-yl, fluoren-2-yl, fluoren-3-yl;

wherein the substituent of the substituted aryl group or heteroaryl group is selected from a group comprising phenyl, 1-naphthyl, 2-naphthyl, 2-biphenyl, 3-biphenyl, 4-biphenyl, 1-pyrenyl, 2-pyrenyl, 2-phenanthrenyl, 9,9'-fluorenyl or 9,9'-xanthenyl group.

According to one aspect, there is provided an organic light-emitting diode (OLED) comprising an emission layer and an electron transport layer stack of at least two electron transport layers, wherein a first electron transport layer and a second electron transport layer comprises at least one matrix compound, wherein the matrix compound or compounds of the first electron transport layer is/are different to the matrix compound or compounds of the second electron transport layer; and in addition, the first electron transport layer comprises a dopant of a lithium halide and/or lithium organic complex; and the second electron transport layer is free of a dopant; wherein at least one matrix compound of the second electron transport layer having the chemical formula Ia, Ib and/or Ic;

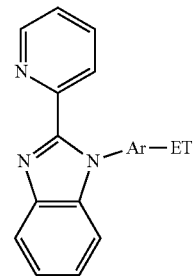

(Ia)

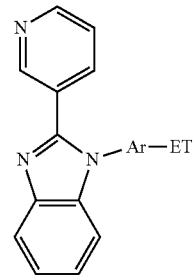

(Ib)

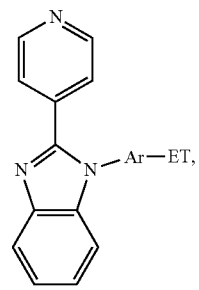

(Ic)

wherein

Ar=m-phenylene, biphenyl-2,2'-diyl, biphenyl-3,3'diyl, biphenyl-3,4'-diyl, fluoren-3,6-diyl, p-terphenyl-3,3'-diyl, m-terphenyl-4,4'-diyl, m-terphenyl-3,3'-diyl, m-terphenyl-2,2'-diyl, o-terphenyl-4,4'-diyl, o-terphenyl-3,3'-diyl, o-terphenyl-2,2'-diyl; or naphthalen-2,6-diyl; and ET=substituted or unsubstituted aryl group with 13 to 40 ring-forming carbon atoms; or a substituted or unsubstituted heteroaryl group with 14 to 40 ring-forming atoms, preferably a substituted or unsubstituted heteroaryl group with 20 to 24 ring-forming atoms.

According to one aspect, there is provided an organic light-emitting diode (OLED) comprising an emission layer and an electron transport layer stack of at least two electron transport layers, wherein a first electron transport layer and a second electron transport layer comprises at least one matrix compound, wherein the matrix compound or compounds of the first electron transport layer is/are different to the matrix compound or compounds of the second electron transport layer; and in addition, the first electron transport layer comprises a dopant of a lithium halide and/or lithium organic complex; and the second electron transport layer is free of a dopant; wherein the second electron transport layer consists of a matrix compound having the chemical formula Ia, Ib or Ic:

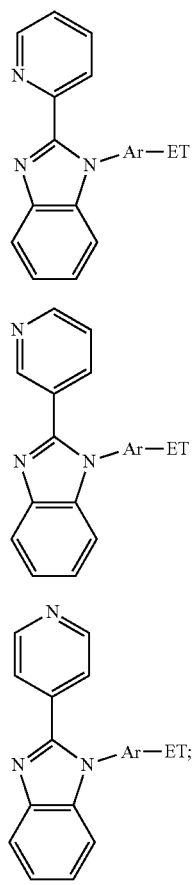(Ia)

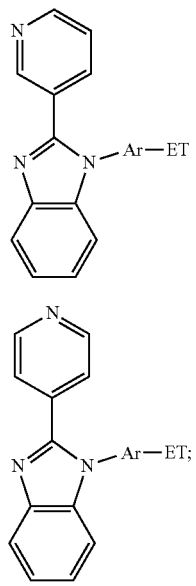(Ib)

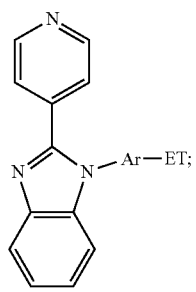(Ic)

wherein

Ar=substituted or unsubstituted arylene with 6 to 20 ring-forming carbon atoms, preferably 6 to 18 ring-forming carbon atoms, and more preferred 6 to 13 ring-forming carbon atoms; or carbazolylene;

ET=substituted or unsubstituted aryl group with 13 to 40 ring-forming carbon atoms; or a substituted or unsubstituted heteroaryl group with 14 to 40 ring-forming atoms, preferably a substituted or unsubstituted heteroaryl group with 20 to 24 ring-forming atoms.

According to one aspect, there is provided an organic light-emitting diode (OLED) comprising an emission layer and an electron transport layer stack of at least three electron transport layers, wherein a first electron transport layer, a second electron transport layer and a third electron transport layer comprises at least one matrix compound, wherein the matrix compound or compounds of the first electron transport layer and third electron transport layer are different to the matrix compound or compounds of the second electron transport layer; and in addition, at least the first electron transport layer, preferably the first and third electron transport layers, comprises a dopant of a lithium halide and/or lithium organic complex; and the second electron transport layer is free of a dopant; wherein at least one matrix compound of the second electron transport layer having the chemical formula Ia, Ib and/or Ic:

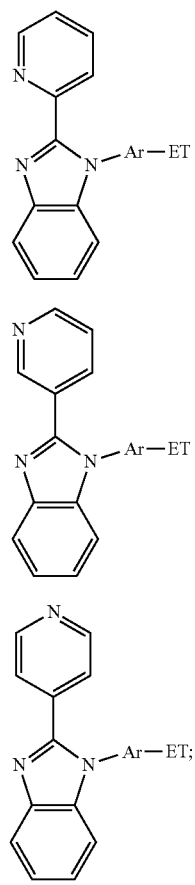(Ia)

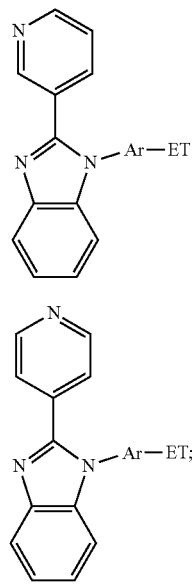(Ib)

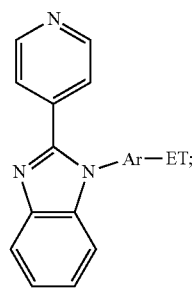(Ic)

wherein

Ar=substituted or unsubstituted arylene with 6 to 20 ring-forming carbon atoms, preferably 6 to 18 ring-forming carbon atoms; or carbazolylene;

ET=substituted or unsubstituted aryl group with 13 to 40 ring-forming carbon atoms; or a substituted or unsubstituted heteroaryl group with 14 to 40 ring-forming atoms, preferably a substituted or unsubstituted heteroaryl group with 20 to 24 ring-forming atoms.

According to one aspect, there is provided an organic light-emitting diode (OLED) comprising an emission layer and an electron transport layer stack of at least three electron transport layers, wherein a first electron transport layer, a second electron transport layer and a third electron transport layer comprises at least one matrix compound, wherein the matrix compound or compounds of the first electron transport layer and third electron transport layer are different to the matrix compound or compounds of the second electron transport layer; and in addition, at least the first electron transport layer, preferably the first and third electron transport layers, comprises a dopant of a lithium halide and/or lithium organic complex; and the second electron transport layer is free of a dopant; wherein at least one matrix compound of the second electron transport layer having the chemical formula Ia, Ib and/or Ic:

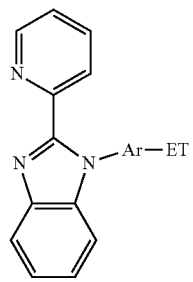

(Ia)

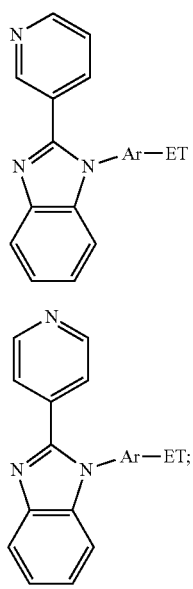

(Ib)

(Ic)

wherein

Ar=substituted or unsubstituted arylene with 6 to 20 ring-forming carbon atoms, preferably 6 to 18 ring-forming carbon atoms, and more preferred 6 to 13 ring-forming carbon atoms;

ET=a substituted or unsubstituted heteroaryl group with 20 to 24 ring-forming atoms.

According to one aspect, there is provided an organic light-emitting diode (OLED) comprising an emission layer and an electron transport layer stack of at least two electron transport layers, wherein a first electron transport layer and a second electron transport layer comprises at least one matrix compound, wherein the matrix compound or compounds of the first electron transport layer is/are different to the matrix compound or compounds of the second electron transport layer; and in addition, the first electron transport layer comprises a dopant of a lithium organic complex and is free of a lithium halide; and the second electron transport layer is free of a dopant; wherein at least one matrix compound of the second electron transport layer having the chemical formula Ia, Ib and/or Ic:

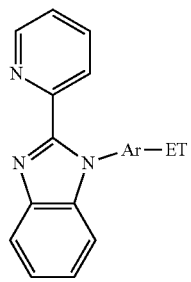

(Ia)

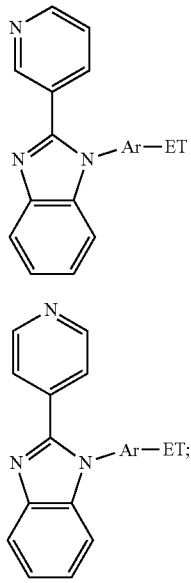

(Ib)

(Ic)

wherein

Ar=substituted or unsubstituted arylene with 6 to 20 ring-forming carbon atoms, preferably 6 to 18 ring-forming carbon atoms, and more preferred 6 to 13 ring-forming carbon atoms; or carbazolylene;

ET=substituted or unsubstituted aryl group with 13 to 40 ring-forming carbon atoms; or a substituted or unsubstituted heteroaryl group with 14 to 40 ring-forming atoms, preferably with 20 to 24 ring-forming atoms.

According to various aspects the organic light-emitting diode as mentioned before may comprise an electron transport layer stack having preferably two to four electron transport layers and more preferred two electron transport layers or three electron transport layers.

According to another aspect, there is provided an organic light-emitting diode (OLED) comprising an emission layer and an electron transport layer stack of at least three electron transport layers, preferably three electron transport layers, wherein a first electron transport layer, a second electron transport layer and a third electron transport layer comprises at least one matrix compound, wherein the matrix compound or matrix compounds of the first electron transport layer is/are different to the matrix compound or matrix compounds of the second electron transport layer;

the matrix compound or matrix compounds of the first electron transport layer is identical to the matrix compound or matrix compounds of the third electron transport layer; and in addition, the first and third electron transport layers comprise a dopant of a lithium halide and/or lithium organic complex; and wherein the second electron transport layer is free of a dopant and comprises at least one matrix compound having the chemical formula Ia, Ib and/or Ic:

(Ia)

[Structure: pyridin-2-yl connected to benzimidazole N-Ar-ET]

(Ib)

[Structure: pyridin-3-yl connected to benzimidazole N-Ar-ET]

(Ic)

[Structure: pyridin-4-yl connected to benzimidazole N-Ar-ET.]

According to various embodiments of the OLED the electron transport layer and/or electron transport layer stack may comprise as a dopant a lithium organic complex only.

According to various aspects the organic light-emitting diode (OLED) may contain two or more electron transport layers, for example two or three electron transport layers.

According to another aspect, there is provided an organic light-emitting diode (OLED) comprising an emission layer and an electron transport layer stack of at least two electron transport layers, preferably two electron transport layers, wherein a first electron transport layer and a second electron transport layer comprises at least one matrix compound of a phosphine oxide, wherein
the phosphine oxide matrix compound or phosphine oxide matrix compounds of the first electron transport layer is/are different to the matrix compounds of the second electron transport layer having the chemical formula Ia, Ib and/or Ic:

(Ia)

[Structure: pyridin-2-yl connected to benzimidazole N-Ar-ET]

(Ib)

[Structure: pyridin-3-yl connected to benzimidazole N-Ar-ET]

(Ic)

[Structure: pyridin-4-yl connected to benzimidazole N-Ar-ET;]

and in addition,
the first electron transport layer comprises a dopant of a lithium halide and/or lithium organic complex; and wherein
the second electron transport layer is free of a dopant.

According to various aspects the organic light-emitting diode as mentioned before may comprise an electron transport layer stack having three electron transport layers.

According to various aspects the organic light-emitting diode as mentioned before may comprise an electron injection layer; preferably the electron injection layer is arranged between the electron transport layer and the cathode electrode.

More preferred the OLED with two electron transport layers may comprise an electron injection layer.

The OLED may comprise an electron injection layer which is arranged between the electron transport layer stack and the cathode electrode, wherein the electron transport layer stack is formed of two electron transport layers.

According to various aspects the organic light-emitting diode as described above with three electron transport layers may be free of an electron injection layer.

According to one aspect, there is provided an organic light-emitting diode (OLED) comprising an emission layer and an electron transport layer stack of at least two electron transport layers, wherein a first electron transport layer and a second electron transport layer comprises at least one matrix compound, wherein
the matrix compound or compounds of the first electron transport layer is/are different to the matrix compound or compounds of the second electron transport layer; and in addition, the first electron transport layer comprises a dopant of a lithium halide and/or lithium organic complex; and
the second electron transport layer is free of a dopant;
wherein
at least one matrix compound of the second electron transport layer having the chemical formula Ia, Ib and/or Ic:

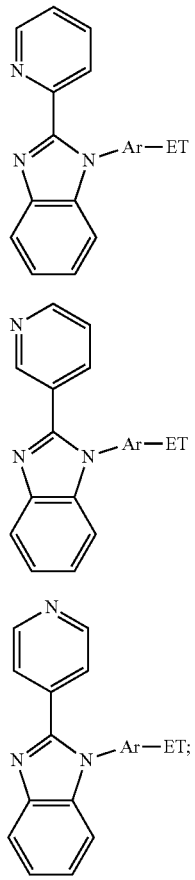

wherein
Ar=substituted or unsubstituted arylene with 6 to 20 ring-forming carbon atoms, preferably 6 to 18 ring-forming carbon atoms, and more preferred 6 to 13 ring-forming carbon atoms; or carbazolylene;
ET=substituted or unsubstituted aryl group with 13 to 40 ring-forming carbon atoms; or a substituted or unsubstituted heteroaryl group with 14 to 40 ring-forming atoms, preferably with 20 to 24 ring-forming atoms;
and wherein the organic light-emitting diode comprises in addition an electron injection layer, preferably the electron injection layer is arranged between the electron transport layer and the cathode electrode, wherein the electron injection layer may:
comprises a matrix compound of a phosphine oxide compound substituted with aryl, heteroaryl or alkyl group, preferably 3-Phenyl-3H-benzo[b]dinaphtho[2,1-d:1',2'-f]phosphepine-3-oxide, and doped with a lithium halide or doped with a lithium organic complex, preferably lithium tetra(1H-pyrazol-1-yl)borate; or
comprises a matrix compound of a phosphine oxide compound substituted with aryl, heteroaryl or alkyl group, preferably (3-(dibenzo[c,h]acridin-7-yl)phenyl)diphenylphosphine oxide or 3-Phenyl-3H-benzo[b]dinaphtho[2,1-d:1',2'-f]phosphepine-3-oxide, and doped with an elemental metal selected from a group comprising alkali, alkaline earth or rare earth metals, preferably Li, Cs, Mg, Ca, Yb, or Sm; or
consist of a metal halide or of an metal organic complex, preferably LiQ, AlQ3, ZrQ4, KF or LiF, wherein Q is a 8-hydroxyquinolate;
consists of an alkali, alkaline earth or of a rare earth metal, preferably Li, Cs, Mg, Ca, Yb, or Sm.

According to one embodiment the electron injection layer is arranged between the electron transport layer and the cathode electrode, wherein the electron injection layer has a layer thickness of about ≥0.5 nm to about ≤5 nm and may:
comprises a matrix compound of a phosphine oxide compound substituted with aryl, heteroaryl or alkyl group, preferably 3-Phenyl-3H-benzo[b]dinaphtho[2,1-d:1',2'-f]phosphepine-3-oxide, and doped with a lithium halide or doped with a lithium organic complex, preferably lithium tetra(1H-pyrazol-1-yl)borate; or
comprises a matrix compound of a phosphine oxide compound substituted with aryl, heteroaryl or alkyl group, preferably (3-(dibenzo[c,h]acridin-7-yl)phenyl)diphenylphosphine oxide or 3-Phenyl-3H-benzo[b]dinaphtho[2,1-d:1',2'-f]phosphepine-3-oxide, and doped with an elemental metal selected from a group comprising alkali, alkaline earth or rare earth metals, preferably Li, Cs, Mg, Ca, Yb, or Sm; or
consist of a metal halide or of an metal organic complex, preferably LiQ, AlQ3, ZrQ4, KF or LiF, wherein Q is a 8-hydroxyquinolate;
consist of an alkali, alkaline earth or rare earth metal, preferably Li, Cs, Mg, Ca, Yb, or Sm.

Surprisingly, it was found that the voltage was reduced and efficiency EQE increased by inserting a second undoped electron transport layer between the first electron transport layer and the cathode.

According to various aspects of the OLED the electron transport layers of the electron transport layer stack, preferably the first electron transport layer and the second electron transport layer; or further preferred the first electron transport layer, the second electron transport layer and the third electron transport layer; may have similar or identical energy levels, more preferred the off-set in LUMO level is about ≤0.35 eV, and further more preferred the off-set in LUMO level is about ≤0.2 eV.

For the following defined terms, these definitions shall be applied, unless a different definition is given in the claims or elsewhere in this specification.

In the context of the present specification the term "different" or "differs" in connection with the matrix material means that the matrix material differs in their structural formula.

In the context of the present specification the term "different" or "differs" in connection with the lithium compound means that the lithium compound differs in their structural formula.

The external quantum efficiency, also named EQE, is measured in percent (%).

The lifetime, also named LT, between starting brightness and 97% of the original brightness is measured in hours (h).

The voltage, also named V, is measured in Volt (V) at 10 milliAmpere per square centimeter (mA/cm$^2$) in bottom emission devices and at 15 mA/cm$^2$ in top emission devices.

The color space is described by coordinates CIE-x and CIE-y (International Commission on Illumination 1931).

For blue emission the CIE-y is of particular importance. A smaller CIE-y denotes a deeper blue color.

The highest occupied molecular orbital, also named HOMO, and lowest unoccupied molecular orbital, also named LUMO, are measured in electron volt (eV).

The term "OLED" and "organic light-emitting diode" is simultaneously used and having the same meaning.

The term "electron transport layer stack" as used in the specification comprises at least two electron transport layers or at least three electron transport layers.

The term "different compound" as used in connection with the matrix compound means that the matrix compound differs from the other matrix compound in its chemical formula.

As used herein, "weight percent", "wt.-%", "percent by weight", "% by weight", and variations thereof refer to a composition, component, substance or agent as the weight of that component, substance or agent of the respective electron transport layer divided by the total weight of the respective electron transport layer thereof and multiplied by 100. It is understood that the total weight percent amount of all components, substances and agents of the respective electron transport layer are selected such that it does not exceed 100 wt.-%.

All numeric values are herein assumed to be modified by the term "about", whether or not explicitly indicated. As used herein, the term "about" refers to variation in the numerical quantity that can occur. Whether or not modified by the term "about" the claims include equivalents to the quantities.

It should be noted that, as used in this specification and the appended claims, the singular forms "a", "an", and "the" include plural referents unless the content clearly dictates otherwise.

The term "free of", "does not contain", "does not comprise" does not exclude impurities. Impurities have no technical effect with respect to the object achieved by the present invention.

The term "alkyl" refers to straight-chain or branched alkyl groups. The term "1 to 20 carbon atoms" as used herein refers to straight-chain or branched alkyl groups having 1 to 20 carbon atoms. The alkyl groups can be selected from the group comprising methyl, ethyl and the isomers of propyl, butyl or pentyl, such as isopropyl, isobutyl, tert.-butyl, sec.-butyl and/or isopentyl. The term "aryl" refers to aromatic groups for example phenyl or naphthyl.

Herein, when a first element is referred to as being formed or disposed "on" a second element, the first element can be disposed directly on the second element or one or more other elements may be disposed there between. When a first element is referred to as being formed or disposed "directly on" a second element, no other elements are disposed there between.

According to various aspects of the OLED the electron transport layer and/or electron transport layer stack is free of elemental metal.

According to various aspects of the OLED the electron transport layer stack may contain at least one electron transport layer, preferably the second electron transport layer, which is free of a metal salt and/or a metal organic complex.

According to various aspects of the OLED the electron transport layer stack contains at least one electron transport layer, preferably the second electron transport layer, which is free of a lithium compound selected from the group lithium halide and/or lithium organic complex.

In the context that the electron transport layer or layers are free of a dopant, metal salt, and/or metal organic complex, the term "free of" means that the so called "free off" electron transport layer or layers may comprise of about 5 wt.-% or less of a dopant, metal salt and/or a metal organic complex, preferably about 0.5 wt.-% or less, and more preferably about 0.05 wt.-% or less, and even more preferably about 0.005 wt.-% or less of a dopant, a metal salt and/or metal organic complex and most preferred is free of a dopant, metal salt and/or a metal organic complex.

According to various aspects, there is provided an organic light-emitting diode, whereby the organic light-emitting diode may not contain a charge generation layer (CGL).

According to various aspects, wherein for an OLED comprising two electron transport layer or three electron transport layers the OLED may contain at least one electron injection layer.

According to various aspects, wherein for an electron transport layer stack of at least two electron transport layers the first electron transport layer is arranged closest to an emission layer and the second electron transport layer is arranged closest to a cathode.

According to various aspects, wherein for an electron transport layer stack of three electron transport layers the first electron transport layer is arranged closest to an emission layer, the second electron layer is sandwiched between the first and the third electron transport layer and the third electron transport layer is arranged closest to a cathode.

The organic light-emitting diode can be a bottom emission OLED or a top emission OLED.

Dopant

According to various aspects the lithium halide dopant can be selected from the group comprising LiF, LiCl, LiBr or LiJ, and preferably LiF.

According to various aspects the dopant of a lithium compound can be a lithium organic complex and preferably the dopant of the lithium compound can be selected from the group comprising a lithium quinolate, a lithium borate, a lithium phenolate, a lithium pyridinolate or a lithium Schiff base and lithium fluoride, preferably a lithium 2-(diphenylphosphoryl)-phenolate, lithium tetra(1H-pyrazol-1-yl)borate, a lithium quinolate of formula (IV), a lithium 2-(pyridin-2-yl)phenolate and LiF, and more preferred selected from the group comprising a lithium 2-(diphenylphosphoryl)-phenolate, lithium tetra(1H-pyrazol-1-yl)borate, a lithium quinolate of formula (IV) and a lithium 2-(pyridin-2-yl)phenolate.

More preferably the lithium organic complex can be selected from the group comprising a lithium quinolate, a lithium borate, a lithium phenolate, a lithium pyridinolate or a lithium Schiff base; preferably the lithium organic complex, is selected from the group comprising a lithium quinolate, a lithium borate, a lithium phenolate, a lithium pyridinolate or a lithium Schiff base;

preferably the lithium quinolate has the formula II, III or IV:

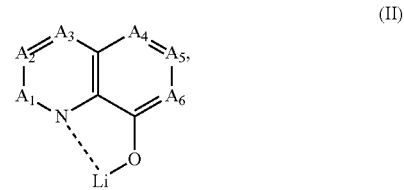

(II)

-continued

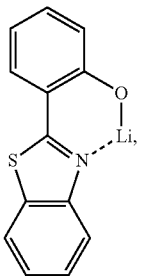
(III)

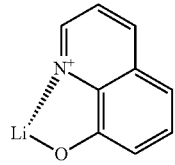
(IV)

wherein

A1 to A6 are same or independently selected from CH, CR, N, O;

R is same or independently selected from hydrogen, halogen, alkyl or aryl or heteroaryl with 1 to 20 carbon atoms; and more preferred A1 to A6 are CH;

preferably the lithium borate is a lithium tetra(1H-pyrazol-1-yl)borate;

preferably the lithium phenolate is a lithium 2-(pyridin-2-yl)phenolate, a lithium 2-(diphenylphosphoryl)phenolate, a lithium imidazol phenolates, or a lithium 2-(pyridin-2-yl)phenolate and more preferred a lithium 2-(1-phenyl-1H-benzo[d]imidazol-2-yl)phenolate, or a lithium 2-(benzo[d]oxazol-2-yl)phenolate;

preferably the lithium pyridinolate is a lithium 2-(diphenylphosphoryl)pyridin-3-olate, preferably the lithium Schiff base has the structure 100, 101, 102 or 103:

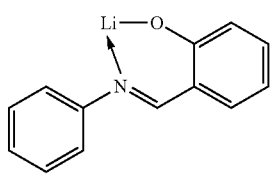
100

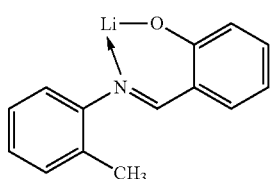
101

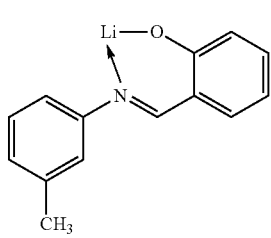
102

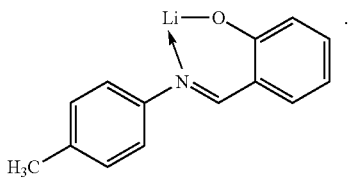
103

Quinolates that can be suitable used are disclosed in WO 2013079217 A1 and incorporated by reference.

According to various embodiments of the organic light-emitting diode (OLED) of the present invention the organic ligand of the lithium organic complex can be a borate based organic ligand, preferably the lithium organic complex is a lithium tetra(1H-pyrazol-1-yl)borate. Borate based organic ligands that can be suitable used are disclosed in WO 2013079676 A1 and incorporated by reference.

According to various embodiments of the organic light-emitting diode (OLED) of the present invention the organic ligand of the lithium organic complex can be a phenolate ligand, Preferably the lithium organic complex is a lithium 2-(diphenylphosphoryl)phenolate. Phenolate ligands that can be suitable used are disclosed in WO 2013079678 A1 and incorporated by reference.

Further, phenolate ligands can be selected from the group comprising pyridinolate, preferably 2-(diphenylphosphoryl)pyridin-3-olate. Pyridine phenolate ligands that can be suitable used are disclosed in JP 2008195623 and incorporated by reference.

In addition, phenolate ligands can be selected from the group comprising imidazol phenolates, preferably 2-(1-phenyl-1H-benzo[d]imidazol-2-yl)phenolate. Imidazol phenolate ligands that can be suitable used are disclosed in JP 2001291593 and incorporated by reference.

Also, phenolate ligands can be selected from the group comprising oxazol phenolates, preferably 2-(benzo[d]oxazol-2-yl)phenolate. Oxazol phenolate ligands that can be suitable used are disclosed in US 20030165711 and incorporated by reference.

Lithium Schiff base metal organic complexes can be use. Lithium Schiff base metal organic complexes that can be suitable used having the structure 100, 101, 102 or 103:

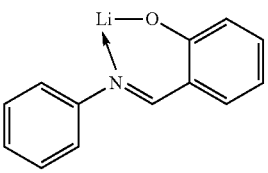
100

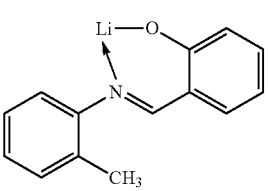
101

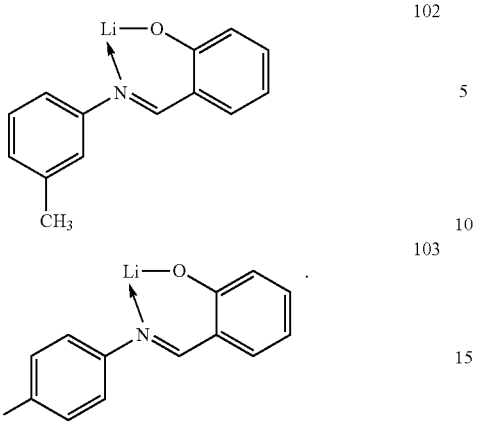

Suitable organic ligands to form a lithium organic complex that can be used for the first electron transport layer and/or the second electron transport layer are disclosed, and incorporated by reference, for example in US 2014/0048792 and Kathirgamanathan, Poopathy; Arkley, Vincent; Surendrakumar, Sivagnanasundram; Chan, Yun F.; Ravichandran, Seenivasagam; Ganeshamurugan, Subramaniam; Kumaraverl, Muttulingam; Antipan-Lara, Juan; Paramaswara, Gnanamolly; Reddy, Vanga R., Digest of Technical Papers—Society for Information Display International Symposium (2010), 41(Bk. 1), 465-468.

Suitable lithium organic complexes that can be most preferably used for the electron transport layer are summarized in Table 1 below.

TABLE 1

| | Lithium organic complex that can be suitable used | | |
|---|---|---|---|
| | IUPAC name | Structure | Reference |
| LiQ | lithium 8-hydroxyquinolate | | WO 2013079217 A1 |
| Li-1 | lithium tetra(1H-pyrazol-1-yl)borate | | WO 2013079676 A1 |
| Li-2 | lithium 2-(diphenyl-phosphoryl)phenolate | | WO 2013079678A1 |

TABLE 1-continued

Lithium organic complex that can be suitable used

| | IUPAC name | Structure | Reference |
| --- | --- | --- | --- |
| Li-3 | lithium 2-(pyridin-2-yl)phenolate | 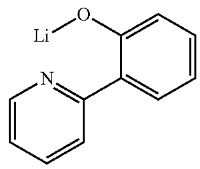 | JP2 008195623 |
| Li-4 | lithium 2-(1-phenyl-1H-benzo[d]imidazol-2-yl)phenolate | 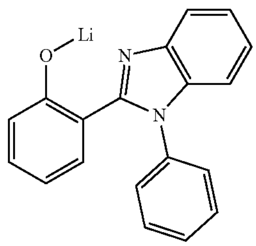 | JP 2001291593 |
| Li-5 | lithium 2-(benzo[d]oxazol-2-yl)phenolate | 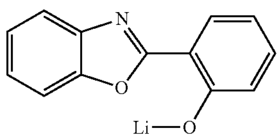 | US 20030165711 |
| Li-6 | lithium 2-(diphenylphosphoryl)pyridin-3-olate | 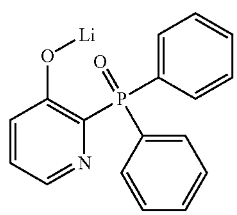 | EP 2724388 |

According to various embodiments of the organic light-emitting diode, wherein
the first electron transport layer may comprise about ≥10 wt.-% to about ≤70 wt.-%, preferably about ≥20 wt.-% to about ≤65 wt.-%, and also preferred about ≥50 wt.-% to about ≤60 wt.-% of a lithium halide or a lithium organic complex; or
the first electron transport layer and the third electron transport layer may comprise each about ≥10 wt.-% to about ≤70 wt.-%, preferably about ≥20 wt.-% to about ≤65 wt.-% and also preferred about ≥50 wt.-% to about ≤60 wt.-% of a lithium halide or a lithium organic complex;
wherein the weight percent of the lithium halide and the lithium organic complex is based on the total weight of the corresponding electron transport layer.

Matrix Compounds

According to various embodiments of the organic light-emitting diode (OLED) of the present invention the electron transport layer or the electron transport layers of an electron transport layer stack, may comprise at least one matrix compound each.

According to various embodiments of the organic light-emitting diode, wherein the first electron transport layer and/or the third electron transport layer may comprise of at least one matrix compound.

According to various embodiments of the organic light-emitting diode, wherein the first electron transport layer and/or the third electron transport layer may comprise independent of each other one, two, three or more matrix compounds, preferably one matrix compound; whereby the matrix compound or matrix compounds selected same or different.

According to various embodiments of the organic light-emitting diode, wherein the second electron transport layer may consist of at least one matrix compound.

According to various embodiments the organic light-emitting diode (OLED) may comprise an electron transport layer stack of at least two electron transport layers or at least three electron transport layers, wherein each electron transport layer comprises at least one matrix compound, whereby the matrix compound of the first and third electron transport layers are selected same or different; and whereby the matrix compound of the second electron transport layer is different to the first electron transport layer, or is different to the first and third electron transport layer or is different to all other electron transport layer/s, whereby the matrix compound of the second electron transport layer having the chemical formula Ia, Ib and/or Ic:

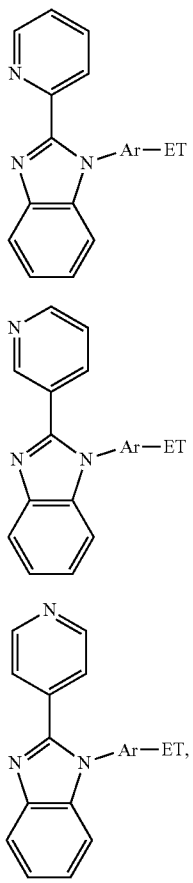

(Ia)

(Ib)

(Ic)

wherein

Ar=substituted or unsubstituted arylene with 6 to 20 ring-forming carbon atoms; or carbazolylene;

ET=substituted or unsubstituted aryl group with 13 to 40 ring-forming carbon atoms; or a substituted or unsubstituted heteroaryl group with 14 to 40 ring-forming atoms.

According to various embodiments of the organic light-emitting diode (OLED) the matrix compound, except for the second electron transport layer, can be selected from:

an anthracene compound substituted with aryl, heteroaryl or alkyl groups, preferably 9,10-di(2-naphthyl)anthracene and/or 3-[3'-(10-phenyl-9-anthracenyl)[1,1'-biphenyl]-4-yl]-quinoline;

a benzimidazole compound substituted with aryl, heteroaryl or alkyl groups, preferably 2-(4-(9,10-di(naphthalen-2-yl)anthracene-2-yl)phenyl)-1-phenyl-1H-benzo[d]imidazole and/or 1-(4-(10-([1,1'-biphenyl]-4-yl)anthracen-9-yl)phenyl)-2-ethyl-1H-benzo[d]imidazole;

a phosphine oxide compound substituted with aryl, heteroaryl or alkyl groups, preferably (3-(dibenzo[c,h]acridin-7-yl)phenyl)diphenylphosphine oxide, 3-phenyl-3H-benzo[b]dinaphtho[2,1-d:1',2'-f]phosphepine-3-oxide, phenyldi(pyren-1-yl)phosphine oxide, bis(4-(anthracen-9-yl)phenyl)(phenyl)phosphine oxide, (3-(9,10-di(naphthalen-2-yl)anthracen-2-yl)phenyl) diphenylphosphine oxide, phenyldi(pyren-1-yl)phosphine oxide, diphenyl(5-(pyren-1-yl)pyridin-2-yl)phosphine oxide, diphenyl(4'-(pyren-1-yl)-[1,1'-biphenyl]3-yl)phosphine oxide, diphenyl(4'-(pyren-1-yl)[1,1'-biphenyl]-3-yl)phosphine oxide, (3'-(dibenzo[c,h]acridin-7-yl)-[1,1'-biphenyl]-4-yl) diphenylphosphine oxide, (3-(10-(naphthalen-2-yl)anthracen-9-yl)phenyl)diphenylphosphine oxide and/ or phenyl bis(3-(pyren-1-yl)phenyl)phosphine oxide;

a phenanthroline compound substituted with aryl or heteroaryl groups, preferably 2,4,7,9-tetraphenyl-1,10-phenanthroline, 4,7-diphenyl-2,9-di-p-tolyl-1,10-phenanthroline, 2,9-di(biphenyl-4-yl)-4,7-diphenyl-1,10-phenanthroline and/or 3,8-bis(6-phenyl-2-pyridinyl)-1,10-phenanthroline;

a quinazoline compound substituted with aryl or heteroaryl groups, preferably 9-phenyl-9'-(4-phenyl-2-quinazolinyl)-3,3'-bi-9H-carbazole;

a benzo[h]quinazoline compound substituted with aryl or heteroaryl groups, preferably 4-(2-naphthalenyl)-2-[4-(3-quinolinyl)phenyl]-benzo[h]quinazoline;

a pyrido[3,2-h]quinazoline compound substituted with aryl or heteroaryl groups, preferably 4-(naphthalen-1-yl)-2,7,9-triphenylpyrido[3,2-h]quinazoline;

a triazine compound substituted with aryl or heteroaryl groups, preferably 4,4'-bis(4,6-diphenyl-1,3,5-triazin-2-yl)biphenyl, 3-[4-(4,6-di-2-naphthalenyl-1,3,5-triazin-2-yl)phenyl]quinoline and/or 2-[3-(6'-methyl[2,2'-bipyridin]-5-yl)-5-(9-phenanthrenyl)phenyl]-4,6-diphenyl-1,3,5-triazine and/or an acridine compound substituted with aryl or heteroaryl groups, preferably 7-(naphthalen-2-yl)dibenzo[c,h]acridine.

According to various embodiments of the organic light-emitting diode (OLED) a matrix compound for the electron transport layer, except for the second electron transport layer, can be selected from a phosphine oxide compound substituted with aryl, heteroaryl or alkyl groups, preferably (3-(dibenzo[c,h]acridin-7-yl) phenyl)diphenylphosphine oxide, 3-phenyl-3H-benzo[b]dinaphtho[2,1-d:1',2'-f]phosphepine-3-oxide, phenyldi(pyren-1-yl)phosphine oxide, bis(4-(anthracen-9-yl)phenyl)(phenyl)phosphine oxide, (3-(9, 10-di(naphthalen-2-yl)anthracen-2-yl)phenyl) diphenyl phosphine oxide, diphenyl(5-(pyren-1-yl)pyridin-2-yl)phosphine oxide, diphenyl(4'-(pyren-1-yl)-[1,1'-biphenyl]-3-yl) phosphine oxide, (3'-(dibenzo[c,h]acridin-7-yl)-[1,1'-biphenyl]-4-yl)diphenylphos—phine oxide, (3-(10-(naphthalen-2-yl)anthracen-9-yl)phenyl)diphenylphosphine oxide and/or phenyl bis(3-(pyren-1-yl)phenyl)phosphine oxide.

According to another aspect the OLED may comprises a first electron transport layer comprising a matrix material selected from the group comprising:

a phosphine oxide compound substituted with aryl, heteroaryl or alkyl groups, preferably (3-(dibenzo[c,h]acridin-7-yl)phenyl)diphenylphosphine oxide, 3-phenyl-3H-benzo[b]dinaphtho[2,1-d:1',2'-f]phosphepine-3-oxide, phenyldi(pyren-1-yl)phosphine oxide, bis(4-(anthracen-9-yl)phenyl)(phenyl)phosphine oxide, (3-(9,10-di(naphthalen-2-yl)anthracen-2-yl)phenyl)diphenylphosphine oxide, diphenyl(5-(pyren-1-yl)pyridin-2-yl)phosphine oxide, diphenyl(4'-(pyren-1-yl)-[1,1'-biphenyl]-3-yl)phosphine oxide, phenyl bis(3-(pyren-1-yl)phenyl)phosphine oxide and/or (3'-(dibenzo[c,h]acridin-7-yl)-[1,1'-biphenyl]-4-yl)diphenylphosphine oxide, (3-(10-(naphthalen-2-yl)anthracen-9-yl)phenyl)diphenylphosphine oxide, preferably (3-(dibenzo[c,h]acridin-7-yl)phenyl)diphenylphosphine oxide or (3'-(dibenzo[c,h]acridin-7-yl)[1,1'-biphenyl]-4-yl) diphenylphosphine oxide; and/or a benzimidazole compound substituted with aryl, heteroaryl or alkyl groups, preferably 2-(4-(9,10-di(naphthalen-2-yl)anthracene-2-yl)phenyl)-1-phenyl-1H-benzo[d]imidazole and/or 1-(4-(10-([1,1'-biphenyl]-4-yl)anthracen-9-yl)phenyl)-2-ethyl-1H-benzo[d]imidazole;

the second electron transport layer comprises a matrix material having the chemical formula Ia, Ib and/or Ic:

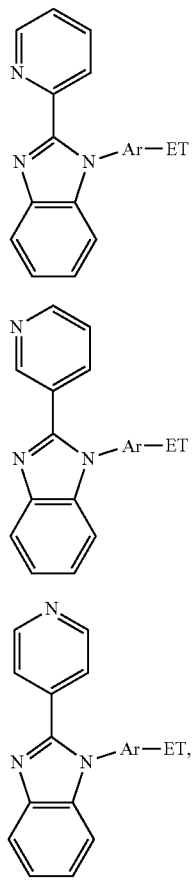

wherein
Ar=substituted or unsubstituted arylene with 6 to 20 ring-forming carbon atoms; or carbazolylene, preferably 6 to 18 ring-forming carbon atoms, and more preferred 6 to 13 ring-forming carbon atoms;
ET=substituted or unsubstituted aryl group with 13 to 40 ring-forming carbon atoms; or a substituted or unsubstituted heteroaryl group with 14 to 40 ring-forming atoms, preferably a substituted or unsubstituted heteroaryl group with 20 to 24 ring-forming atoms;
the optional third electron transport layer comprises a matrix material selected from the group comprising:
a phosphine oxide compound substituted with aryl heteroaryl or alkyl groups, preferably (3-(dibenzo[c,h]acridin-7-yl)phenyl)diphenylphosphine oxide, 3-phenyl-3H-benzo[b]dinaphtho[2,1-d:1',2'-f]phosphepine-3-oxide, phenyldi(pyren-1-yl)phosphine oxide, bis(4-(anthracen-9-yl)phenyl)(phenyl)phosphine oxide, (3-(9,10-di(naphthalen-2-yl)anthracen-2-yl)phenyl)diphenylphosphine oxide, diphenyl(5-(pyren-1-yl)pyridin-2-yl)phosphine oxide, diphenyl(4'-(pyren-1-yl)-[1,1'-biphenyl]-3-yl)phosphine oxide, phenyl bis(3-(pyren-1-yl)phenyl)phosphine oxide and/or (3'-(dibenzo[c,h]acridin-7-yl)-[1,1'-biphenyl]-4-yl)diphenylphosphine oxide, 3-(10-(naphthalen-2-yl)anthracen-9-yl)phenyl)diphenylphosphine oxide, preferably (3-(dibenzo[c,h]acridin-7-yl)phenyl)diphenylphosphine oxide or (3'-(dibenzo[c,h]acridin-7-yl)-[1,1'-biphenyl]-4-yl)diphenylphosphine oxide; and/or
a benzimidazole compound substituted with aryl, heteroaryl or alkyl groups, preferably 2-(4-(9,10-di(naphthalen-2-yl)anthracene-2-yl)phenyl)-1-phenyl-1H-benzo[d]imidazole and/or 1-(4-(10-([1,1'-biphenyl]-4-yl)anthracen-9-yl)phenyl)-2-ethyl-1H-benzo[d]imidazole; whereby
the matrix material of the second electron transport layer is selected different to the matrix material of the first electron transport layer and the optional third electron transport layer.

According to another embodiment of the OLED, the second electron transport layer comprises at least one matrix material having the chemical formula Ia, Ib and/or Ic:

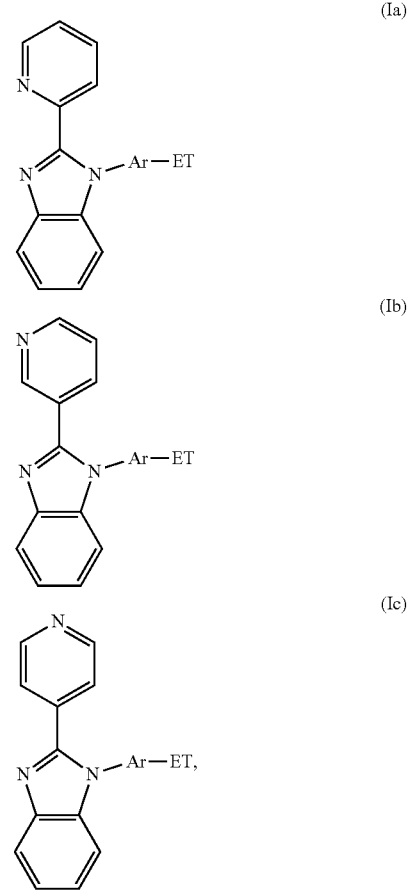

wherein
Ar=substituted or unsubstituted arylene with 6 to 20 ring-forming carbon atoms, preferably 6 to 18 ring-forming carbon atoms, and more preferred 6 to 13 ring-forming carbon atoms; or carbazolylene;
ET=substituted or unsubstituted aryl group with 13 to 40 ring-forming carbon atoms, preferably 14 to 26 ring-forming carbon atoms, and more preferred 14 to 22 ring-forming carbon atoms; or a substituted or unsubstituted heteroaryl group with 14 to 40 ring-forming atoms, preferably 20 to 24 ring-forming atoms.

According to another aspect of the second electron transport layer, Ar of Formula Ia, Ib and Ic can be selected from the group of:

unsubstituted arylene:
o-phenylene, m-phenylene, p-phenylene, biphenyl-2,2'-diyl, biphenyl-3,3'diyl, biphenyl-4,4'diyl, biphenyl-3,4'-diyl, p-terphenyl-4,4'-diyl, p-terphenyl-3,3'-diyl, p-terphenyl-2,2'-diyl, m-terphenyl-4,4'-diyl, m-terphenyl-3,3'-diyl, m-terphenyl-2,2'-diyl, o-terphenyl-4,4'-diyl, o-terphenyl-3,3'-diyl, o-terphenyl-2,2'-diyl; naphthalen-2,6-diyl, naphthalen-1,4-diyl; or substituted arylene or carbazolylene:
o-phenylene, m-phenylene, p-phenylene, biphenyl-2,2'-diyl, biphenyl-3,3'diyl, biphenyl-4,4'diyl, biphenyl-3,4'-diyl, fluoren-2,7-diyl, fluoren-3,6-diyl, carbazol-3,6-diyl, carbazole-2,7-diyl, p-terphenyl-4,4'-diyl, p-terphenyl-3,3'-diyl, p-terphenyl-2,2'-diyl, m-terphenyl-4,4'-diyl, m-terphenyl-3,3'-diyl, m-terphenyl-2,2'-diyl, o-terphenyl-4,4'-diyl, o-terphenyl-3,3'-diyl, o-terphenyl-2,2'-diyl; naphthalen-2,6-diyl, naphthalen-1,4-diyl; wherein the substituent of the substituted arylene or carbazolylene is selected from the group of an alkyl group with 1 to 15 carbon atoms, preferably 1 to 12 carbon atoms, more preferred 1 to 4 carbon atoms; an alkoxy group with 1 to 15 carbon atoms, preferably 1 to 5 carbon atoms and more preferred 1 to 2 carbon atoms.

According to another aspect of the second electron transport layer, Ar of Formula Ia, Ib and Ic can be selected from the group of A1 to A69:

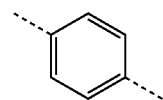

(A1)

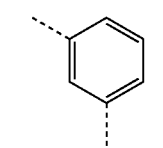

(A2)

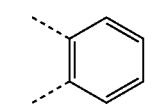

(A3)

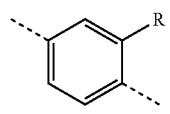

(A4)

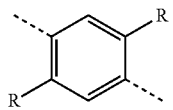

(A5)

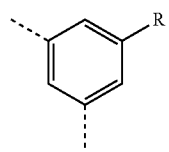

(A6)

-continued

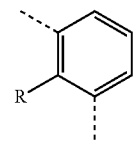

(A7)

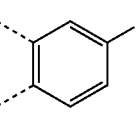

(A8)

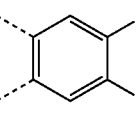

(A9)

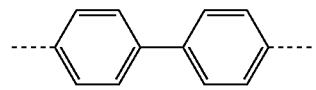

(A10)

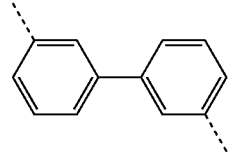

(A11)

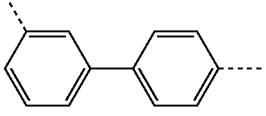

(A11)

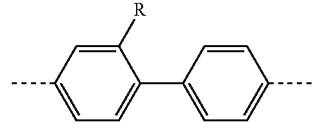

(A12)

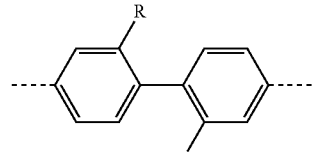

(A13)

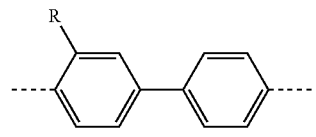

(A14)

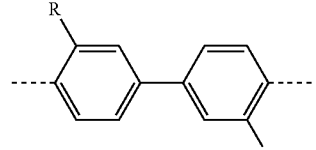

(A15)

(A16)

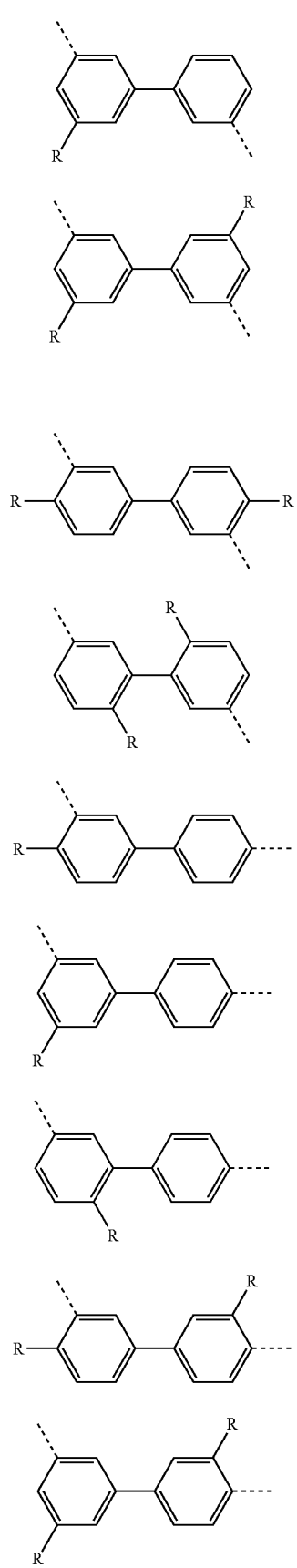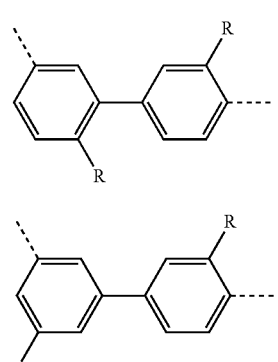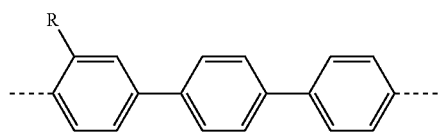

(A36) 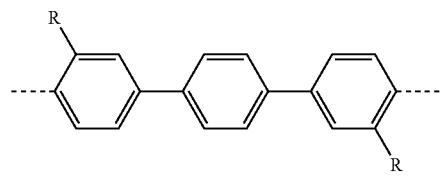
(A37) 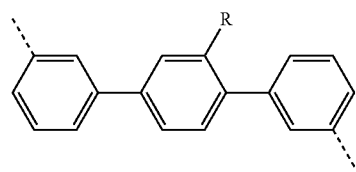
(A38) 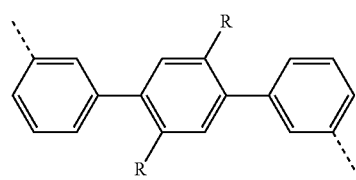
(A39) 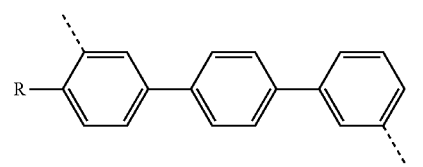
(A40) 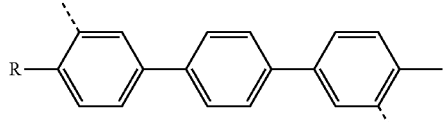
(A41) 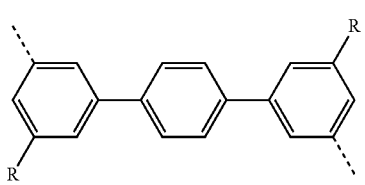
(A42) 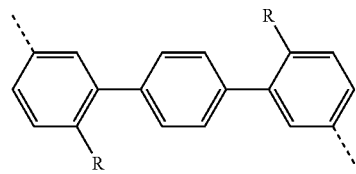
(A43) 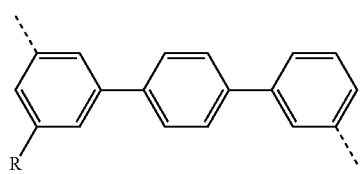
(A44) 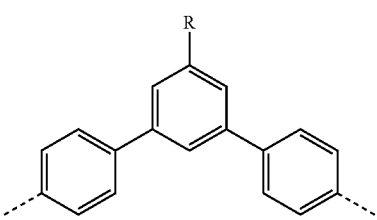
(A45) 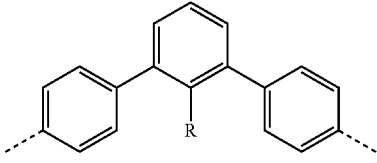
(A46) 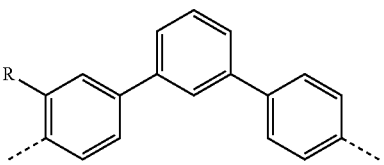
(A47) 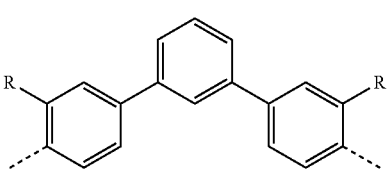
(A48) 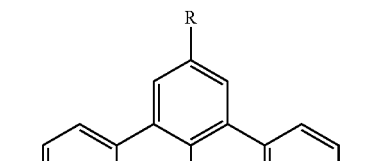
(A49) 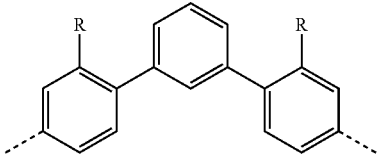
(A50) 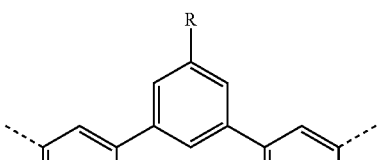
(A51) 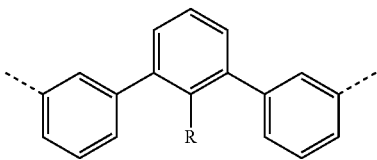
(A52) 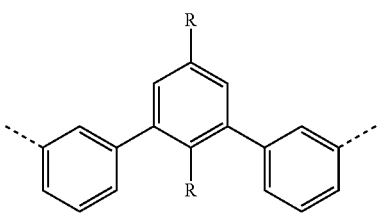

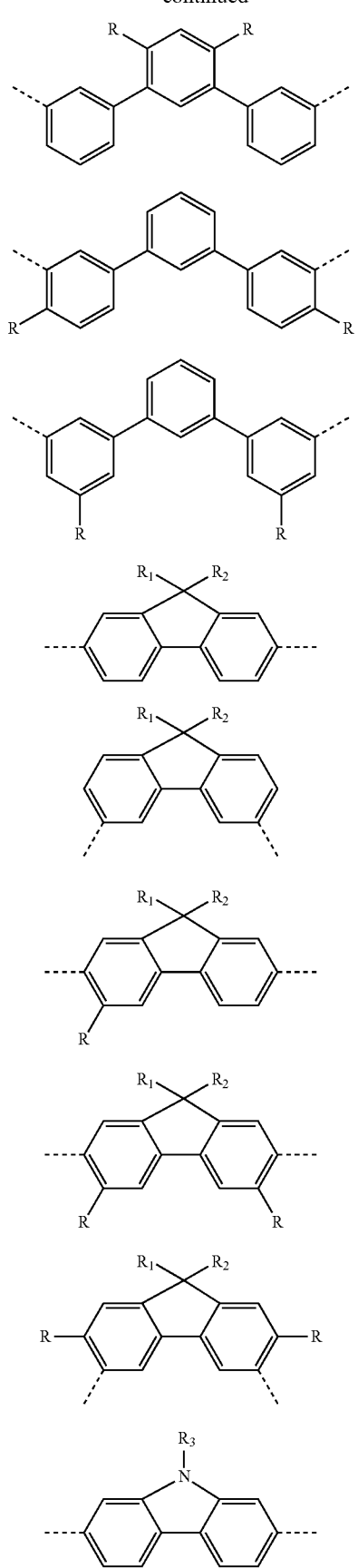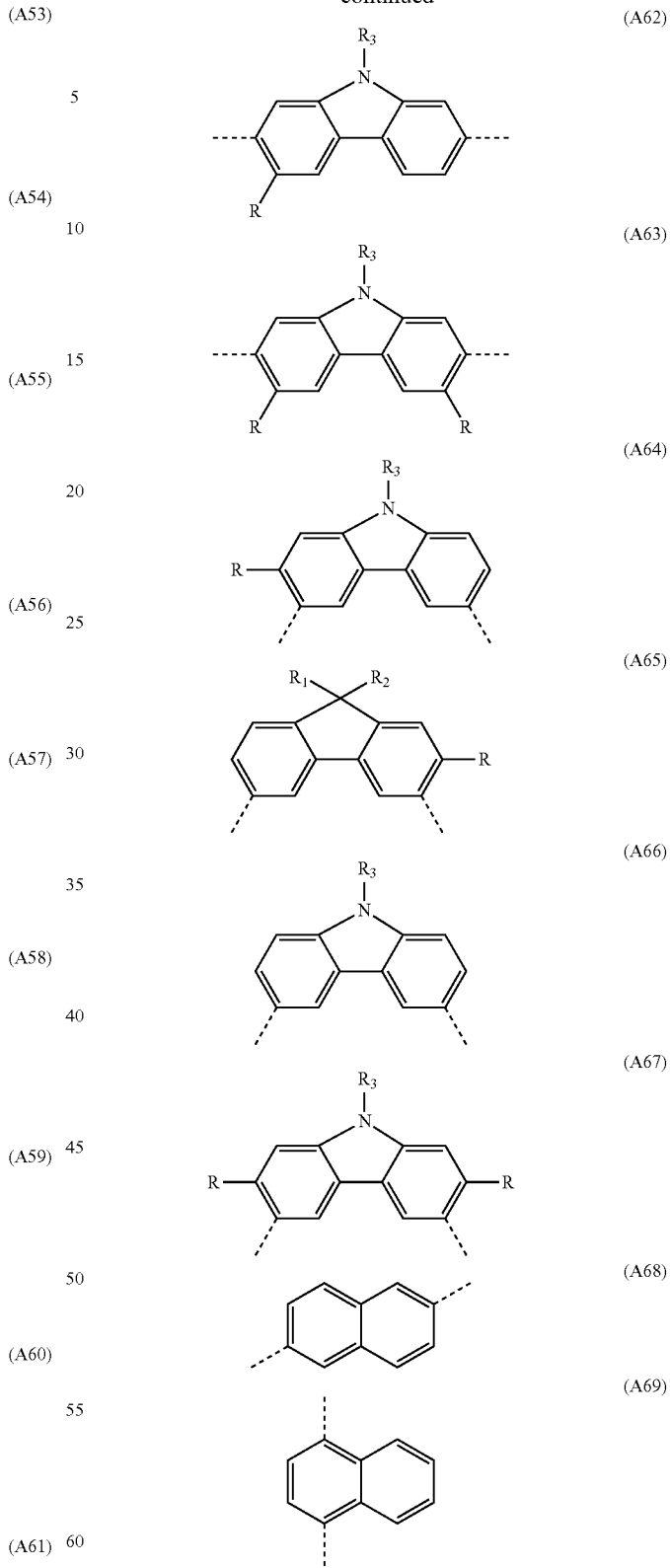
wherein
R=H, R1, R2 or R3;
R1, R2 and R3 are same or independent selected from each other a linear, branched or cyclic alkyl group with 1 to 15 carbon atoms; an alkoxy group with 1 to 15 carbon atoms; an aryl group with 6 to 20 ring-forming carbon atoms; a heteroaryl group with 6 to 20 ring-forming atoms; preferably a linear, branched or cyclic alkyl group with 1 to 10 carbon atoms; an alkoxy group with 1 to 10 carbon atoms; an aryl group with 6 to 15 ring-forming carbon atoms, a heteroaryl group with 6 to 15 ring-forming atoms; further preferred a linear, branched or cyclic alkyl group with 1 to 6 carbon atoms; an alkoxy group with 1 to 5 carbon atoms; an aryl group with 6 to 14 ring-forming carbon atoms; a heteroaryl group with 6 to 14 ring-forming atoms; and more preferred a linear, branched or cyclic alkyl group with 1 to 4 carbon atoms; an alkoxy group with 1 to 2 carbon atoms; an aryl group with 6 to 10 carbon atoms; a heteroaryl group with 6 to 10 ring-forming atoms.

According to another aspect of the second electron transport layer, ET of Formula Ia, Ib and Ic can be selected from a group comprising:

- an unsubstituted aryl group with 13 to 40 ring-forming carbon atoms; or a unsubstituted heteroaryl group with 14 to 40 ring-forming atoms, preferably ET is selected from a group comprising anthrancen-2-yl, anthracen-9yl, pyren-1-yl, pyren-2-yl, phenanthren-9-yl, perylen-2-yl, perylen-3-yl, triphenylen-1-yl, triphenylen-2-yl, benzo[f]tetraphen-4-yl, benzo[e]pyren-4-yl, cyclopenta[cd]fluoranthen-6-yl, benzo[f]tetraphen-0-yl, benzo[e]pyren-3-yl, chrysene-1-yl, rubicen-5-yl, rubicen-6-yl, fluoranthen-3-yl, dibenzo[j,l]fluoranthen-3-yl, dibenzo[j,l]fluoranthen-9-yl, dibenzo[j,l]fluoranthen-10-yl, benzo[k]tetraphen-1-yl, benzo[k]tetraphen-3-yl, benzo[k]tetraphen-4-yl, benzo[k]tetraphen-7-yl, coronen-1-yl, dibenzo[ghi,mno]fluoranthen-1-yl, dinaptho[2,1-b:1',2'-d]furan-6-yl, acridin-9-yl, dibenzo[c,h]acridin-7-yl; or
- a substituted aryl group with 13 to 40 ring-forming carbon atoms; or a substituted heteroaryl group with 14 to 40 ring-forming atoms; preferably ET is selected from a group comprising anthrancen-2-yl, anthracen-9yl, pyren-1-yl, pyren-2-yl, phenanthren-9-yl, perylen-2-yl, perylen-3-yl, dinaptho[2,1-b:1',2'-d]furan-6-yl, acridin-9-yl, dibenzo[c,h]acridin-7-yl, fluoren-2-yl, fluoren-3-yl;

wherein the substituent of the substituted aryl group or heteroaryl group is selected from a group comprising phenyl, 1-naphthyl, 2-naphthyl, 2-biphenyl, 3-biphenyl, 4-biphenyl, 1-pyrenyl, 2-pyrenyl, 2-phenanthrenyl, 9,9'-fluorenyl or 9,9'-xanthenyl According to another aspect of the second electron transport layer, ET of Formula Ia, Ib and Ic can be selected from the group of B1 to B32:

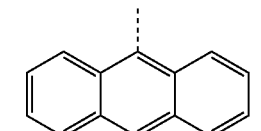
(B1)

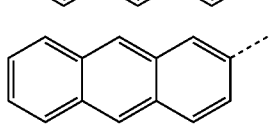
(B2)

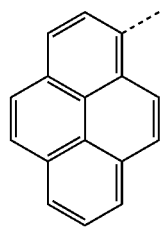
(B3)

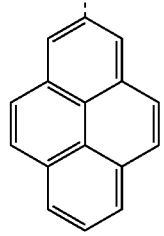
(B4)

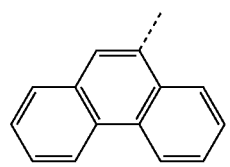
(B5)

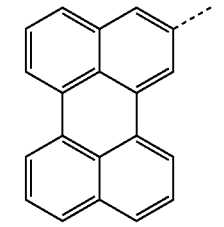
(B6)

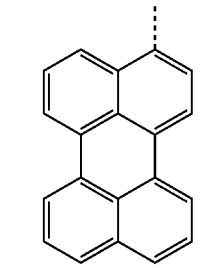
(B7)

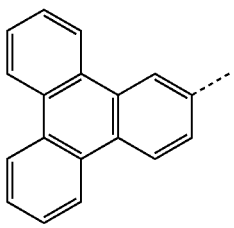
(B8)

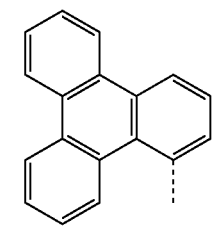
(B9)

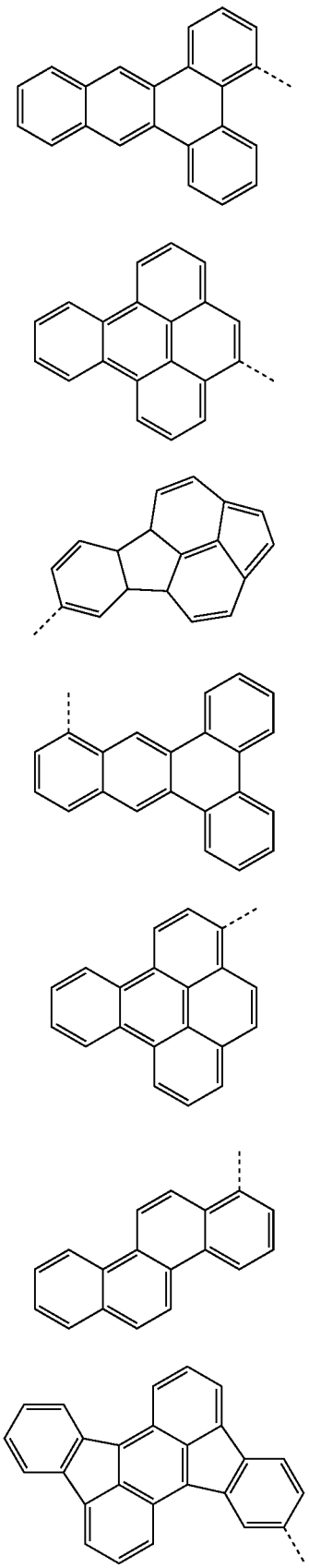
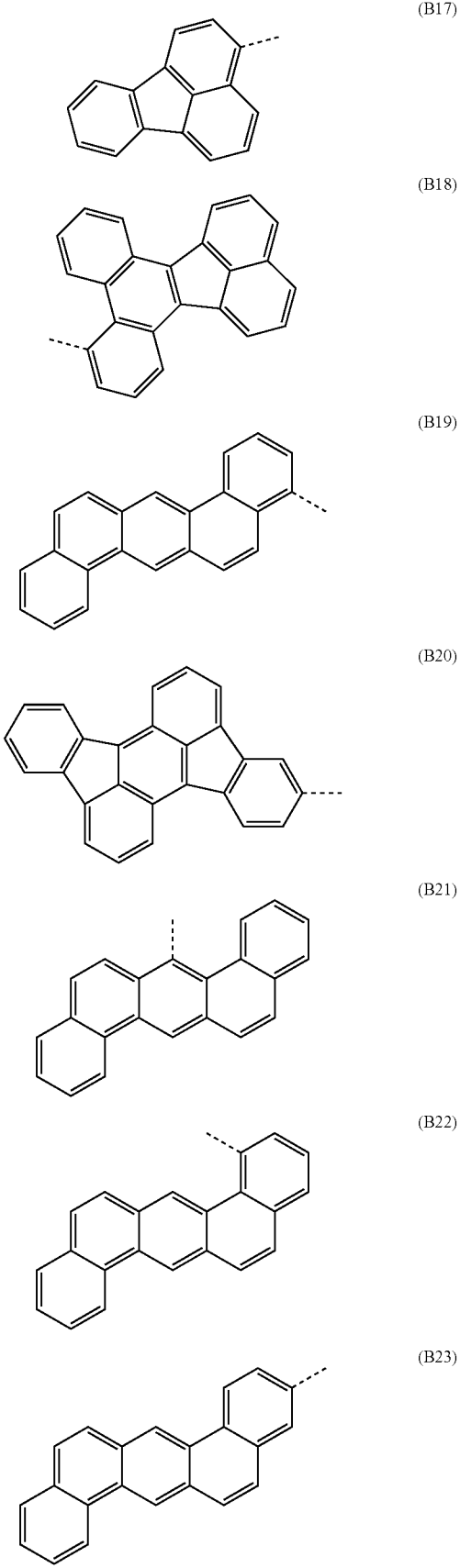

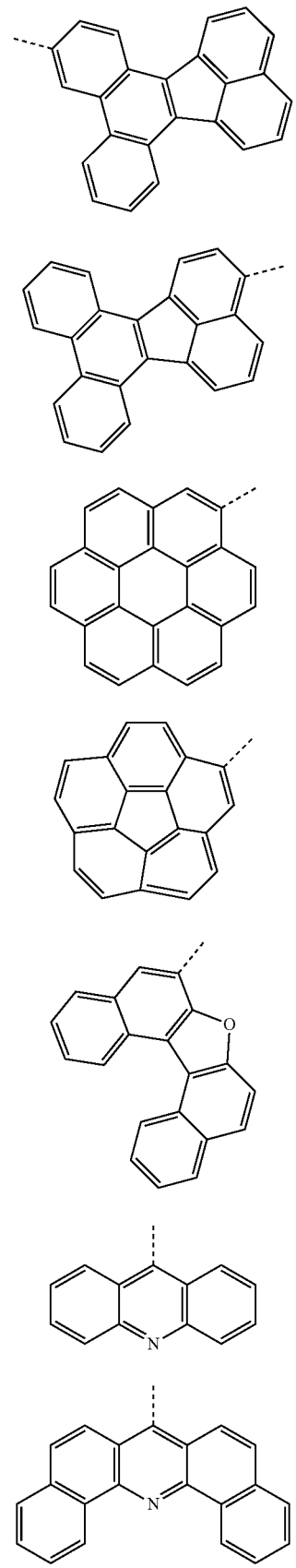

(B24)
(B25)
(B26)
(B27)
(B28)
(B29)
(B30)

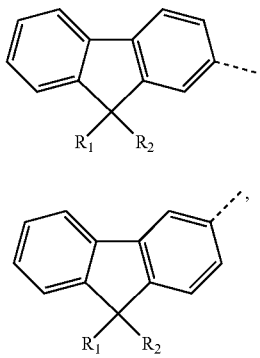

(B31)

(B32)

wherein

R1 and R2 are same or independent selected from each other a linear, branched or cyclic alkyl group with 1 to 15 carbon atoms; an alkoxy group with 1 to 15 carbon atoms; an aryl group with 6 to 20 ring-forming carbon atoms; a heteroaryl group with 6 to 20 ring-forming atoms; preferably a linear, branched or cyclic alkyl group with 1 to 10 carbon atoms; an alkoxy group with 1 to 10 carbon atoms; an aryl group with 6 to 15 ring-forming carbon atoms, a heteroaryl group with 6 to 15 ring-forming atoms; further preferred a linear, branched or cyclic alkyl group with 1 to 6 carbon atoms; an alkoxy group with 1 to 5 carbon atoms; an aryl group with 6 to 14 ring-forming carbon atoms; a heteroaryl group with 6 to 14 ring-forming atoms; and more preferred a linear, branched or cyclic alkyl group with 1 to 4 carbon atoms; an alkoxy group with 1 to 2 carbon atoms; an aryl group with 6 to 10 ring-forming carbon atoms; a heteroaryl group with 6 to 10 ring-forming atoms.

According to another aspect, the ET substituent of formula B1 to B32 can be selected from a phenyl, 1-naphthyl, 2-naphthyl, 2-biphenyl, 3-biphenyl, 4-biphenyl, 1-pyrenyl, 2-pyrenyl, 2-phenanthrenyl, 9,9'-fluorenyl or 9,9'-xanthenyl.

According to another aspect, the second electron transport layer of the OLED comprises at least one matrix material, preferably consist of a matrix material, selected from the group of:

MX 27

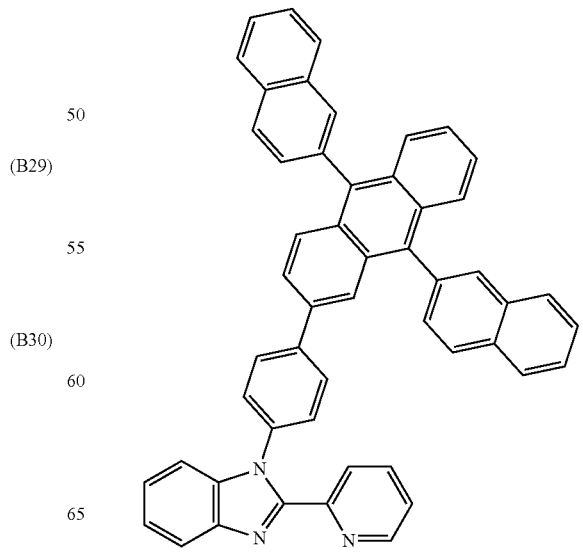

MX 28
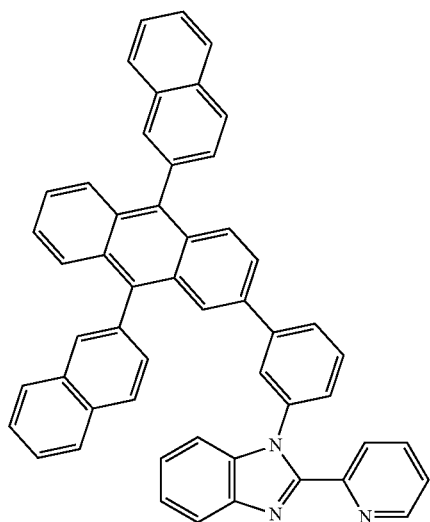
MX 31
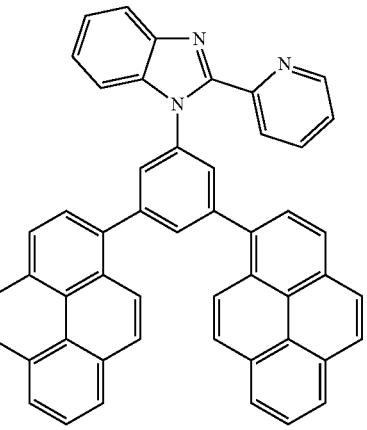
MX 29
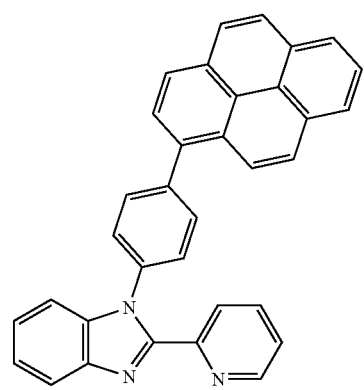
MX 32
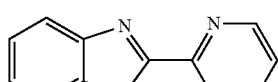
MX 30
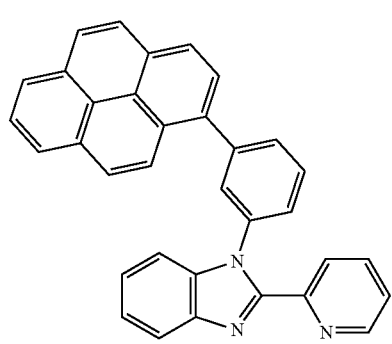
MX 33
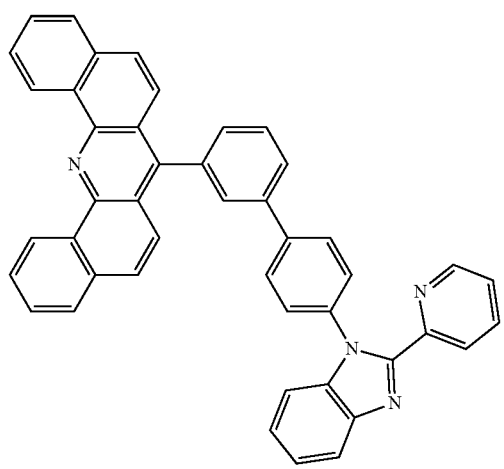

-continued

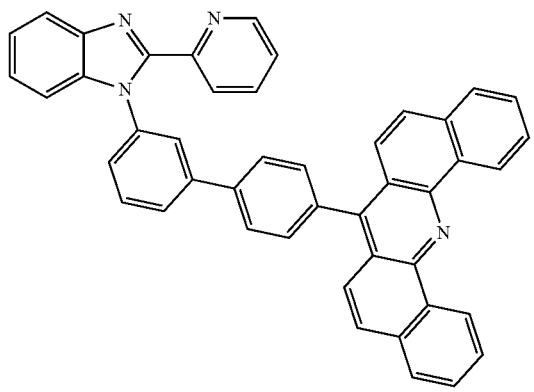

MX 34

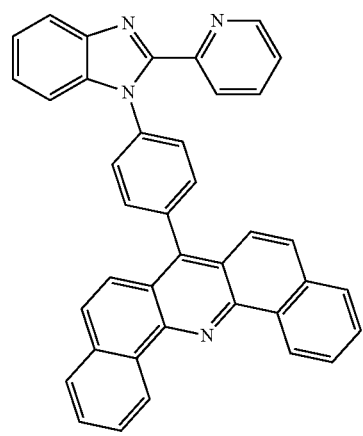

MX 35

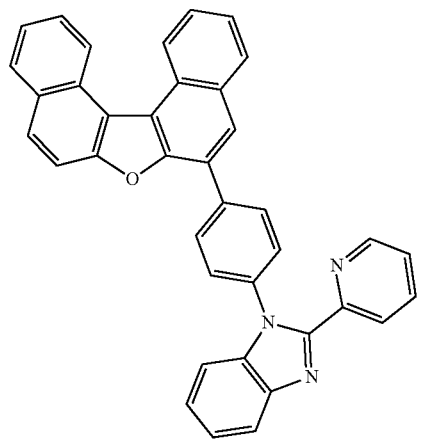

MX 36

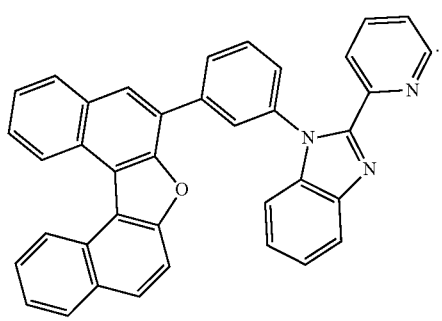

MX 37

According to another aspect the OLED may comprises
a first electron transport layer comprising a matrix material selected from the group 3-(dibenzo[c,h]acridin-7-yl)phenyl)diphenylphosphine oxide, phenylbis(3-(pyren-1-yl)phenyl)phosphine oxide, 3-phenyl-3H-benzo[b]dinaphtho[2,1-d:1',2'-f]phosphepine-3-oxide, (3'-(dibenzo[c,h]acridin-7-yl)-[1,1'-biphenyl]4-yl)diphenylphosphine oxide, (3-(10-(naphthalen-2-yl)anthracen-9-yl)phenyl)diphenylphosphine oxide and/or 2-(4-(9,10-di(naphthalen-2-yl)anthracen-2-yl)phenyl)-1-phenyl-1H-benzo[d]imidazole;

the second electron transport layer (162) comprises a matrix material having the formula Ia, Ib and/or Ic;

the optional third electron transport layer (163) comprises a matrix material selected from the group comprising 2-(4-(9,10-di(naphthalen-2-yl)anthracen-2-yl)phenyl)-1-phenyl-1H-benzo[d]imidazole, 3-(dibenzo[c,h]acridin-7-yl)phenyl)diphenylphosphine oxide, phenylbis(3-(pyren-1-yl)phenyl)phosphine oxide, (3'-(dibenzo[c,h]acridin-7-yl)-[1,1'-biphenyl]-4-yl)
diphenylphosphine oxide, (3-(10-(naphthalen-2-yl)anthracen-9-yl)phenyl)diphenylphosphine oxide and/or 3-phenyl-3H-benzo[b]dinaphtho[2,1-d:1',2'-f]phosphepine-3-oxide;

whereby the matrix material of the second electron transport layer is selected different to the matrix material of the first electron transport layer and the optional third electron transport layer.

According to another aspect the OLED may comprises
a first electron transport layer comprising a matrix material selected from the group 3-(dibenzo[c,h]acridin-7-yl)phenyl)diphenylphosphine oxide, phenylbis(3-(pyren-1-yl)phenyl)phosphine oxide, 3-phenyl-3H-benzo[b]dinaphtho[2,1-d:1',2'-f]phosphepine-3-oxide, (3'-(dibenzo[c,h]acridin-7-yl)-[1,1'-biphenyl]-4-yl)diphenylphosphine oxide, (3-(10-(naphthalen-2-yl)anthracen-9-yl)phenyl)diphenylphosphine oxide and/or 2-(4-(9,10-di(naphthalen-2-yl)anthracen-2-yl)phenyl)-1-phenyl-1H-benzo[d]imidazole;

a second electron transport layer comprising a matrix material selected from the group of:

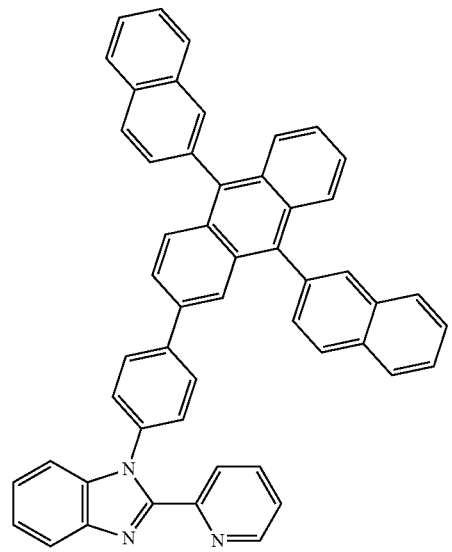

MX 27

MX 28
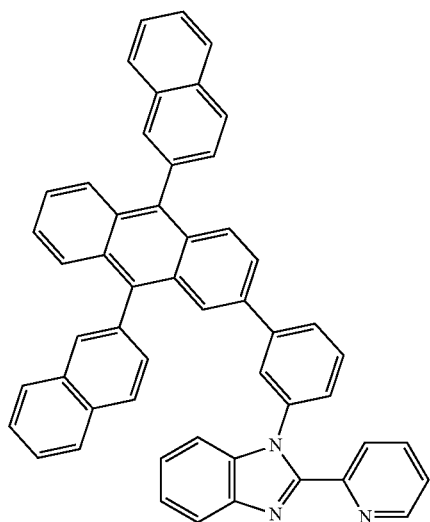
MX 29
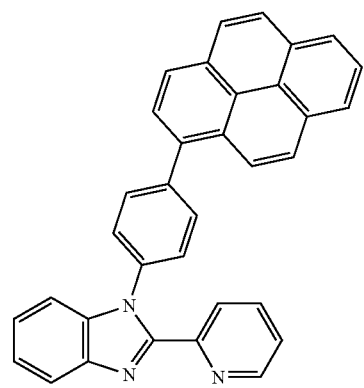
MX 30
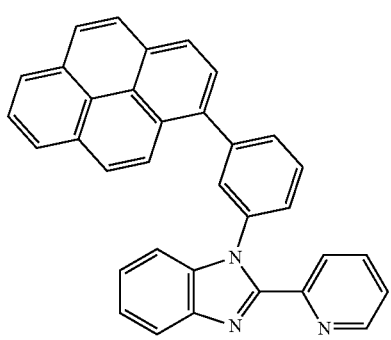
MX 31
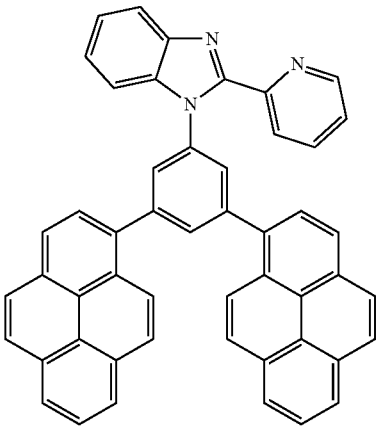
MX 32
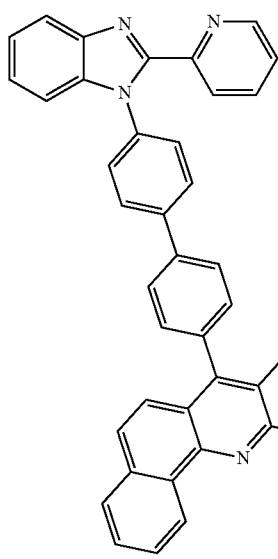
MX 33
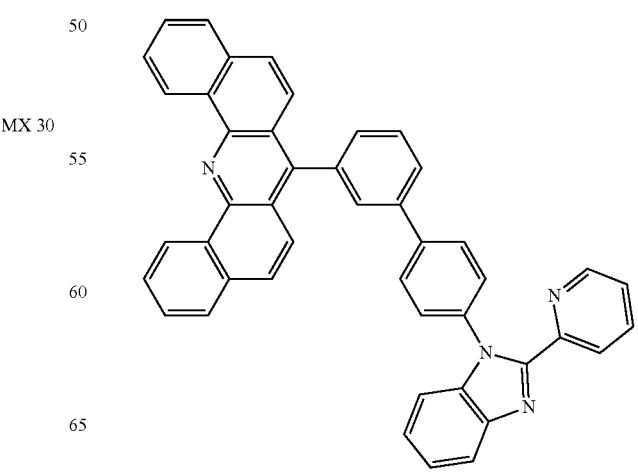

MX 34

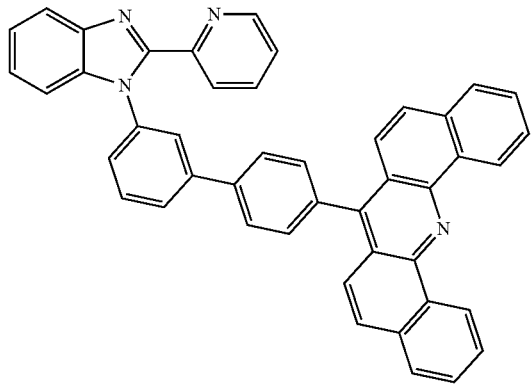

MX 35

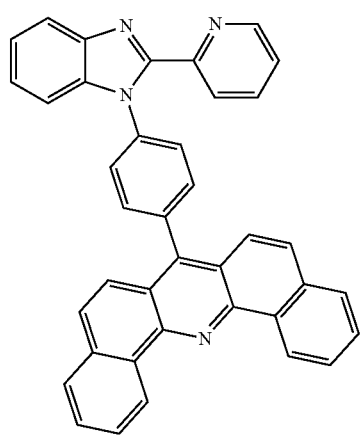

MX 36

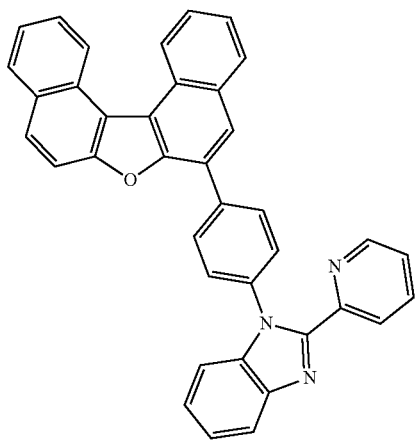

MX 37

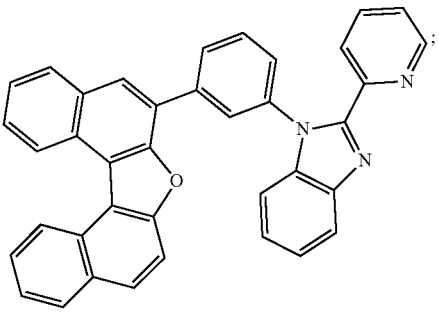

the optional third electron transport layer comprises a matrix material selected from the group comprising 2-(4-(9,10-di(naphthalen-2-yl)anthracen-2-yl)phenyl)-1-phenyl-1H-benzo[d]imidazole, 3-(dibenzo[c,h]acridin-7-yl)phenyl)diphenylphosphine oxide, phenylbis(3-(pyren-1-yl)phenyl)phosphine oxide, (3'-(dibenzo[c,h]acridin-7-yl)-[1,1'-biphenyl]-4-yl) diphenylphosphine oxide, (3-(10-(naphthalen-2-yl)anthracen-9-yl)phenyl)diphenylphosphine oxide and/or 3-phenyl-3H-benzo[b]dinaphtho[2,1-d:1',2'-f]phosphepine-3-oxide; whereby the matrix material of the second electron transport layer is selected different to the matrix material of the first electron transport layer and the optional third electron transport layer.

According to another aspect the matrix compound of the first electron transport layer or of the first and third electron transport layer can be (3-(dibenzo[c,h]acridin-7-yl)phenyl)diphenylphosphine oxide or (3'-(dibenzo[c,h]acridin-7-yl)-[1,1'-biphenyl]-4-yl)diphenylphosphine oxide and the matrix compound of the second electron transport layer can be 4,7-diphenyl-2,9-di-p-tolyl-1,10-phenanthroline and/or 4-(naphthalen-1-yl)-2,7,9-triphenylpyrido[3,2-h]quinazoline and/or 4,4'-bis(4,6-diphenyl-1,3,5-triazin-2-yl)biphenyl and/or 3-phenyl-3H-benzo[b]dinaphtho[2,1-d:1',2'-f]phosphepine-3-oxide.

According to another aspect the first and third electron transport layer may consist of one matrix compound and one dopant and the second electron transport layer may consist of one matrix compound according to formula Ia, Ib and/or Ic.

According to another aspect the first electron transport layer may consist of one matrix compound and one dopant and the second electron transport layer may consist of one matrix compound according to formula Ia, Ib and/or Ic.

According to another aspect the second electron transport layer may consist of one matrix compound according to formula Ia, Ib and/or Ic.

Matrix compounds that can be suitable used for the electron transport layer, except the second transport layer, are summarized in Table 2 below.

TABLE 2

Chemical structures of matrix compounds that can be suitable used, except for the second electron transfer layer.

| Compound | Name | Structure | Reference |
| --- | --- | --- | --- |
| MX 1 | 2-(4-(9,10-di(naphthalen-2-yl)anthracen-2-yl)phenyl)-1-phenyl-1H-benzo[d]imidazole | 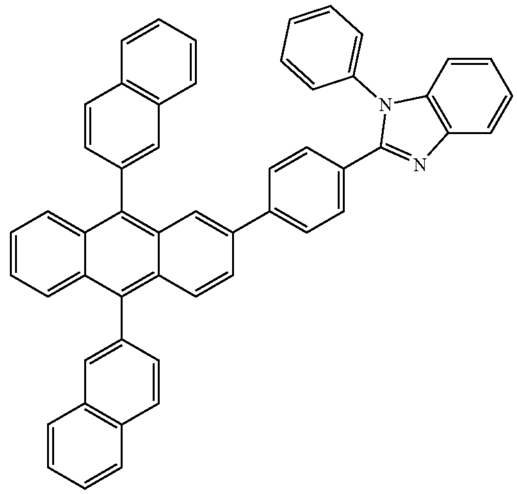 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | U.S. Pat. No. 6,878,469 |
| MX 2 | 9,10-di(2-naphthyl)anthracene | 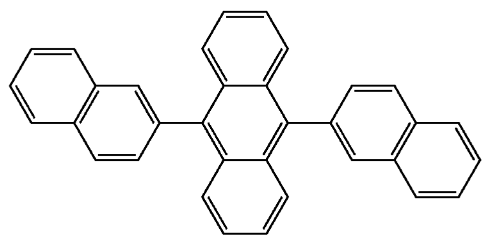 [SMILES: c1ccc2cc(-c3c4ccccc4c(-c4ccc5ccccc5c4)c4ccccc34)ccc2c1] | U.S. Pat. No. 5,935,721 |
| MX 3 | 3-[3'-(10-phenyl-9-anthracenyl)[1,1'-biphenyl]-4-yl]-quinoline | 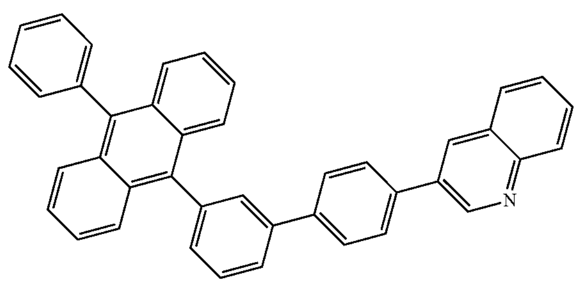 [SMILES: c1ccc(-c2c3ccccc3c(-c3cccc(-c4ccc(-c5cnc6ccccc6c5)cc4)c3)c3ccccc23)cc1] | KR2011018195 |
| MX 4 | 1-(4-(10-([1,1'-biphenyl]-4-yl)anthracen-9-yl)phenyl)-2-ethyl-1H-benzo[d]imidazole | 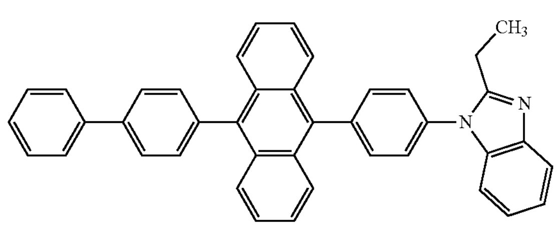 [SMILES: CCc1nc2ccccc2n1-c1ccc(-c2c3ccccc3c(-c3ccc(-c4ccccc4)cc3)c3ccccc23)cc1] | WO2010134352 |

TABLE 2-continued
Chemical structures of matrix compounds that can be suitable used, except for the second electron transfer layer.
| Compound | Name | Structure | Reference |
|---|---|---|---|
| MX 5 | (3-(9,10-di(naphthalen-2-yl)anthracen-2-yl)phenyl)diphenylphosphine oxide | 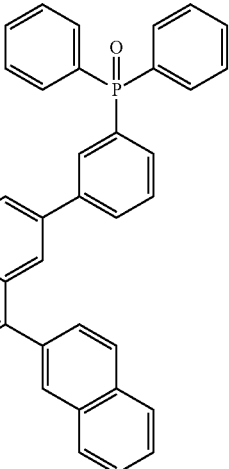 | EP13187905.8 |
| MX 6 | bis(4-(anthracen-9-yl)phenyl)(phenyl)phosphine oxide | 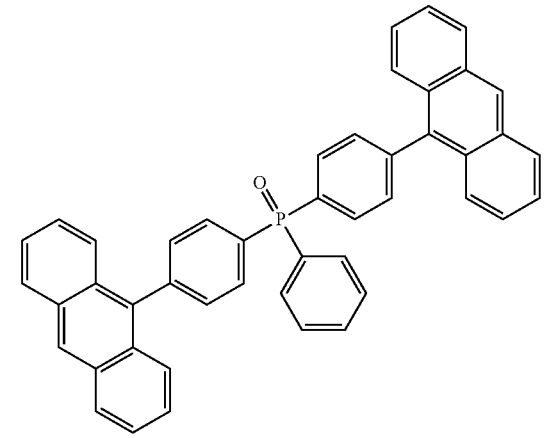 [SMILES: O=P(c1ccccc1)(c1ccc(-c2c3ccccc3cc3ccccc23)cc1)c1ccc(-c2c3ccccc3cc3ccccc23)cc1] | EP13187905.8 |
| MX 7 | Phenyldi(pyren-1-yl)phosphine oxide | 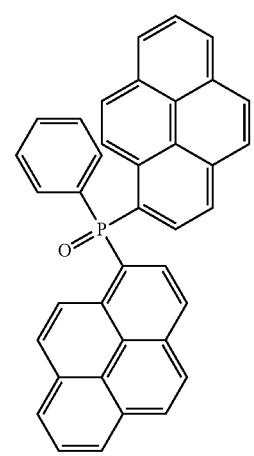 [SMILES: O=P(c1ccccc1)(c1ccc2ccc3cccc4ccc1c2c34)c1ccc2ccc3cccc4ccc1c2c34] | JP4876333 |

TABLE 2-continued

Chemical structures of matrix compounds that can be suitable used, except for the second electron transfer layer.

| Compound | Name | Structure | Reference |
|---|---|---|---|
| MX 8 | Phenylbis(3-(pyren-1-yl)phenyl)phosphine oxide | 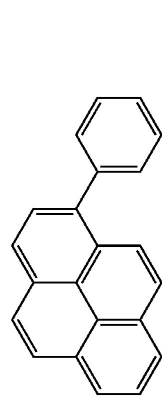 | EP13187905.8 |
| MX 9 | diphenyl(4'-(pyren-1-yl)-[1,1'-biphenyl]-3-yl)phosphine oxide | 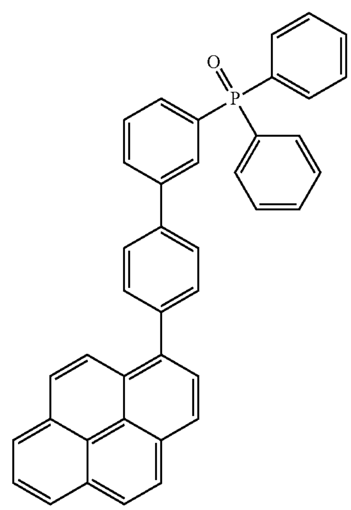 [SMILES: O=P(c1ccccc1)(c1ccccc1)c1cccc(-c2ccc(-c3ccc4ccc5cccc6ccc3c4c56)cc2)c1] | EP13187905.8 |
| MX 10 | diphenyl(5-(pyren-1-yl)pyridin-2-yl)phosphine oxide | 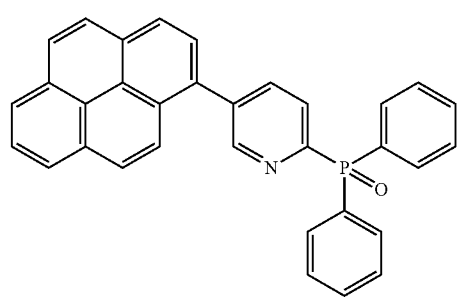 [SMILES: O=P(c1ccccc1)(c1ccccc1)c1ccc(-c2ccc3ccc4cccc5ccc2c3c45)cn1] | WO2014167020 |

TABLE 2-continued

Chemical structures of matrix compounds that can be suitable used, except for the second electron transfer layer.

| Compound | Name | Structure | Reference |
|---|---|---|---|
| MX 11 | (3-(dibenzo[c,h]acridin-7-yl)phenyl)diphenylphosphine oxide | 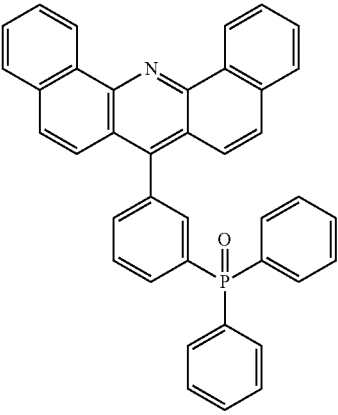 [SMILES: O=P(c1ccccc1)(c1ccccc1)c1cccc(-c2c3ccc4ccccc4c3nc3c2ccc2ccccc23)c1] | EP 2395571, WO2013079217 |
| MX 12 | 3-Phenyl-3H-benzo[b]dinaphtho[2,1-d:1',2'-f]phosphepine-3-oxide | 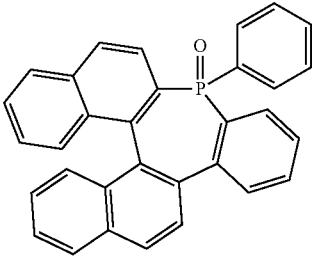 [SMILES: O=P1(c2ccccc2)c2ccccc2-c2ccc3ccccc3c2-c2c1ccc1ccccc21] | EP13199361.0 |
| MX 13 | 2,4,7,9-tetraphenyl-1,10-phenanthroline | 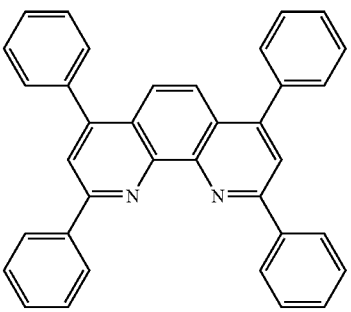 [SMILES: c1ccc(-c2cc(-c3ccccc3)c3ccc4c(-c5ccccc5)cc(-c5ccccc5)nc4c3n2)cc1] | EP1786050 |
| MX 14 | 4,7-diphenyl-2,9-di-p-tolyl-1,10-phenanthroline | 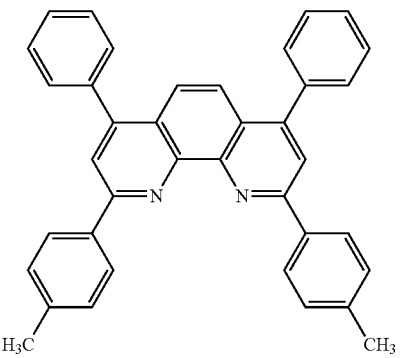 [SMILES: Cc1ccc(-c2cc(-c3ccccc3)c3ccc4c(-c5ccccc5)cc(-c5ccc(C)cc5)nc4c3n2)cc1] | EP1786050 |

TABLE 2-continued

Chemical structures of matrix compounds that can be suitable used, except for the second electron transfer layer.

| Compound | Name | Structure | Reference |
|---|---|---|---|
| MX 15 | 2,9-di(biphenyl-4-yl)-4,7-diphenyl-1,10-phenanthroline | 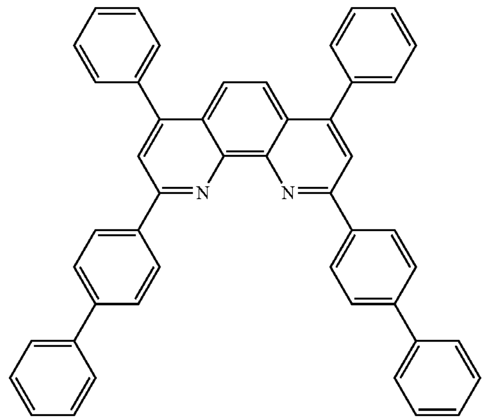 [SMILES: c1ccc(-c2ccc(-c3cc(-c4ccccc4)c4ccc5c(-c6ccccc6)cc(-c6ccc(-c7ccccc7)cc6)nc5c4n3)cc2)cc1] | EP1786050 |
| MX 16 | 3,8-bis(6-phenyl-2-pyridinyl)-1,10-phenanthroline | 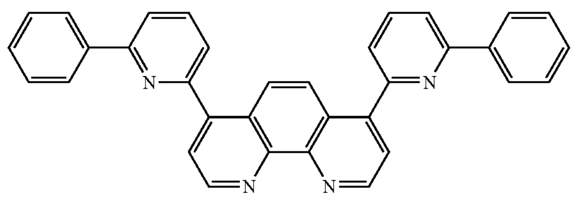 [SMILES: c1ccc(-c2cccc(-c3ccnc4c3ccc3c(-c5cccc(-c6ccccc6)n5)ccnc34)n2)cc1] | CN102372708 |
| MX 17 | 9-phenyl-9'-(4-phenyl-2-quinazolinyl)-3,3'-bi-9H-carbazole | 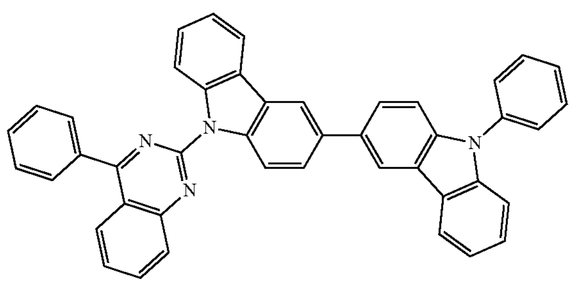 [SMILES: c1ccc(-c2nc(-n3c4ccccc4c4cc(-c5ccc6c(c5)c5ccccc5n6-c5ccccc5)ccc43)nc3ccccc23)cc1] | KR2012102374 |
| MX 18 | 4-(2-naphthalenyl)-2-[4-(3-quinolinyl)phenyl]-benzo[h]quinazoline | 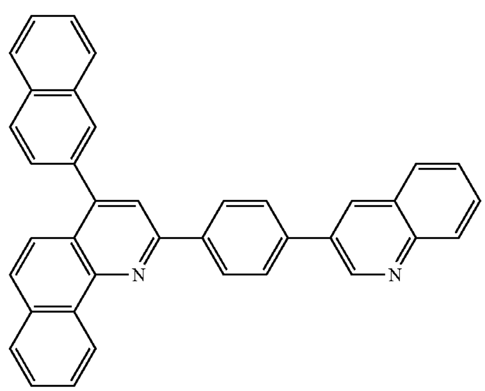 [SMILES: c1ccc2cc(-c3cc(-c4ccc(-c5cnc6ccccc6c5)cc4)nc4c3ccc3ccccc34)ccc2c1] | KR2014076522 |

TABLE 2-continued

Chemical structures of matrix compounds that can be suitable used, except for the second electron transfer layer.

| Compound | Name | Structure | Reference |
|---|---|---|---|
| MX 19 | 4-(naphthalen-1-yl)-2,7,9-triphenylpyrido[3,2-h]quinazoline | 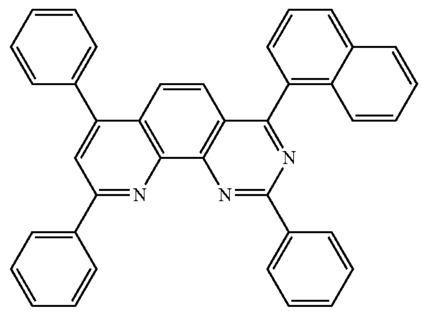 [SMILES: c1ccc(-c2cc(-c3ccccc3)c3ccc4c(-c5cccc6ccccc56)nc(-c5ccccc5)nc4c3n2)cc1] | EP1970371 |
| MX 20 | 4,4'-bis(4,6-diphenyl-1,3,5-triazine-2-yl)biphenyl | 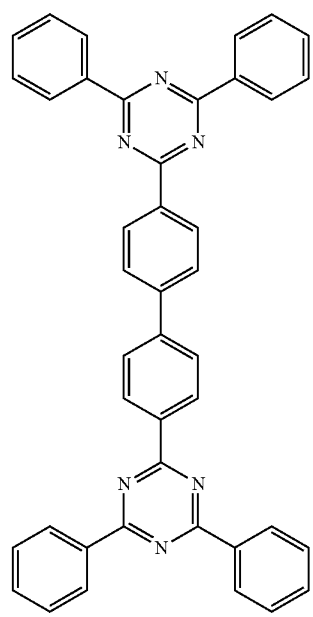 [SMILES: c1ccc(-c2nc(-c3ccccc3)nc(-c3ccc(-c4ccc(-c5nc(-c6ccccc6)nc(-c6ccccc6)n5)cc4)cc3)n2)cc1] | U.S. Pat. No. 6,225,467 |
| MX 21 | 3-[4-(4,6-di-2-naphthalenyl-1,3,5-triazin-2-yl)phenyl]-quinoline | 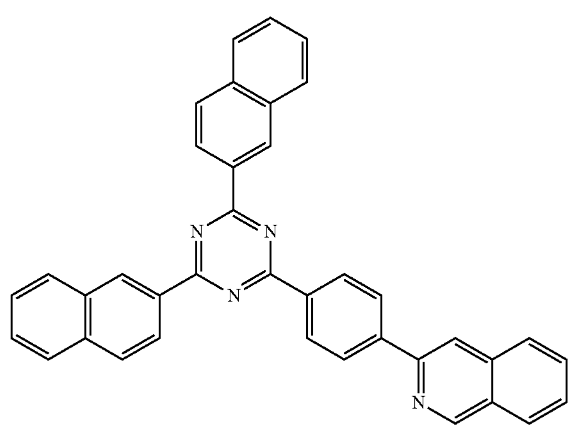 [SMILES: c1ccc2cc(-c3nc(-c4ccc(-c5cc6ccccc6cn5)cc4)nc(-c4ccc5ccccc5c4)n3)ccc2c1] | US20110156013 |

TABLE 2-continued

Chemical structures of matrix compounds that can be suitable used, except for the second electron transfer layer.

| Compound | Name | Structure | Reference |
|---|---|---|---|
| MX 22 | 2-[3-(6'-methyl[2,2'-bipyridin]-5-yl)-5-(9-phenanthrenyl)phenyl]-4,6-diphenyl-1,3,5-triazine | 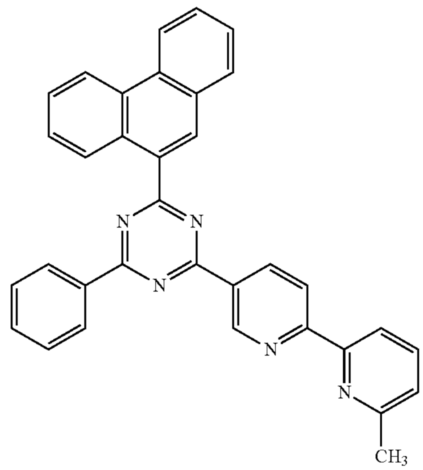 [SMILES: Cc1cccc(-c2ccc(-c3nc(-c4ccccc4)nc(-c4cc5ccccc5c5ccccc45)n3)cn2)n1] | WO2014171541 |
| MX 23 | diphenyl(4-(pyren-1-yl)phenyl)phosphine oxide | 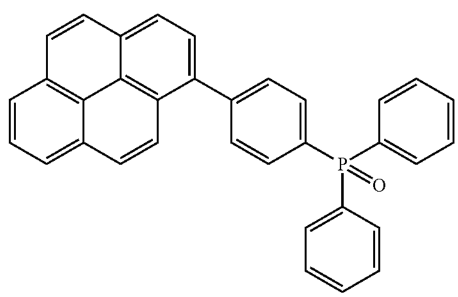 [SMILES: O=P(c1ccccc1)(c1ccccc1)c1ccc(-c2ccc3ccc4cccc5ccc2c3c45)cc1] | EP13187905.8 |
| MX 24 | 7-(naphthalen-2-yl)dibenzo[c,h]acridine | 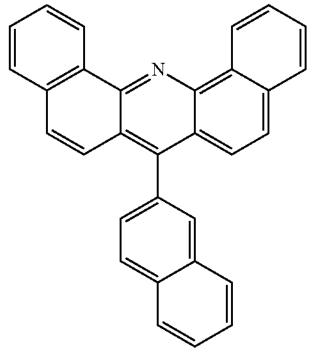 [SMILES: c1ccc2cc(-c3c4ccc5ccccc5c4nc4c3ccc3ccccc34)ccc2c1] | EP 2395571 |

TABLE 2-continued

Chemical structures of matrix compounds that can be suitable used, except for the second electron transfer layer.

| Compound | Name | Structure | Reference |
|---|---|---|---|
| MX 25 | (3'-(dibenzo[c,h]acridin-7-yl)-[1,1'-biphenyl]-4-yl)diphenylphosphine oxide | 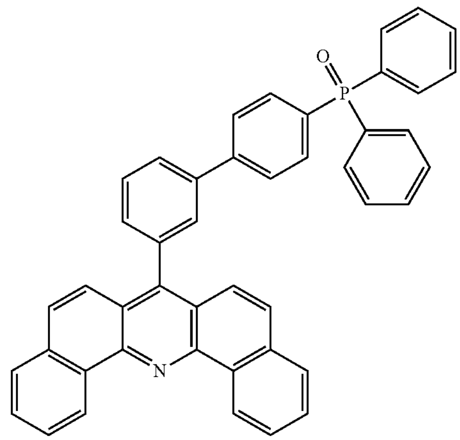 [SMILES: O=P(c1ccccc1)(c1ccccc1)c1ccc(-c2cccc(-c3c4ccc5ccccc5c4nc4c3ccc3ccccc34)c2)cc1] | WO2011154131 A1 and WO2013079217 A1 |
| MX 26 | (3-(10-(naphthalen-2-yl)anthracen-9-yl)phenyl)diphenylphosphine oxide | 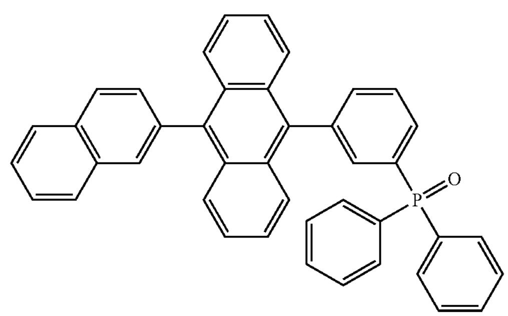 [SMILES: O=P(c1ccccc1)(c1ccccc1)c1cccc(-c2c3ccccc3c(-c3ccc4ccccc4c3)c3ccccc23)c1] | PCT/EP2014/071659 |

As can be seen in the Table 3 below, the position of the nitrogen atom in the pyridinyl moiety has no impact on the LUMO level. Instead, the LUMO level is dominated by the electron transport moiety ET. Therefore, the compounds for formula Ia, Ib, and Ic can be suitably used in the second electron transport layer:

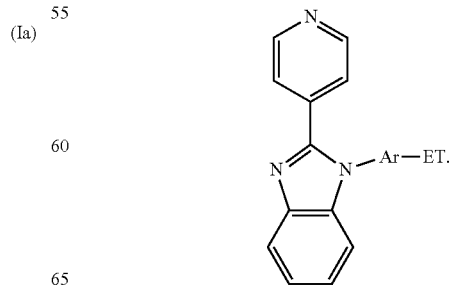

TABLE 3
| Formula | Chemical structure | calc. HOMO [eV] | calc. LUMO[eV] | calc. Optical bandgap [eV] |
|---|---|---|---|---|
| Ia | 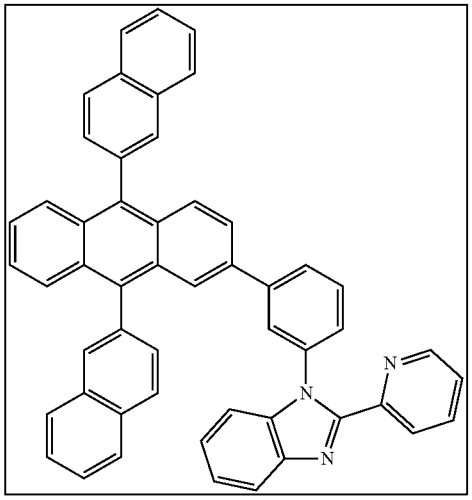 [SMILES: c1ccc(-c2nc3ccccc3n2-c2cccc(-c3ccc4c(-c5ccc6ccccc6c5)c5ccccc5c(-c5ccc6ccccc6c5)c4c3)c2)nc1] | −4.97 | −2.89 | −2.08 |
| Ib | 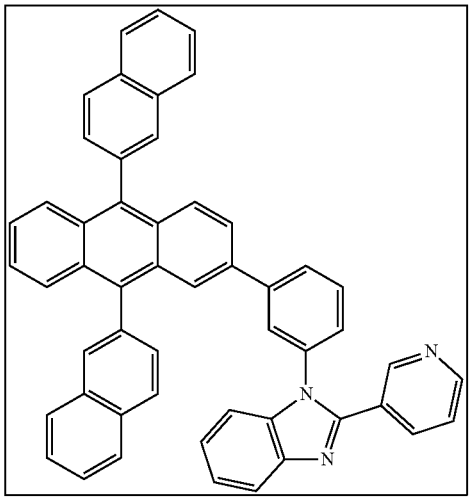 [SMILES: c1cncc(-c2nc3ccccc3n2-c2cccc(-c3ccc4c(-c5ccc6ccccc6c5)c5ccccc5c(-c5ccc6ccccc6c5)c4c3)c2)c1] | −4.99 | −2.90 | −2.09 |
| Ic | 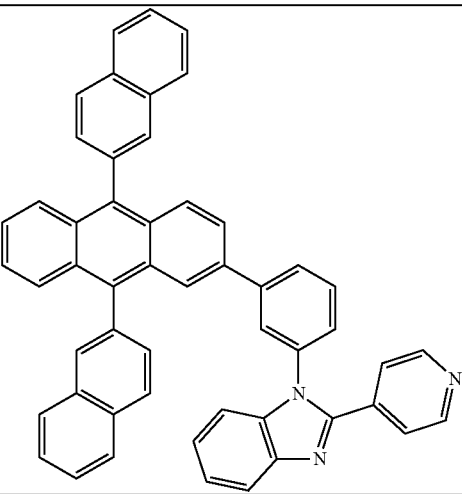 | −5.05 | −2.96 | 2.09 |

Matrix compounds that can be suitable used for the second electron transport layer, are summarized in Table 4 below.

TABLE 4

Matrix compounds which can be suitably used in the second electron transport layer

| Compound | IUPAC name | Structure |
|---|---|---|
| MX 27 | 1-(4-(9,10-di(naphthalen-2-yl)anthracen-2-yl)phenyl)-2-(pyridin-2-yl)-1H-benzo[d]imidazole | 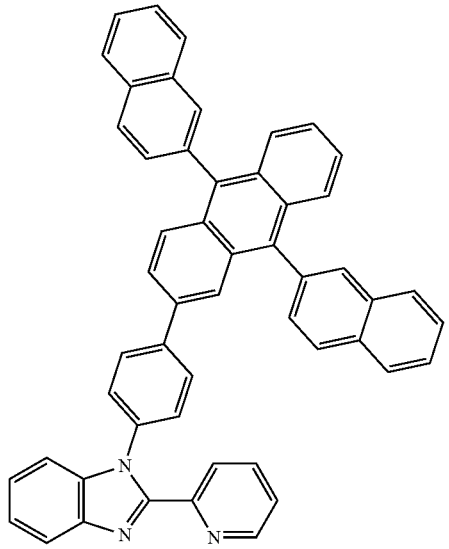 [SMILES: c1ccc(-c2nc3ccccc3n2-c2ccc(-c3ccc4c(-c5ccc6ccccc6c5)c5ccccc5c(-c5ccc6ccccc6c5)c4c3)cc2)nc1] |
| MX 28 | 1-(3-(9,10-di(naphthalen-2-yl)anthracen-2-yl)phenyl)-2-(pyridin-2-yl)-1H-benzo[d]imidazole | 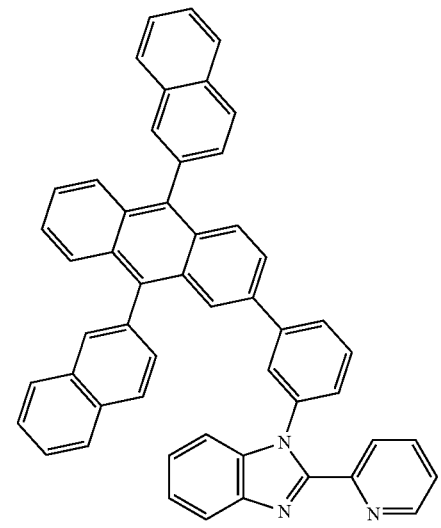 [SMILES: c1ccc(-c2nc3ccccc3n2-c2cccc(-c3ccc4c(-c5ccc6ccccc6c5)c5ccccc5c(-c5ccc6ccccc6c5)c4c3)c2)nc1] |
| MX 29 | 1-(4-(pyren-1-yl)phenyl)-2-(pyridin-2-yl)-1H-benzo[d]imidazole | 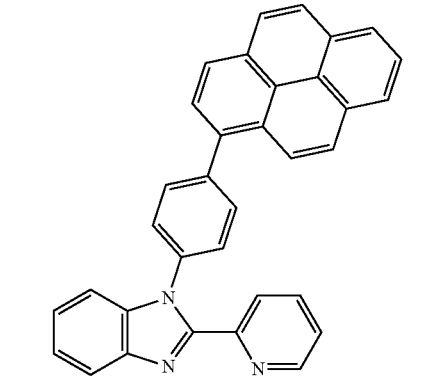 [SMILES: c1ccc(-c2nc3ccccc3n2-c2ccc(-c3ccc4ccc5cccc6ccc3c4c56)cc2)nc1] |

TABLE 4-continued

Matrix compounds which can be suitably used in the second electron transport layer

| Compound | IUPAC name | Structure |
|---|---|---|
| MX 30 | 1-(3-(pyren-1-yl)phenyl)-2-(pyridin-2-yl)-1H-benzo[d]imidazole | 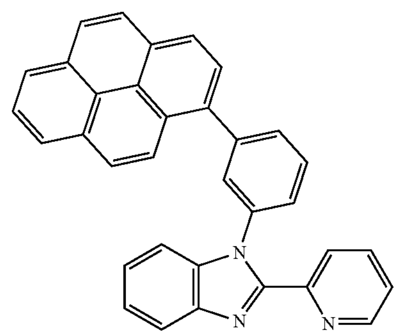 [SMILES: c1ccc(-c2nc3ccccc3n2-c2cccc(-c3ccc4ccc5cccc6ccc3c4c56)c2)nc1] |
| MX 31 | 1-(3,5-di(pyren-1-yl)phenyl)-2-(pyridin-2-yl)-1H-benzo[d]imidazole | 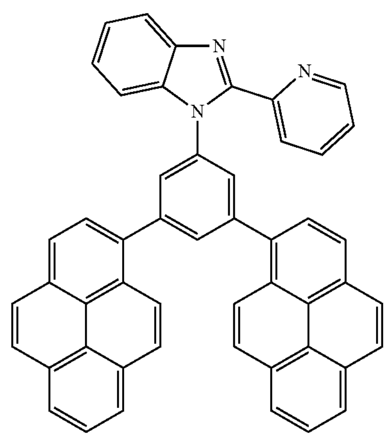 [SMILES: c1ccc(-c2nc3ccccc3n2-c2cc(-c3ccc4ccc5cccc6ccc3c4c56)cc(-c3ccc4ccc5cccc6ccc3c4c56)c2)nc1] |
| MX 32 | 7-(4'-(2-(pyridin-2-yl)-1H-benzo[d]imidazol-1-yl)-[1,1'-biphenyl]-4-yl)dibenzo[c,h]acridine | 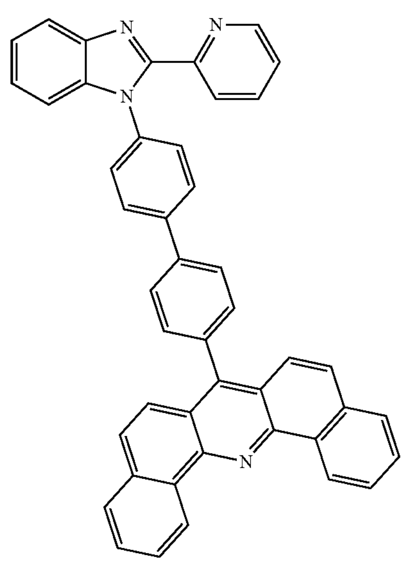 [SMILES: c1ccc(-c2nc3ccccc3n2-c2ccc(-c3ccc(-c4c5ccc6ccccc6c5nc5c4ccc4ccccc45)cc3)cc2)nc1] |

TABLE 4-continued
Matrix compounds which can be suitably used in the second electron transport layer
| Compound | IUPAC name | Structure |
|---|---|---|
| MX 33 | 7-(4'-(2-(pyridin-2-yl)-1H-benzo[d]imidazol-1-yl)-[1,1'-biphenyl]-3-yl)dibenzo[c,h]acridine | 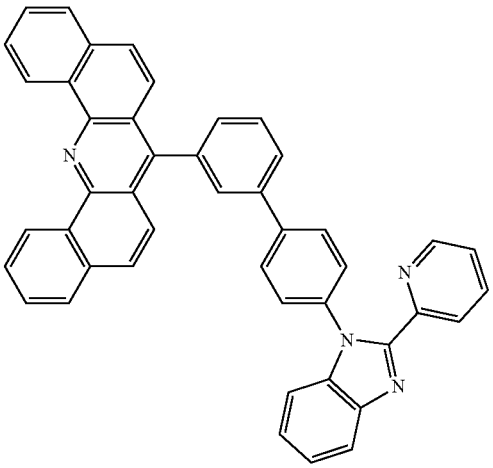 [SMILES: c1ccc(-c2nc3ccccc3n2-c2ccc(-c3cccc(-c4c5ccc6ccccc6c5nc5c4ccc4ccccc45)c3)cc2)nc1] |
| MX 34 | 7-(3'-(2-(pyridin-2-yl)-1H-benzo[d]imidazol-1-yl)-[1,1'-biphenyl]-4-yl)dibenzo[c,h]acridine | 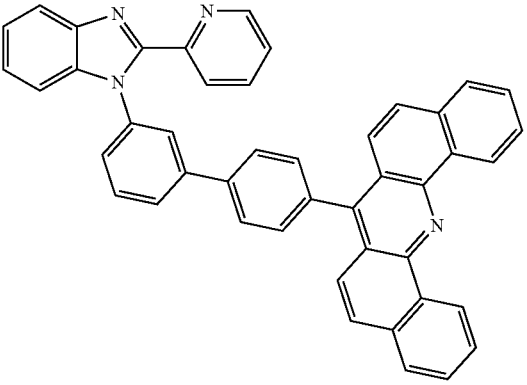 [SMILES: c1ccc(-c2nc3ccccc3n2-c2cccc(-c3ccc(-c4c5ccc6ccccc6c5nc5c4ccc4ccccc45)cc3)c2)nc1] |
| MX 35 | 7-(4-(2-(pyridin-2-yl)-1H-benzo[d]imidazol-1-yl)phenyl)dibenzo[c,h]acridine | 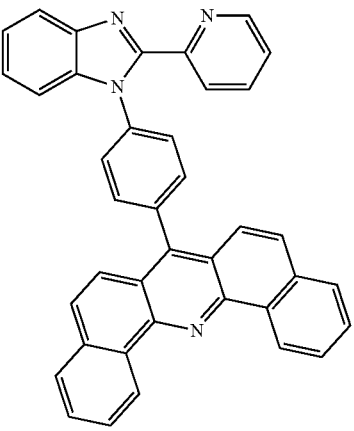 [SMILES: c1ccc(-c2nc3ccccc3n2-c2ccc(-c3c4ccc5ccccc5c4nc4c3ccc3ccccc34)cc2)nc1] |

TABLE 4-continued

Matrix compounds which can be suitably used in the second electron transport layer

| Compound | IUPAC name | Structure |
|---|---|---|
| MX 36 | 1-(4-(dinaphtho[2,1-b:1',2'-d]furan-6-yl)phenyl)-2-(pyridin-2-yl)-1H-benzo[d]imidazole | 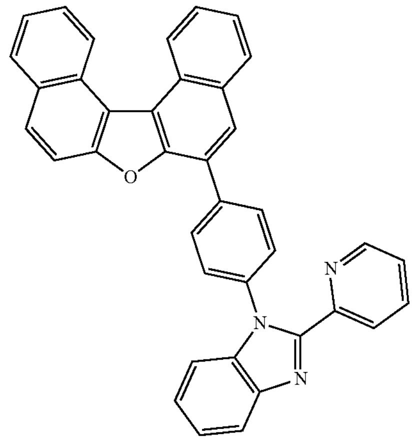 [SMILES: c1ccc(-c2nc3ccccc3n2-c2ccc(-c3cc4ccccc4c4c3oc3ccc5ccccc5c34)cc2)nc1] |
| MX 37 | 1-(3-(dinaphtho[2,1-b:1',2-d]furan-6-yl)phenyl)-2-(pyridin-2-yl)-1H-benzo[d]imidazole | 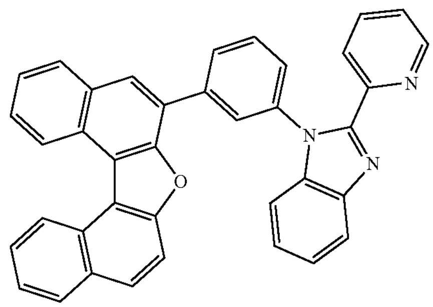 [SMILES: c1ccc(-c2nc3ccccc3n2-c2cccc(-c3cc4ccccc4c4c3oc3ccc5ccccc5c34)c2)nc1] |

According to various embodiments of the organic light-emitting diode, wherein
the first electron transport layer comprises about ≤90 wt.-% to about ≥30 wt.-%, of a matrix compound; or
the first electron transport layer and the third electron transport layer comprises each about ≤90 wt.-% to about ≥30 wt.-%, of a matrix compound;
wherein the weight percent of the matrix compound is based on the total weight of the corresponding transport layer.

According to various embodiments of the organic light-emitting diode, wherein
the first electron transport layer may comprise about ≤80 wt.-% to about ≥35 wt.-% of a matrix compound; or
the first electron transport layer and the third electron transport layer comprises each about ≤80 wt.-% to about ≥35 wt.-% of a matrix compound;
wherein the weight percent of the matrix compound is based on the total weight of the corresponding transport layer.

According to various embodiments of the organic light-emitting diode, wherein
the first electron transport layer may comprise about ≤50 wt.-% to about ≥40 wt.-% of a matrix compound; or
the first electron transport layer and the third electron transport layer comprises each about ≤50 wt.-% to about ≥40 wt.-% of a matrix compound;
wherein the weight percent of the matrix compound is based on the total weight of the corresponding transport layer.

According to various embodiments of the organic light-emitting diode, wherein
the first electron transport layer may comprise about ≥10 wt.-% to about ≤70 wt.-%, of a lithium halide or a lithium organic complex; or the first electron transport layer and the third electron transport layer may comprise each about ≥10 wt.-% to about ≤70 wt.-%, of a lithium halide or a lithium organic complex;
wherein the weight percent of the lithium halide and the lithium organic complex is based on the total weight of the corresponding electron transport layer.

According to various embodiments of the organic light-emitting diode, wherein
the first electron transport layer may comprise about ≥20 wt.-% to about ≤65 wt.-%, of a lithium halide or a lithium organic complex; or
the first electron transport layer and the third electron transport layer may comprise each about ≥20 wt.-% to about ≤65 wt.-%, of a lithium halide or a lithium organic complex;
wherein the weight percent of the lithium halide and the lithium organic complex is based on the total weight of the corresponding electron transport layer.

According to various embodiments of the organic light-emitting diode, wherein
the first electron transport layer may comprise about ≥50 wt.-% to about ≤60 wt.-%, of a lithium halide or a lithium organic complex; or
the first electron transport layer and the third electron transport layer may comprise each about ≥50 wt.-% to about ≤60 wt.-%, of a lithium halide or a lithium organic complex;
wherein the weight percent of the lithium halide and the lithium organic complex is based on the total weight of the corresponding electron transport layer.

According to various embodiments of the organic light-emitting diode, wherein
the first electron transport layer or the first electron transport layer and third electron transport layer, comprises:
a) about ≥10 wt.-% to about ≤70 wt.-% of the dopant;
b) about ≤90 wt.-% to about ≥30 wt.-% of a matrix compound;
the second electron transport layer, which is free of a dopant, comprises a matrix compound that is selected different from the first electron transport layer and the optional third electron transport layer; and
wherein the wt.-% of the components of each electron transport layer is selected such that the total wt.-% amount does not exceed 100 wt.-% and the wt.-% of the components are based on the total weight of the corresponding transport layer.

According to various embodiments of the organic light-emitting diode, wherein
the first electron transport layer or the first electron transport layer and third electron transport layer, comprises:
a) about ≥10 wt.-% to about ≤70 wt.-% of the dopant;
b) about ≤90 wt.-% to about ≥30 wt.-% of a matrix compound;
the second electron transport layer, which is free of a dopant, comprises a matrix compound, or preferably consist of one matrix material, that is selected different from the first electron transport layer and the optional third electron transport layer; and wherein the wt.-% of the components of each electron transport layer is selected such that the total wt.-% amount does not exceed 100 wt.-% and the wt.-% of the components are based on the total weight of the corresponding transport layer.

According to various embodiments of the organic light-emitting diode, wherein
the first electron transport layer or the first electron transport layer and third electron transport layer, comprises:
a) about ≥20 wt.-% to about ≤65 wt.-% of the dopant;
b) about ≤80 wt.-% to about ≥35 wt.-% of a matrix compound;
the second electron transport layer, which is free of a dopant, comprises a matrix compound, or preferably consist of one matrix material, that is selected different from the first electron transport layer and the optional third electron transport layer; and wherein the wt.-% of the components of each electron transport layer is selected such that the total wt.-% amount does not exceed 100 wt.-% and the wt.-% of the components are based on the total weight of the corresponding transport layer.

According to various embodiments of the organic light-emitting diode, wherein
the first electron transport layer, or the first electron transport layer and the third electron transport layer, comprises:
a) about ≥10 wt.-% to about ≤70 wt.-%, preferably about ≥20 wt.-% to about ≤65 wt.-% and also preferred about ≥50 wt.-% to about ≤60 wt.-% of a lithium halide, selected from the group comprising a LiF, LiCl, LiBr or LiJ, preferably LiF, or of a lithium organic complex of a lithium quinolate, a lithium borate, a lithium phenolate, a lithium pyridinolate or a lithium Schiff base; preferably of a lithium quinolate complex having the formula II, III or IV:

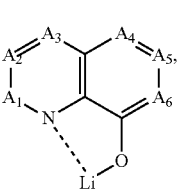

(II)

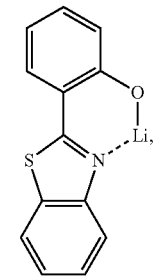

(III)

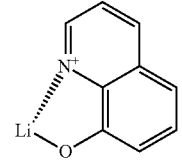

(IV)

wherein
A1 to A6 are same or independently selected from CH, CR, N, O,
R is same or independently selected from hydrogen, halogen, alkyl or aryl or heteroaryl with 1 to 20 carbon atoms, and more preferred of a lithium 8-hydroxyquinolate; and/or a lithium borate, more preferred the lithium borate is lithium tetra(1H-pyrazol-1-yl)borate;
b) about ≤90 wt.-% to about ≥30 wt.-%, preferably about ≤80 wt.-% to about ≥35 wt.-% and also preferred about ≤50 wt.-% to about ≥40 wt.-% and also preferred about ≤50 wt.-% to about ≥40 wt.-% of a matrix compound selected from the group comprising 3-(dibenzo[c,h]acridin-7-yl)phenyl)diphenylphosphine oxide, phenyl-bis(3-(pyren-1-yl)phenyl)phosphine oxide, 3-phenyl-3H-benzo[b]dinaphtho[2,1-d:1',2'-f]phosphepine-3-oxide, (3'-(dibenzo[c,h]acridin-7-yl)-[1,1'-biphenyl]-4-yl)diphenylphosphine oxide, (3-(10-(naphthalen-2-yl)anthracen-9-yl)phenyl(diphenylphosphine oxide and/or 2-(4-(9,10-di(naphthalen-2-yl)anthracen-2-yl)phenyl)-1-phenyl-1H-benzo[d]imidazole; and
the second electron transport layer comprises a matrix material having the formula Ia, Ib and/or Ic according to the invention; wherein the matrix material of the second electron transport layer is selected different to the matrix material of the first electron transport layer and the optional third electron transport layer; and the wt.-% of the components of each electron transport layer is selected such that the total wt.-% amount does not exceed 100 wt.-% and the wt.-% of the components are based on the total weight of the corresponding transport layer.

According to various embodiments of the organic light-emitting diode (OLED), the thicknesses of the first electron transport layer and/or the second electron transport layer and/or the third electron transport layer can be same or each independently in the range of about ≥1 nm to about ≤95 nm.

According to various embodiments of the organic light-emitting diode (OLED), the thicknesses of the first electron transport layer and/or the second electron transport layer and/or the third electron transport layer can be same or each independently in the range of about ≥3 nm to about ≤80 nm.

According to various embodiments of the organic light-emitting diode (OLED), the thicknesses of the first electron transport layer and/or the second electron transport layer and/or the third electron transport layer can be same or each independently in the range of, further preferred of about ≥6 nm to about ≤60 nm.

According to various embodiments of the organic light-emitting diode (OLED), the thicknesses of the first electron transport layer and/or the second electron transport layer and/or the third electron transport layer can be same or each independently in the range of about ≥10 nm to about ≤40 nm.

According to various embodiments of the organic light-emitting diode (OLED), the thicknesses of the first electron transport layer and/or the second electron transport layer and/or the third electron transport layer can be same or each independently in the range of about ≥8 nm to about ≤20 nm.

According to various embodiments of the organic light-emitting diode (OLED), the thicknesses of the first electron transport layer and/or the second electron transport layer and/or the third electron transport layer can be same or each independently in the range of about ≥10 nm to about ≤18 nm.

According to various embodiments of the organic light-emitting diode (OLED) the thicknesses of the electron transport layer stack can be in the range of about ≥25 nm to about ≤100 nm.

According to various embodiments of the organic light-emitting diode (OLED) the thicknesses of the electron transport layer stack can be in the range of about ≥30 nm to about ≤80 nm.

According to various embodiments of the organic light-emitting diode (OLED) the thicknesses of the electron transport layer stack can be in the range of about ≥35 nm to about ≤60 nm.

According to various embodiments of the organic light-emitting diode (OLED) the thicknesses of the electron transport layer stack can be in the range of about ≥36 nm to about ≤40 nm.

According to various embodiments of the organic light-emitting diode (OLED) of the present invention the electron transport layer stack has 2 to 4 electron transport layers and more preferred 2 to 3 electron transport layers.

According to various embodiments of the organic light-emitting diode (OLED) of the present invention the second electron transport layer can be arranged directly on the first electron transport layer and an optional third electron transport layer can be arranged directly on the second electron transport layer, so that the second electron transport layer is sandwiched between the first and third electron transport layers.

According to another aspect, there is provided an organic light-emitting diode comprising: a substrate; an anode electrode is formed on the substrate; an electron transport layer stack is formed on the anode electrode, whereby the electron transport layer stack comprises or consist of at least two electron transport layers; and finally a cathode electrode is formed, so that the electron transport layer stack is sandwiched between the anode electrode and the cathode electrode; and optional an electron injection layer is arranged between the electron transport layer and the cathode electrode.

According to various embodiments, the organic light-emitting diode (OLED) may further include at least one layer selected from the group consisting of a hole injection layer, a hole transport layer, an emission layer, and a hole blocking layer, arranged between the anode electrode and the electron transport layer.

According to another aspect, there is provided an organic light-emitting diode comprising in addition: at least one layer selected from the group consisting of a hole injection layer, a hole transport layer, an emission layer, and a hole blocking layer, arranged between the anode electrode and the electron transport layer stack.

According to various aspects, there is provided an organic light-emitting diode further comprising an electron injection layer arranged between the electron transport layer and the cathode electrode.

According to another aspect, there is provided an organic light-emitting diode comprising at least two electron transport layers and at least one electron injection layer.

Preferably the organic light-emitting diode may comprise an electron transport layer stack having two to four electron transport layers and more preferred two electron transport layers or three electron transport layers.

According to another aspect, there is provided an organic light-emitting diode comprising an electron transport layer stack of at least three electron transport layers and at least one electron injection layer. More preferred can be an organic light-emitting diode comprising three electron transport layers and no electron injection layer.

According to another aspect the organic light-emitting diode comprising an electron transport layer stack can be free of an electron injection layer.

According to various embodiments of the OLED of the present invention, the OLED may not comprise an electron injection layer.

According to various embodiments of the OLED of the present invention, the OLED may not comprise a charge generation layer.

According to various embodiments of the OLED of the present invention, the OLED may not comprise an electron injection layer and a charge generation layer.

According to another aspect, there is provided a method of manufacturing an organic light-emitting diode (OLED), the method using:
  at least three deposition sources; and/or
  deposition via vacuum thermal evaporation; and/or
  deposition via solution processing, preferably the processing is selected from spin-coating, casting, printing and/or slot-die coating.

According to various aspects, there is provided a method using:
  a first deposition source to release the matrix compound, and
  a second deposition source to release lithium halide or lithium organic complex; the method comprising the steps of forming the electron transport layer stack;
whereby the first electron transport layer is formed by releasing the matrix compound from the first deposition source and the lithium halide or lithium organic complex from the second deposition source;
  onto the first electron transport layer the second electron transport layer is formed by releasing the matrix compound from a third deposition source;
wherein the matrix compound of the first electron transport layer is not the same as the matrix compound of the second electron transport layer.

According to various aspects, there is provided a method using:
- a first and a third deposition source to release different matrix compounds, and
- a second and a fourth deposition source to release lithium halide or lithium organic complex, which is different to the lithium halide or lithium organic complex used for the second deposition source, preferably a lithium organic complex, and
- the method comprising the steps of forming the electron transport layer or the electron transport layer stack; whereby
- a first electron transport layer is formed by releasing the matrix compound from a first deposition source, and lithium halide or lithium organic complex from a second deposition source;
- onto the first electron transport layer a second electron transport layer is formed by releasing a matrix compound, different from the first electron transport layer, via a third deposition source;
- optional onto the second electron transport layer a third electron transport layer is formed by releasing the matrix compound used for the first electron transport layer via the first deposition source, and the fourth deposition source is used for releasing the lithium halide or lithium organic complex different to that used for the first electron transport layer; whereby the second electron transport layer is free of a dopant.

According to various aspects, the method may further include forming on the anode electrode an emission layer and at least one layer selected from the group consisting of forming a hole injection layer, forming a hole transport layer, or forming a hole blocking layer, between the anode electrode and the electron transport layer stack.

According to various aspects, the method may further include the steps for forming an organic light-emitting diode (OLED), wherein
- on a substrate an anode electrode is formed,
- on the anode electrode an emission layer is formed,
- on the emission layer at least two electron transport layers are formed, whereby the second electron transport layer is free of a dopant, optional a third electron transport layer is formed directly on the second electron transport layer, whereby the matrix material of the third electron transport layer is different to the matrix material of the second electron transport layer and the matrix material, lithium halide and/or lithium organic complex of the third electron transport layer is different or same to that of the first electron transport layer,
- on the electron transport layer stack a cathode electrode is formed,
- optional a hole injection layer, a hole transport layer, an emission layer, and a hole blocking layer, are formed between the anode electrode and the electron transport layer stack,
- optional an electron injection layer is formed between the electron transport layer or electron transport layer stack, and the cathode electrode.

According to various aspects, the method may further include the steps for forming an organic light-emitting diode (OLED), wherein an electron injection layer is formed between electron transport layer stack, and the cathode electrode.

According to various aspects, the method may further include the steps for forming an organic light-emitting diode (OLED), wherein an electron injection layer is formed between the electron transport layer stack, and the cathode electrode.

According to various aspects, the method may further include the steps for forming an organic light-emitting diode (OLED), wherein
- on a substrate an anode electrode is formed,
- on the anode electrode an emission layer is formed,
- on the emission layer an electron transport layer stack of at least a first electron transport and a second electron transport layer is formed, whereby the second electron transport layer is formed directly on the first electron transport layer and optional a third electron transport layer is formed directly on the second electron transport layer,
- on the electron transport layer stack a cathode electrode is formed,
- an electron injection layer is formed between the electron transport layer stack, and the cathode electrode
- optional a hole injection layer, a hole transport layer, an emission layer, and a hole blocking layer, are formed between the anode electrode and the electron transport layer stack.

According to various aspects, a device may comprise at least one organic light-emitting diode (OLED). A device comprising organic light-emitting diodes (OLED) is for example a display. According to various aspect, the organic light-emitting diode may comprise more than one light-emitting layer, for example a tandem or stacked light-emitting diode (OLED).

However, according to various embodiments of the OLED of the present invention, the OLED comprising two electron transport layers may not comprise a charge generation layer. However, according to various embodiments of the OLED of the present invention, the OLED comprising three or more electron transport layers may not comprise an electron injection layer and/or a charge generation layer.

Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the present invention will become apparent and more readily appreciated from the following description of the exemplary embodiments, taken in conjunction with the accompanying drawings, of which.

DETAILED DESCRIPTION

Figure 1:
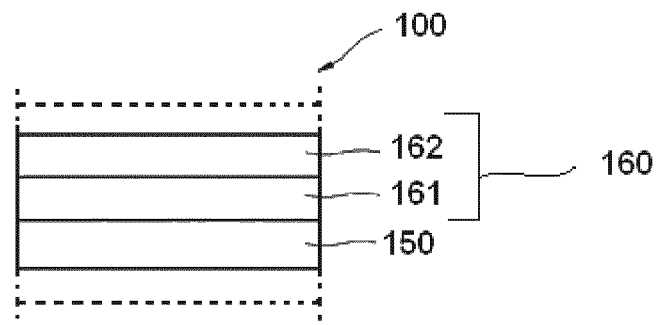
FIG. 1 is a schematic sectional view of an organic light-emitting diode (OLED), according to an exemplary embodiment of the present invention with an emission layer and two electron transport layers.

Reference will now be made in detail to the exemplary aspects, examples of which are illustrated in the accompanying drawings, wherein like reference numerals refer to the like elements throughout. The exemplary embodiments are described below, in order to explain the aspects, by referring to the figures.

Herein, when a first element is referred to as being formed or disposed "on" a second element, the first element can be disposed directly on the second element, or one or more other elements may be disposed there between. When a first element is referred to as being formed or disposed "directly on" a second element, no other elements are disposed there between.

FIG. 1 is a schematic sectional view of an organic light-emitting diode 100, according to an exemplary embodiment of the present invention. The OLED 100 includes an emission layer 150 and an electron transport layer stack (ETL) 160 comprising a first electron transport layer 161 and a second electron transport layer 162, whereby the second electron transport layer 162 is disposed directly on the first electron transport layer 161.

Figure 2:
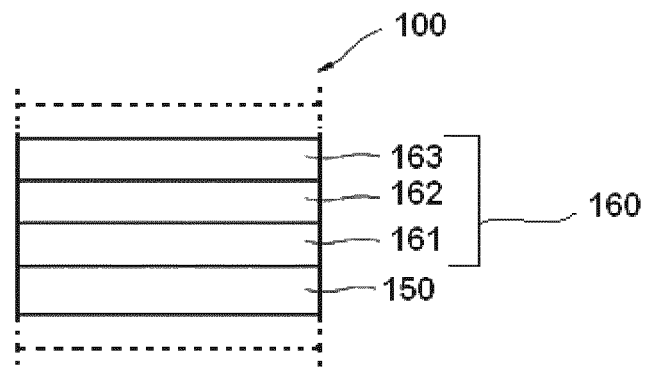
FIG. 2 is a schematic sectional view of an OLED, according to an exemplary embodiment of the present invention with an emission layer and three electron transport layers.

FIG. 2 is a schematic sectional view of an organic light-emitting diode 100, according to an exemplary embodiment of the present invention. The OLED 100 includes an emission layer 150 and an electron transport layer stack (ETL) 160 comprising a first electron transport layer 161, a second electron transport layer 162, and a third electron transport layer 163, whereby the second electron transport layer 162 is disposed directly on the first electron transport layer 161 and the third electron transport layer 163 is disposed directly on the first electron transport layer 162.

Figure 3:
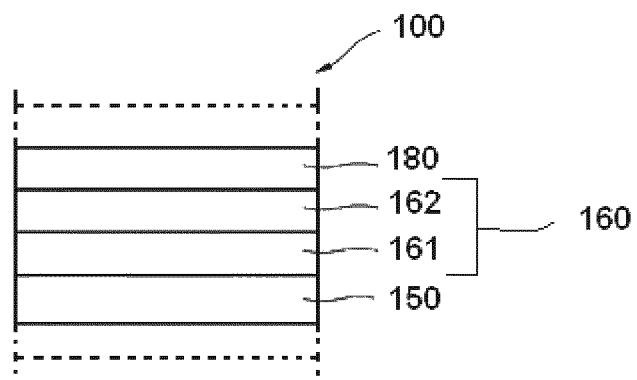
FIG. 3 is a schematic sectional view of an organic light-emitting diode (OLED), according to an exemplary embodiment of the present invention with an emission layer, two electron transport layers and an electron injection layer (EIL)

FIG. 3 is a schematic sectional view of an organic light-emitting diode 100, according to an exemplary embodiment of the present invention. The OLED 100 includes an emission layer 150, an electron injection layer (EIL) 180 and an electron transport layer stack (ETL) 160 comprising a first electron transport layer 161 and a second electron transport layer 162, whereby the second electron transport layer 162 is disposed directly on the first electron transport layer 161.

Figure 4:
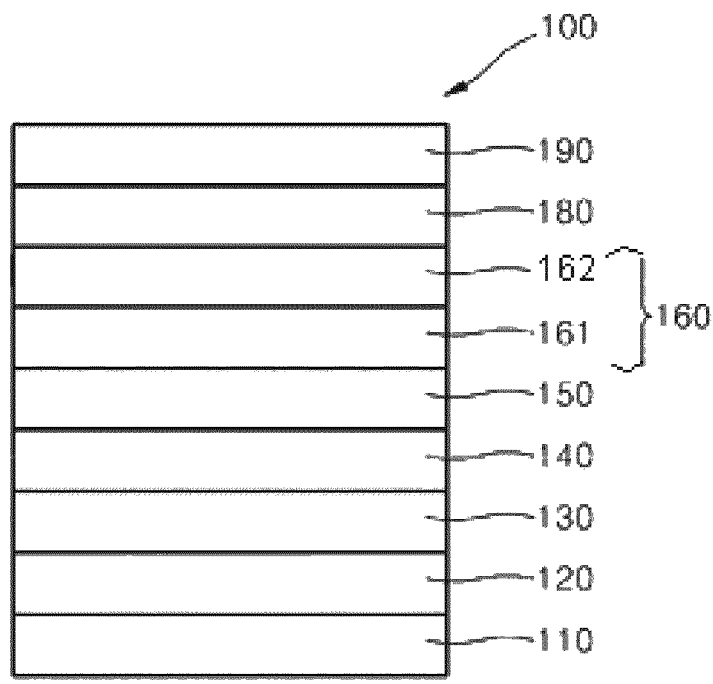
FIG. 4 is a schematic sectional view of an organic light-emitting diode (OLED), according to an exemplary embodiment of the present invention with an emission layer, two electron transport layers and an electron injection layer.

FIG. 4 is a schematic sectional view of an organic light-emitting diode 100, according to an exemplary embodiment of the present invention. The OLED 100 includes a substrate 110, a first electrode 120, a hole injection layer (HIL) 130, a hole transport layer (HTL) 140, an emission layer (EML) 150, an electron transport layer stack (ETL) 160, an electron injection layer (EIL) 180, and a second electrode 190. The electron transport layer stack (ETL) 160 includes a first electron transport layer 161 including a matrix compound and a dopant of a lithium organic complex and a second electron transport layer 162 including a matrix compound that differs from the matrix compound of the first electron transport layer 161 and is free of a dopant. The second electron transport layer 162 is directly formed on the first electron transport layer 161. The first layer 161 may be formed directly on the EML 150 and the electron injection layer (EIL) 180 may be formed directly on the second electron transport layer 162.

Figure 5:
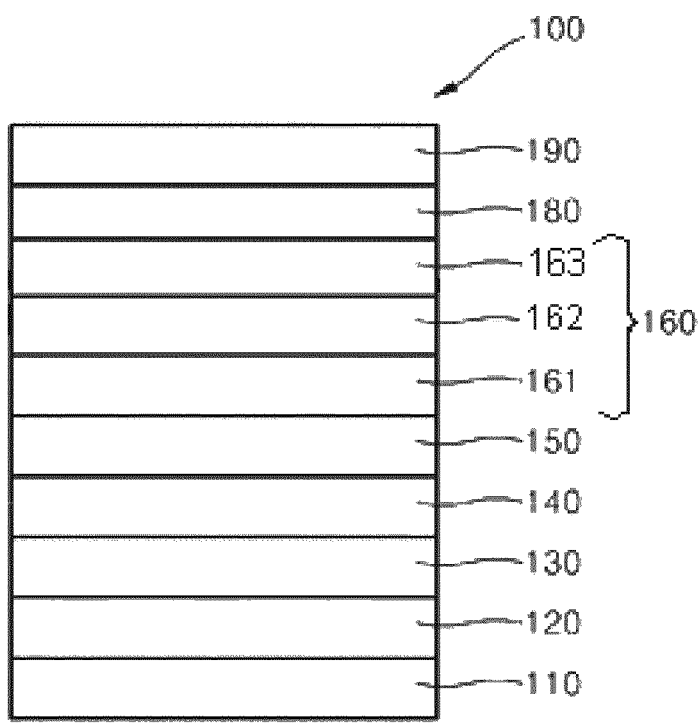
FIG. 5 is a schematic sectional view of an OLED, according to an exemplary embodiment of the present invention with an emission layer, three electron transport layers and an electron injection layer.

FIG. 5 is a schematic sectional view of an organic light-emitting diode 100, according to an exemplary embodiment of the present invention. The OLED 100 includes a substrate 110, a first electrode 120, a hole injection layer (HIL) 130, a hole transport layer (HTL) 140, an emission layer (EML) 150, an electron transport layer stack (ETL) 160, an electron injection layer (EIL) 180, and a second electrode 190. The electron transport layer stack (ETL) 160 includes a first electron transport layer 161 and a third electron transport layer 163 including the same matrix compounds and two different lithium organic complexes; and the second electron transport layer 162 includes a matrix compound that differs from the matrix compound of the first and second electron transport layer 161/162 and is free of a dopant. The second electron transport layer 162 is directly formed on the first electron transport layer 161 and the third electron layer 163 is directly formed on the second electron layer 162. The first layer 161 may be formed directly on the emission layer (EML) 150.

The substrate 110 may be any substrate that is commonly used in manufacturing of organic light-emitting diodes. If light is emitted through the substrate, the substrate 110 may be a transparent material, for example a glass substrate or a transparent plastic substrate, having excellent mechanical strength, thermal stability, transparency, surface smoothness, ease of handling, and waterproofness. If light is emitted through the top surface, the substrate 110 may be a transparent or non-transparent material, for example a glass substrate, a plastic substrate, a metal substrate or a silicon substrate.

The anode electrode 120 may be formed by depositing or sputtering a compound that is used to form the anode electrode 120. The compound used to form the anode electrode 120 may be a high work-function compound, so as to facilitate hole injection. If a p-doped HIL is used, the anode material may also be selected from a low work function material (i.e. aluminum). The anode electrode 120 may be a transparent or reflective electrode. Transparent conductive compounds, such as indium tin oxide (ITO), indium zinc oxide (IZO), tin-dioxide ($SnO_2$), and zinc oxide (ZnO), may be used to form the anode electrode 120. The anode electrode 120 may also be formed using magnesium (Mg), aluminum (Al), aluminum-lithium (Al—Li), calcium (Ca), magnesium-indium (Mg—In), magnesium-silver (Mg—Ag), silver (Ag), gold (Au), or the like.

The HIL 130 may be formed on the anode electrode 120 by vacuum deposition, spin coating, printing, casting, slot-die coating, Langmuir-Blodgett (LB) deposition, or the like. When the HIL 130 is formed using vacuum deposition, the deposition conditions may vary according to the compound that is used to form the HIL 130, and the desired structure and thermal properties of the HIL 130. In general, however, conditions for vacuum deposition may include a deposition temperature of 100° C. to 500° C., a pressure of $10^{-8}$ to $10^{-3}$ Torr (1 Torr equals 133.322 Pa), and a deposition rate of 0.1 to 10 nm/sec.

When the HIL 130 is formed using spin coating, printing, coating conditions may vary according to a compound that is used to form the HIL 130, and the desired structure and thermal properties of the HIL 130. For example, the coating conditions may include a coating speed of about 2000 rpm to about 5000 rpm, and a thermal treatment temperature of about 80° C. to about 200° C. Thermal treatment removes a solvent after the coating is performed.

The HIL 130 may be formed of any compound that is commonly used to form an HIL. Examples of compounds that may be used to form the HIL 130 include a phthalocyanine compound, such as copper phthalocyanine (CuPc), 4,4',4"-tris(3-methylphenylphenylamino) triphenylamine (m-MTDATA), TDATA, 2T-NATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), and polyaniline)/poly(4-styrenesulfonate (PANI/PSS).

The HIL 130 may be a pure layer of p-dopant or may be selected from a hole-transporting matrix compound doped with a p-dopant. Typical examples of known redox doped hole transport materials are: copper phthalocyanine (CuPc), which HOMO level is approximately −5.2 eV, doped with tetrafluoro-tetracyanoquinonedimethane (F4TCNQ), which LUMO level is about −5.2 eV; zinc phthalocyanine (ZnPc) (HOMO=−5.2 eV) doped with F4TCNQ; α-NPD (N,N'-Bis(naphthalen-1-yl)-N,N'-bis(phenyl)-benzidine) doped with F4TCNQ. α-NPD doped with 2,2'-(perfluoronaphthalen-2,6-diylidene) dimalononitrile (PD1). α-NPD doped with 2,2',2"-(cyclopropane-1,2,3-triylidene)tris(2-(p-cyanotetrafluorophenyl)acetonitrile) (PD2). Dopant concentrations can be selected from 1 to 20 wt.-%, more preferably from 3 wt.-% to 10 wt.-%.

The thickness of the HIL 130 may be in the range of about 1 nm to about 100 nm, and for example, about 1 nm to about 25 nm. When the thickness of the HIL 130 is within this range, the HIL 130 may have excellent hole injecting characteristics, without a substantial increase in driving voltage.

The hole transport layer (HTL) 140 may be formed on the HIL 130 by vacuum deposition, spin coating, slot-die coating, printing, casting, Langmuir-Blodgett (LB) deposition, or the like. When the HTL 140 is formed by vacuum deposition or spin coating, the conditions for deposition and coating may be similar to those for the formation of the HIL 130. However, the conditions for the vacuum or solution deposition may vary, according to the compound that is used to form the HTL 140.

The HTL 140 may be formed of any compound that is commonly used to form a HTL. Compound that can be suitably used is disclosed for example in Yasuhiko Shirota and Hiroshi Kageyama, Chem. Rev. 2007, 107, 953-1010 and incorporated by reference. Examples of the compound that may be used to form the HTL 140 are: a carbazole derivative, such as N-phenylcarbazole or polyvinylcarbazole; an amine derivative having an aromatic condensation ring, such as N,N'-bis(3-methylphenyl)-N,N'-diphenyl[1,1-biphenyl]-4,4'-diamine (TPD), or N,N'-di(naphthalen-1-yl)-N,N'-diphenyl benzydine (alpha-NPD); and a triphenylamine-based compound, such as 4,4',4"-tris(N-carbazolyl) triphenylamine (TCTA). Among these compounds, TCTA can transport holes and inhibit excitons from being diffused into the EML.

Compounds that can be preferably used to form a HTL layer are summarized in Table 5.

TABLE 5

| Name | Structure | Reference |
| --- | --- | --- |
| N4,N4"-di(naphthalen-1-yl)-N4,N4"-diphenyl-[1,1':4',1"-terphenyl]-4,4"-diamine | 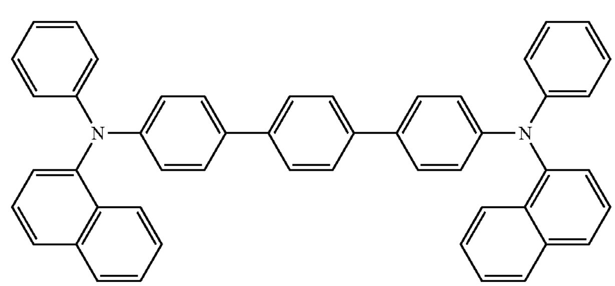 | DE102012101652 A1 |

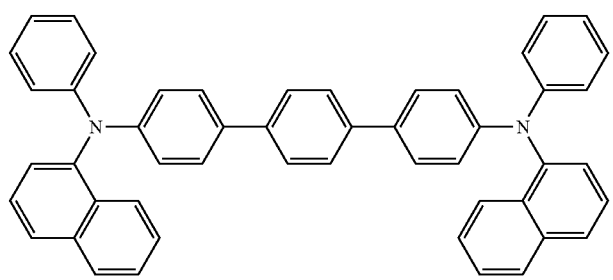 [SMILES: c1ccc(N(c2ccc(-c3ccc(-c4ccc(N(c5ccccc5)c5cccc6ccccc56)cc4)cc3)cc2)c2cccc3ccccc23)cc1]

TABLE 5-continued

| Name | Structure | Reference |
|---|---|---|
| Biphenyl-4-yl(9,9-diphenyl-9H-fluoren-2-yl)-[4-(9-phenyl-9H-carbazol-3-yl)phenyl]-amine | 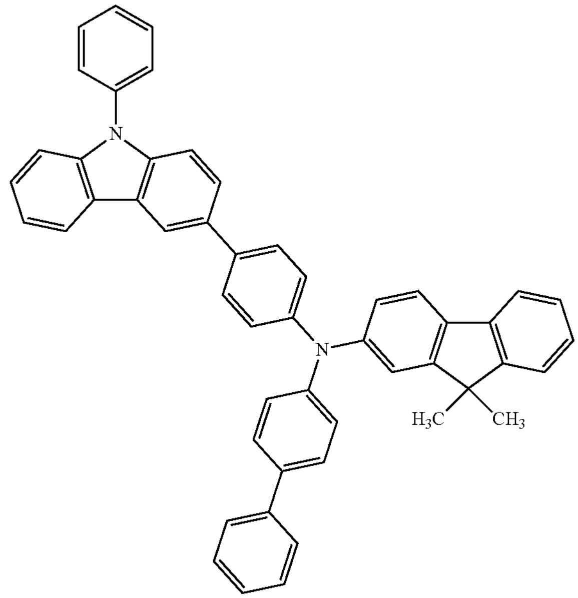 [SMILES: CC1(C)c2ccccc2-c2ccc(N(c3ccc(-c4ccccc4)cc3)c3ccc(-c4ccc5c(c4)c4ccccc4n5-c4ccccc4)cc3)cc21] | CAS 1242056-42-3 |
| 2,2',2''-(cyclopropane-1,2,3-triylidene)tris(2-(p-cyanotetrafluorophenyl)acetonitrile | 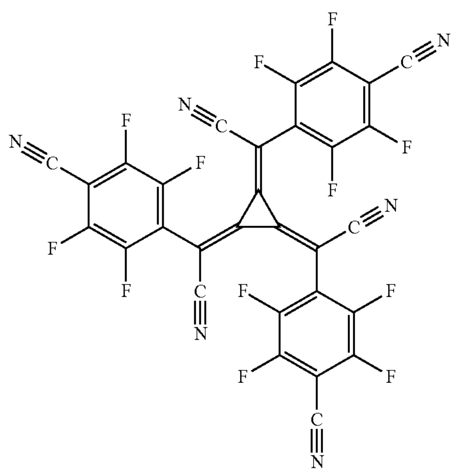 [SMILES: N#CC(=C1C(=C(C#N)c2c(F)c(F)c(C#N)c(F)c2F)C1=C(C#N)c1c(F)c(F)c(C#N)c(F)c1F)c1c(F)c(F)c(C#N)c(F)c1F] | EP 1988587 A1, EP 2180029 A1 |

The thickness of the HTL 140 may be in the range of about 5 nm to about 250 nm, preferably, about 10 nm to about 200 nm, further about 20 nm to about 190 nm, further about 40 nm to about 180 nm, further about 60 nm to about 170 nm, further about 80 nm to about 160 nm, further about 100 nm to about 160 nm, further about 120 nm to about 140 nm. A preferred thickness of the HTL 140 may be 170 nm to 200 nm.

When the thickness of the HTL 140 is within this range, the HTL 140 may have excellent hole transporting characteristics, without a substantial increase in driving voltage.

The EML 150 may be formed on the HTL 140 by vacuum deposition, spin coating, slot-die coating, printing, casting, LB, or the like. When the EML 150 is formed using vacuum deposition or spin coating, the conditions for deposition and coating may be similar to those for the formation of the HIL 130. However, the conditions for deposition and coating may vary, according to the compound that is used to form the EML 150.

The emission layer (EML) 150 may be formed of a combination of a host and a dopant. Example of the host are Alq3, 4,4'-N,N'-dicarbazole-biphenyl (CBP), poly(n-vinylcarbazole) (PVK), 9,10-di(naphthalen-2-yl)anthracene (ADN), TCTA, 1,3,5-tris(N-phenylbenzimidazole-2-yl)benzene (TPBI), 3-tert-butyl-9,10-di-2-naphthylanthracenee (TBADN), distyrylarylene (DSA), Bis(2-(2-hydroxyphenyl)benzothiazolate)zinc (Zn(BTZ) 2), E3 below, ADN and referred to as Formula 2, Compound 1 below, and Compound 2 below.

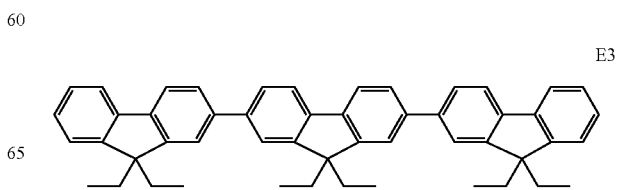

E3

Formula 2 (ADN)

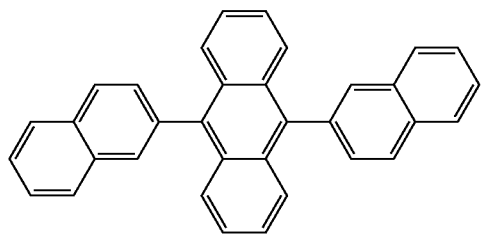

Compound 1

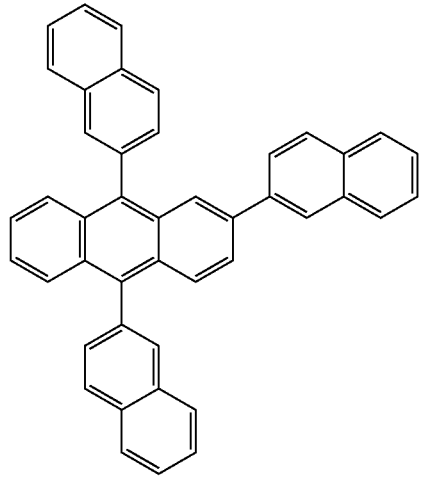

Compound 2

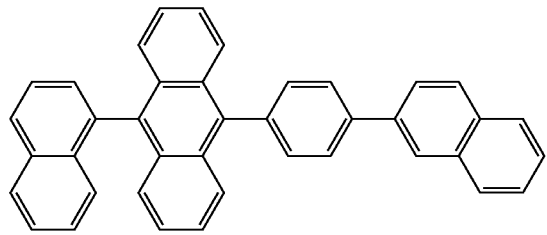

The dopant may be a phosphorescent or fluorescent emitter. Phosphorescent emitters are preferred due to their higher efficiency Examples of a red dopant are PtOEP, Ir(piq) 3, and Btp 2Ir(acac), but are not limited thereto. These compounds are phosphorescent emitters, however, fluorescent red dopants could also be used.

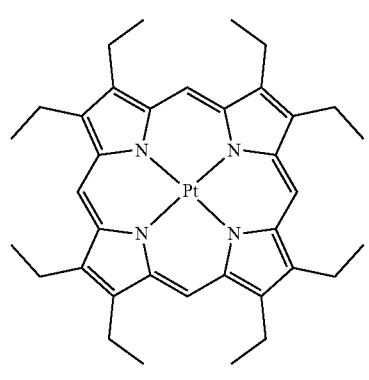

PtOEP

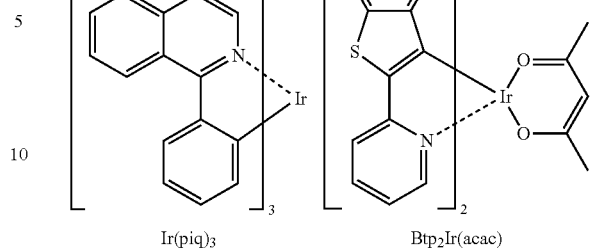

Ir(piq)₃     Btp₂Ir(acac)

Examples of a phosphorescent green dopant are Ir(ppy) 3 (ppy=phenylpyridine), Ir(ppy) 2(acac), Ir(mpyp) 3 are shown below. Compound 3 is an example of a fluorescent green emitter and the structure is shown below.

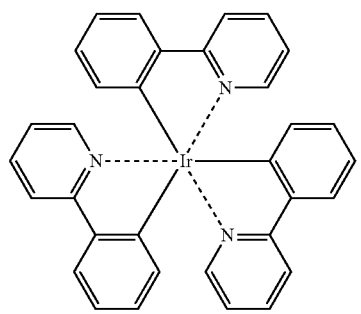

Ir(ppy)₃

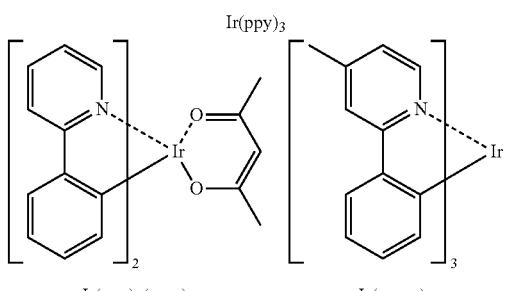

Ir(ppy)₂(acac)     Ir(mpyp)₂

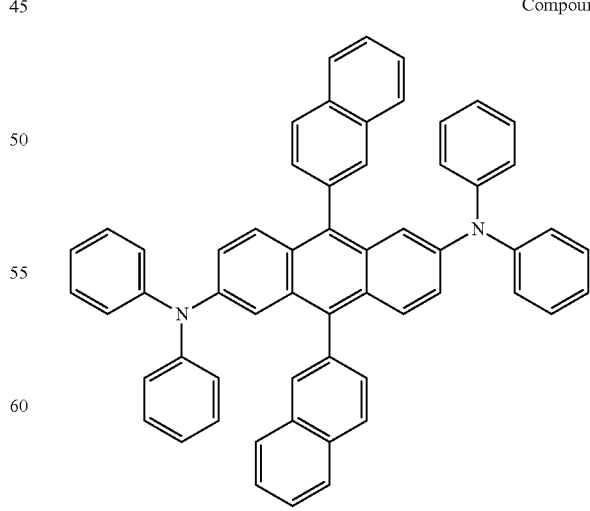

Compound 3

Examples of a phosphorescent blue dopant are F₂Irpic, (F₂ppy) ₂Ir(tmd) and Ir(dfppz) 3, ter-fluorene, the structures are shown below. 4,4'-bis(4-diphenyl amiostyryl)biphenyl (DPAVBi), 2,5,8,11-tetra-tert-butyl perylene (TBPe), and Compound 4 below are examples of fluorescent blue dopants.

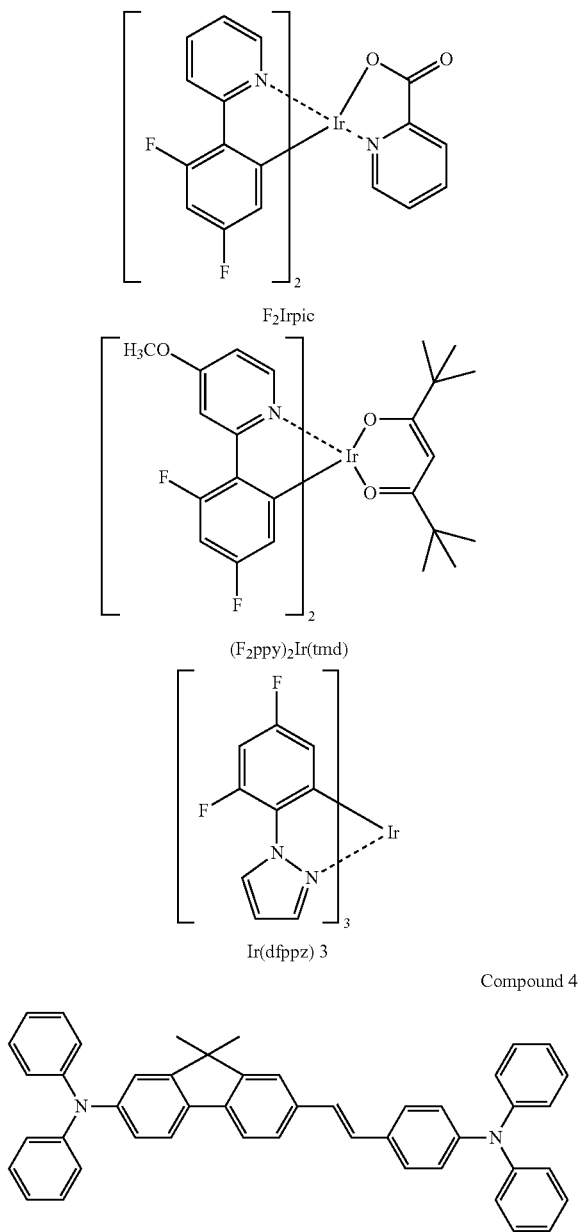

F₂Irpic (F₂ppy)₂Ir(tmd)

Ir(dfppz) 3

Compound 4

The amount of the dopant may be in the range of about 0.01 to about 50 parts by weight, based on 100 parts by weight of the host. The EML 150 may have a thickness of about 10 nm to about 100 nm, for example, about 20 nm to about 60 nm. When the thickness of the EML 150 is within this range, the EML 150 may have excellent light emission, without a substantial increase in driving voltage.

When the EML 150 comprises a phosphorescent dopant, a hole blocking layer (HBL) (not shown) may be formed on the EML 150, by using vacuum deposition, spin coating, slot-die coating, printing, casting, LB deposition, or the like, in order to prevent the diffusion of triplet excitons or holes into the ETL 160. When the HBL is formed using vacuum deposition or spin coating, the conditions for deposition and coating may be similar to those for the formation of the HIL 130. However, the conditions for deposition and coating may vary, according to the compound that is used to form the HBL. Any compound that is commonly used to form a HBL may be used. Examples of compounds for forming the HBL include an oxadiazole derivative, a triazole derivative, and a phenanthroline derivative.

The HBL may have a thickness of about 5 nm to about 100 nm, for example, about 10 nm to about 30 nm. When the thickness of the HBL is within this range, the HBL may have excellent hole-blocking properties, without a substantial increase in driving voltage.

The ETL 160 may be formed on the EML 150 or on the HBL if the HBL is formed.

The ETL 160 has a stacked structure, preferably of two ETL-layers (161/162), so that injection and transport of electrons may be balanced and holes may be efficiently blocked. In a conventional OLED, since the amounts of electrons and holes vary with time, after driving is initiated, the number of excitons generated in an emission area may be reduced. As a result, a carrier balance may not be maintained, so as to reduce the lifetime of the OLED.

However, in the ETL 160, the first layer 161 and the second layer 162 may have similar or identical energy levels. In general the matrix compound for the first electron layer (161) and second electron layer (162) are different.

The matrix compound for the first electron layer 161 and second electron layer 162 that can be suitable used are selected for example from the group comprising anthracene compounds, preferably 2-(4-(9,10-di(naphthalen-2-yl)anthracen-2-yl)phenyl)-1-phenyl-1H-benzo[d]imidazole; whereby the matrix material of the second electron transport layer 162 is selected different to the matrix material of the first electron transport layer 161 and the optional third electron transport layer 163.

The matrix compound for the electron transport layers of the electron layer stack for the first and the optional third electron transport layers can be selected from a phosphine oxide compound substituted with aryl, heteroaryl or alkyl group, preferably (3-(dibenzo[c,h]acridin-7-yl)phenyl)diphenylphosphine oxide, 3-phenyl-3H-benzo[b]dinaphtho[2,1-d:1',2'-f]phosphepine-3-oxide, phenyldi(pyren-1-yl)phosphine oxide, bis(4-(anthracen-9-yl)phenyl)(phenyl) phosphine oxide, (3-(9,10-di(naphthalen-2-yl)anthracen-2-yl)phenyl)diphenyl phosphine oxide, diphenyl(5-(pyren-1-yl)pyridin-2-yl)phosphine oxide, diphenyl(4'-(pyren-1-yl)[1,1'-biphenyl]-3-yl)phosphine oxide and/or phenyl bis(3-(pyren-1-yl)phenyl)phosphine oxide; whereby the matrix material of the second electron transport layer having the chemical formula Ia, Ib and/or Ic.

Anthracene compounds that can be used as matrix compounds are disclosed in U.S. Pat. No. 6,878,469 B and incorporated by reference.

Other matrix compounds that can be used are diphenylphosphine oxide, preferably (3-(dibenzo[c,h]acridin-7-yl)phenyl)diphenylphosphine oxide, phenylbis(3-(pyren-1-yl)phenyl)phosphine oxide, 3-phenyl-3H-benzo[b]dinaphtho[2,1-d:1',2'-f]phosphepine-3-oxide, bis(4-(anthracen-9-yl)phenyl)(phenyl)phosphine oxide, phenyldi(pyren-1-yl)phosphine oxide.

Diphenylphosphine oxide compounds that can be used as matrix compounds are disclosed in EP 2395571 A1, WO2013079217 A1, EP13187905, EP13199361 and JP2002063989 A1, incorporated by reference. Other suitable matrix compounds that can be used are phenanthroline compounds, preferably selected from the group comprising 2,4,7,9-tetraphenyl-1,10-phenanthroline and 2,9-di(biphenyl-4-yl)-4,7-diphenyl-1,10-phenanthroline. Phenanthroline compounds that can be used as matrix compounds are disclosed in EP 1786050 A1 and incorporated by reference.

Other suitable matrix compounds that can be used are pyrido[3,2-h]quinazoline compounds, preferably 4-(naphthalen-1-yl)-2,7,9-triphenylpyrido[3,2-h]quinazoline. Pyrido[3,2-h]quinazoline compounds that can be used as matrix compounds are disclosed in EP1970371 and incorporated by reference. Other suitable matrix compounds that can be used are triazine compounds, preferably 4,4'-bis(4, 6-diphenyl-1,3,5-triazine-2-yl)biphenyl. Triazine compounds that can be used as matrix compounds are disclosed in U.S. Pat. No. 6,225,467 and incorporated by reference. Other suitable matrix compounds that can be used are acridine compounds, preferably 7-(naphthalen-2-yl)dibenzo[c,h]acridine. Acridine compounds that can be used as matrix compounds are disclosed in EP 2395571 and incorporated by reference.

The matrix compound of the first electron layer (161) and/or third electron transport layer (163) may be a compound that efficiently transports electrons, such as an anthracene-based compound, diphenylphosphine oxide compound, triazine compound, quinazoline compound or a phenanthroline based compound, and preferably a matrix compound mentioned in Table 2; whereby the matrix material of the second electron transport layer 162, preferably a matrix compound mentioned in Table 4, is selected different to the matrix material of the first electron transport layer 161 and the optional third electron transport layer 163.

For example, the matrix compound of the first electron layer and/or third electron transport layer may be selected from the group consisting of ADN and referred to as Formula 2, a compound represented by Formula 3, and a compound represented by Formula 4 below; whereby the matrix material of the second electron transport layer is selected different to the matrix material of the first electron transport layer and the optional third electron transport layer:

Formula 2

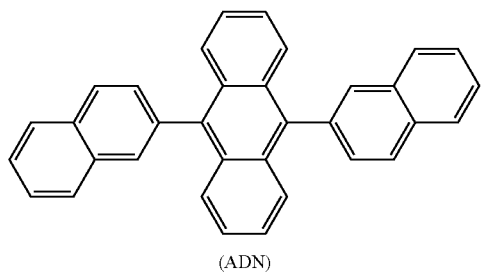

(ADN)

Formula 3

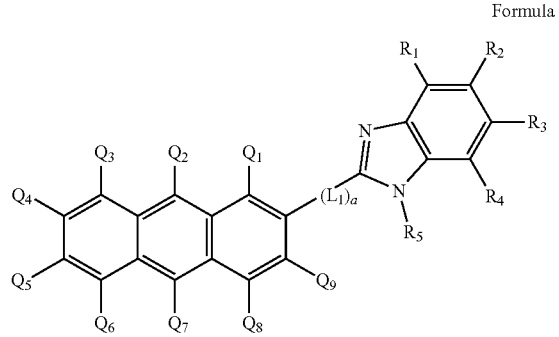

Formula 4

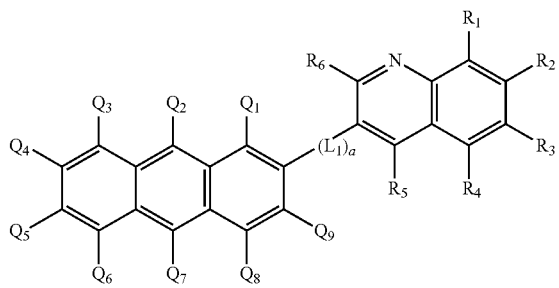

In Formulae 3 and 4, $R_1$ to $R_6$ are each independently a hydrogen atom, a halogen atom, a hydroxy group, a cyano group, a substituted or unsubstituted $C_1$-$C_{30}$ alkyl group, a substituted or unsubstituted $C_1$-$C_{30}$ alkoxy group, a substituted or unsubstituted $C_1$-$C_{30}$ acyl group, a substituted or unsubstituted $C_2$-$C_{30}$ alkenyl group, a substituted or unsubstituted $C_2$-$C_{30}$ alkynyl group, a substituted or unsubstituted $C_6$-$C_{30}$ aryl group, or a substituted or unsubstituted $C_3$-$C_{30}$ heteroaryl group. At least two adjacent $R_1$ to $R_6$ groups are optionally bonded to each other, to form a saturated or unsaturated ring. $L_1$ is a bond, a substituted or unsubstituted $C_1$-$C_{30}$ alkylene group, a substituted or unsubstituted $C_6$-$C_{30}$ arylene group, or a substituted or unsubstituted $C_3$-$C_{30}$ hetero arylene group. $Q_1$ through $Q_9$ are each independently a hydrogen atom, a substituted or unsubstituted $C_6$-$C_{30}$ aryl group, or a substituted or unsubstituted $C_3$-$C_{30}$ hetero aryl group, and "a" is an integer from 1 to 10.

For example, $R_1$ to $R_6$ may be each independently selected from the group consisting of a hydrogen atom, a halogen atom, a hydroxy group, a cyano group, a methyl group, an ethyl group, a propyl group, a butyl group, a methoxy group, an ethoxy group, a propoxy group, a butoxy group, a phenyl group, a naphthyl group, an anthryl group, a pyridinyl group, and a pyrazinyl group.

In particular, in Formula 3 and/or 4, $R_1$ to $R_4$ may each be a hydrogen atom, $R_5$ may be selected from the group consisting of a halogen atom, a hydroxy group, a cyano group, a methyl group, an ethyl group, a propyl group, a butyl group, a methoxy group, an ethoxy group, a propoxy group, a butoxy group, a phenyl group, a naphthyl group, an anthryl group, a pyridinyl group, and a pyrazinyl group. In addition, in Formula 4, $R_1$ to $R_6$ may each be a hydrogen atom.

For example, in Formula 3 and/or 4, $Q_1$ to $Q_9$ are each independently a hydrogen atom, a phenyl group, a naphthyl group, an anthryl group, a pyridinyl group, and a pyrazinyl group. In particular, in Formulae 3 and/or 4, $Q_1$, $Q_3$-$Q_6$, $Q_8$ and $Q_9$ are hydrogen atoms, and $Q_2$ and $Q_7$ may be each independently selected from the group consisting of a phenyl group, a naphthyl group, an anthryl group, a pyridinyl group, and a pyrazinyl group.

For example, $L_1$, in Formula 3 and/or 4, may be selected from the group consisting of a phenylene group, a naphthylene group, an anthrylene group, a pyridinylene group, and a pyrazinylene group. In particular, Li may be a phenylene group or a pyridinylene group. For example, "a" may be 1, 2, or, 3.

The matrix compound may be further selected from Compound 5 or 6 below:

Compound 5

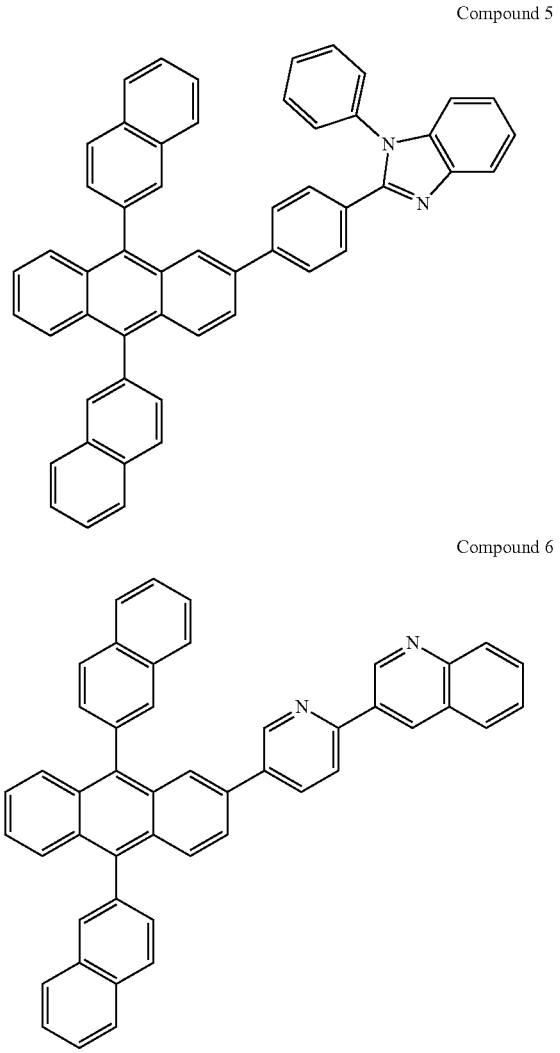 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1 ; c1ccc2cc(-c3c4ccccc4c(-c4ccc5ccccc5c4)c4cc(-c5ccc(-c6cnc7ccccc7c6)nc5)ccc34)ccc2c1]

Compound 6

The first electron transport layer 161 comprises a dopant of a lithium halide or a lithium organic complex; and the second electron transport layer 162 is free of a dopant.

According to another aspect the first electron transport layer 161 comprises a lithium halide or a lithium organic complex; and the second electron transport layer 162 comprises no dopant; and the third electron transport layer 163 comprises a lithium halide or a lithium organic complex that is the same or differs from the lithium halide or lithium organic complex of the first electron transport layer 161.

The ETL layer stack thickness can be adjusted such that the light out coupling is maximized. Further ETL layer stack thickness can be adjusted for the desired color tuning, for example to achieve a deeper shade of blue, i.e. smaller CIE-y.

The thicknesses of the first electron transport layer 161, second electron transport layer 162 and/or third electron transport layer 163 may be the same or each independently in the range of about ≥1 nm to about ≤95 nm, preferably of about ≥3 nm to about ≤80 nm, further preferred of about ≥5 nm to about ≤60 nm, also preferred of about ≥6 nm to about ≤40 nm, in addition preferred about ≥8 nm to about ≤20 nm and more preferred of about ≥10 nm to about ≤18 nm.

When the thicknesses of the first electron transport layer 161, second electron transport layer 162 and/or third electron transport layer 163 within this range, preferably of about ≥10 nm to about ≤18 nm, the electron transport layer stack 160 may effectively inject and transport electrons, without a substantial increase in driving voltage.

For blue emitting OLEDs, the thickness of the ETL layer stack is 10 nm to 50 nm, preferably 30 nm to 40 nm. For red and green emitting OLEDs, the thickness of ETLs is 20 nm to 100 nm, preferably 20 nm to 100 nm and more preferably 30 nm to 80 nm. The thickness is selected so as to maximize efficiency of light emission.

The amount of the total lithium organic complex in the first electron transport layer 161 may be in the range of about ≥10 wt.-% to about ≤70 wt.-%, preferably about ≥20 wt.-% to about ≤65 wt.-%, and also preferred about ≥50 wt.-% to about ≤60 wt.-%, by weight of the first electron transport layer 161.

The amount of the total lithium organic complex in the first electron transport layer 161 that is free of a metal salt may be in the range of about ≥10 wt.-% to about ≤70 wt.-%, preferably about ≥20 wt.-% to about ≤65 wt.-%, and also preferred about ≥50 wt.-% to about ≤60 wt.-%, by weight of the first electron transport layer 161.

The amount of the total lithium organic complex in the third electron transport layer 163 may be in the range of about ≥10 wt.-% to about ≤70 wt.-%, preferably about ≥20 wt.-% to about ≤65 wt.-%, and also preferred about ≥50 wt.-% to about ≤60 wt.-%, by weight of the third electron transport layer 163.

The amount of the total lithium organic complex in the third electron transport layer 163 that is free of a metal salt may be in the range of about ≥10 wt.-% to about ≤70 wt.-%, preferably about ≥20 wt.-% to about ≤65 wt.-%, and also preferred about ≥50 wt.-% to about ≤60 wt.-%, by weight of the third electron transport layer 163.

The ETL-stack 160 may be formed on the EML 150 by vacuum deposition, spin coating, slot-die coating, printing, casting, or the like. When the ETL 160 is formed by vacuum deposition or spin coating, the deposition and coating conditions may be similar to those for formation of the HIL 130. However, the deposition and coating conditions may vary, according to a compound that is used to form the ETL-stack 160.

Using vacuum deposition, the first electron transport layer 161 of the ETL 160 may be formed using a first deposition source to deposit a matrix compound and a second deposition source to deposit a lithium halide or lithium organic complex. The first deposition source and second deposition source are positioned relative to one another, such that a mixed deposition region of the first electron transport layer 161 is formed directly on the EML 150.

The second electron transport layer 162 of the ETL 160 may be formed using a third deposition source, since the matrix compound is different to the first electron transport layer ETL 161 and optional third electron transport layer ETL 163.

If compounds used to form the first ETL 161 and third ETL 163 are identical, the same deposition sources can be used.

If compounds used to form the first ETL 161 and third ETL 163 are not identical, the additional deposition sources can be used for the third ETL 163.

The deposition sources are positioned relative to one another, such that the second electron transport layer 162 is formed directly on the first electron transport layer 161.

The stacking process is more simply and quickly performed, as compared to prior methods. In particular, since a plurality of ETL layers may be almost simultaneously deposited in a single chamber, the chamber may not be required to be exhausted after the formation of each layer.

The EIL 180, which facilitates injection of electrons from the cathode, may be formed on the ETL 160, preferably directly on the second electron transport layer 162. Examples of materials for forming the EIL 180 include KF, LiF, NaCl, CsF, Li$_2$O, BaO, Ca, Ba, Yb, Mg which are known in the art. Deposition and coating conditions for forming the EIL 180 are similar to those for formation of the HIL 130, although the deposition and coating conditions may vary, according to a material that is used to form the EIL 180.

According to one aspect the electron injection layer may comprises a matrix compound of a phosphine oxide compound substituted with aryl, heteroaryl or alkyl group, preferably 3-Phenyl-3H-benzo[b]dinaphtho[2,1-d:1',2'-f]phosphepine-3-oxide, and doped with a lithium halide or doped with a lithium organic complex, preferably lithium tetra(1H-pyrazol-1-yl)borate.

According to one aspect the electron injection layer may comprises a matrix compound of a phosphine oxide compound substituted with aryl, heteroaryl or alkyl group, preferably (3-(dibenzo[c,h]acridin-7-yl)phenyl)diphenylphosphine oxide or 3-Phenyl-3H-benzo[b]dinaphtho[2,1-d:1',2'-f]phosphepine-3-oxide, and doped with an elemental metal selected from a group comprising an alkali, alkaline earth or rare earth metals, preferably Li, Cs, Mg, Ca, Yb, or Sm.

According to one aspect the electron injection layer may consist of a metal halide or metal organic complex, preferably LiQ, AlQ3, ZrQ4, KF or LiF, wherein Q is a 8-hydroxyquinolate.

According to one aspect the electron injection layer may consist of an alkali, alkaline earth or rare earth metal, preferably Li, Cs, Mg, Ca, Yb, or Sm.

According to a preferred embodiment the electron transport layer stack of two electron transport layers 161/162 may contain an electron injection layer 180.

According to a preferred embodiment the electron transport layer stack of three electron transport layers 161/162/163 may not contain an electron injection layer 180.

The thickness of the EIL 180 may be in the range of about 0.1 nm to 10 nm, for example, in the range of 0.5 nm to 9 nm or about ≥0.5 nm to ≤5 nm. When the thickness of the EIL 180 is within this range, the EIL 180 may have satisfactory electron-injecting properties, without a substantial increase in driving voltage.

The cathode electrode 190 is formed on the EIL 180 if present. The cathode electrode 190 may be a cathode, which is an electron-injecting electrode. The second electrode 190 may be formed of a metal, an alloy, an electrically conductive compound, or a mixture thereof. The second electrode 190 may have a low work function. For example, the second electrode 190 may be formed of lithium (Li), magnesium (Mg), aluminum (Al), aluminum (Al)-lithium (Li), calcium (Ca), barium (Ba), ytterbium (Yb), magnesium (Mg)-indium (In), magnesium (Mg)-silver (Ag), or the like. In addition, the second electrode 190 may be formed of a transparent conductive material, such as ITO or IZO.

The thickness of the cathode electrode 190 may be in the range of about 5 nm to 1000 nm, for example, in the range of 10 nm to 100 nm. When the cathode electrode 190 is in the range of 5 nm to 50 nm, the electrode will transparent even if a metal or metal alloy is used.

Since the layers of the ETL 160 have similar or identical energy levels, the injection and transport of the electrons may be controlled, and the holes may be efficiently blocked. Thus, the OLED 100 may have long lifetime.

Figure 6:
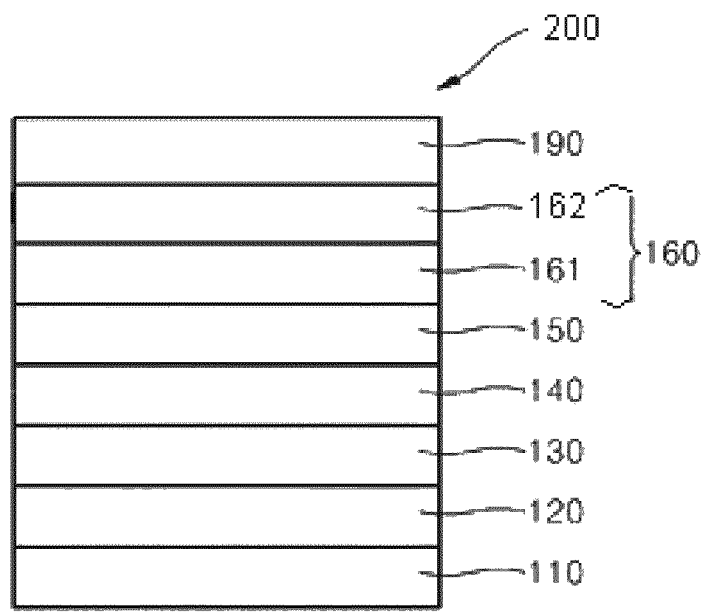
FIG. 6 is a schematic sectional view of an OLED, according to an exemplary embodiment of the present invention with an emission layer and two electron transport layers and having no electron injection layer (EIL).
Figure 7:
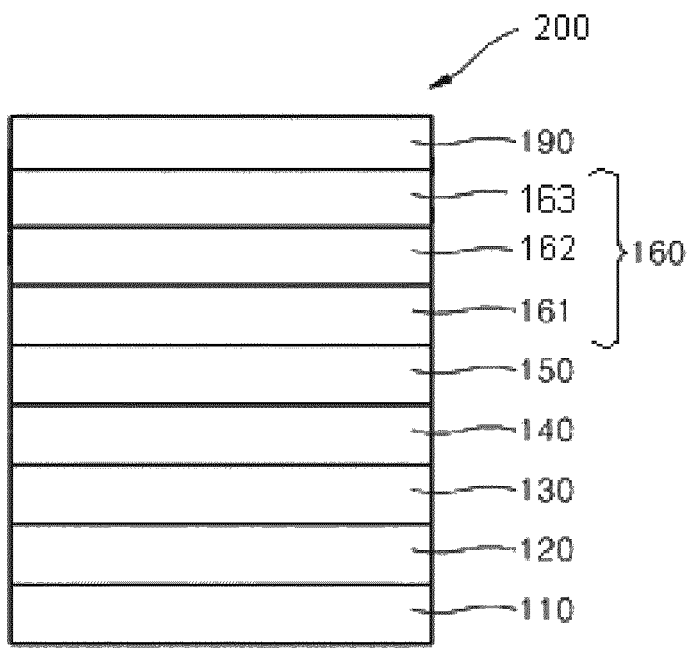
FIG. 7 is a schematic sectional view of an OLED, according to an exemplary embodiment of the present invention with three electron transport layers and having no electron injection layer (EIL).

FIG. 6 and FIG. 7 is a schematic sectional view of an OLED 200, according to another exemplary embodiment of the present invention. The OLED 200 of FIGS. 7 and 8 has no electron injection layer (EIL) 180.

Referring to FIGS. 6 and 7 the OLED 200 includes a substrate 110, a first electrode 120, a HIL 130, a HTL 140, an EML 150, an ETL 160, and a second electrode 190. The ETL stack 160 of FIG. 6 includes a first ETL layer 161 and a second ETL layer 162. The ETL stack 160 of FIG. 7 includes a first ETL layer 161, a second ETL layer 162 and a third ETL layer 163.

The electron transport layer stack 160 of FIG. 6 comprises at least two electron transport layers 161 and 162, wherein a first electron transport layer 161 and a second electron transport layer 162 comprises at least one matrix compound, whereby the matrix compound of the second electron transport layer 162 differs from the matrix compound of the first electron transport layer 161, and in addition, the first electron transport layer comprises as a dopant at least one lithium organic complexes, and the second electron transport layer comprises no dopant; wherein the first electron transport layer is arranged closest to an anode and the second electron transport layer is arranged closest to a cathode.

The electron transport layer stack 160 of FIG. 7 comprises at least three electron transport layers 161, 162 and 163, wherein a first electron transport layer 161, a second electron transport layer 162 and a third electron transport layer 163 comprises at least one matrix compound, whereby the matrix compound of the second electron transport layer 162 differs from the matrix compound of the first electron transport layer 161 and third electron transport layer 163, and in addition, the first electron transport layer 161 comprises as a dopant a lithium halide or lithium organic complex, the third electron transport layer 163 comprises as a dopant a lithium halide or lithium organic complex, and the second electron transport layer 162 is free of a dopant; wherein the first electron transport layer 161 is arranged closest to an anode and the third electron transport layer 163 is arranged closest to a cathode.

The layers of the ETL 161 and 162 or of the ETL 161 and 163 have similar or identical energy levels.

The OLED 200 have a significant reduced low voltage to efficiently operate an OLED. The substrate 110, the first electrode 120, the hole injection layer 130, the hole transport layer 140, the emission layer 150, and the electron transport layer 161 and 162 of the OLED 200 of FIG. 6 and FIG. 7 are similar to corresponding elements described with reference to FIGS. 4 and 5, respectively. Even though the structure of the OLED 200 and the method of manufacturing the OLED 200 are described with reference to FIGS. 4 and 5, other methods known in the art can be used. For example, the ETL stack 160 may include three or more ETL layers but two ETL layers of ETL 161 and 162 or three two ETL layers of ETL 161, 162 and 163 may be preferred.

In the description above the method of manufacture an OLED of the present invention is started with a substrate 110 onto which an anode electrode 120 is formed, on the anode electrode 120 an emission layer 150 is formed. An electron transport layer 161 or electron transport layer stack 160 is formed on the emission layer 150, wherein in case of an electron transport layer stack 160 the first electron transport layer 161 is formed on the emission layer 150 and the second electron transport layer 162 is formed directly on the first electron transport layer 161, on the electron transport layer stack 160, in this case on the second electron transport layer 162, a cathode electrode 190 is formed, optional a hole injection layer 130, and a hole transport layer 140, are formed between the anode electrode 120 and the electron transport layer stack 160, an optional hole blocking layer is formed between the emission layer and the ETL layer stack, and an electron injection layer 180 is formed between the electron transport layer 160 and the cathode electrode 190.

However, the OLED of the present invention can be manufactured also the other way around, starting with the cathode electrode 190 onto which optionally an electron injection layer 180 is formed. On the cathode electrode 190 or on the electron injection layer 180, if present, the electron transport layer stack 160 is formed, whereby directly on the second electron transport layer 162 the first electron transport layer 161 is formed, and so on.

In case of a three layer electron transport layer stack 160, the second electron layer 162 is formed on the first electron layer 161 and the third electron layer 163 is formed on the second electron layer 162. Then a cathode electrode 190 is formed, optional a hole injection layer 130, and a hole transport layer 140, are formed between the anode electrode 120 and the electron transport layer stack 160, an optional hole blocking layer is formed between the emission layer and the ETL layer stack, and optionally an electron injection layer 180 is formed between the electron transport layer 160 and the cathode electrode 190.

While not shown in FIGS. 4 to 7, a sealing layer may further be formed on the second electrodes 190, in order to seal the OLEDs 100, 200. In addition, various other modifications may be applied thereto.

Hereinafter, one or more exemplary aspects will be described in detail with reference to the following examples. However, these examples are not intended to limit the purpose and scope of the one or more exemplary aspects. Suitable matrix compounds in the second undoped ETL are selected from compounds of chemical formula Ia, Ib and/or Ic.

To check the impact of the position of the nitrogen atom in the pyridinyl moiety of compounds of chemical formula Ia, Ib and/or Ic, the energy levels and optical bandgap were calculated.

Geometry optimizations and property calculations of the molecules were performed using the DFT-functional BP (B88 exchange, VWN(V) and Perdew's 1986 correlation) and the DEF-SV(P) basis set as implemented in the program package Turbomole-V6.5, which is commercially available at TURBOMOLE GmbH (Ltd), Karlsruhe.

Another aspect is directed to a device comprising at least one organic light-emitting diode (OLED). A device comprising organic light-emitting diodes (OLED) is for example a display.

Another aspect is directed to compounds having the chemical formula Ia, Ib and/or Ic:

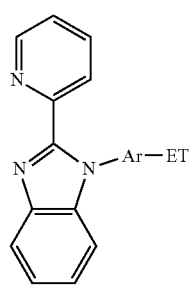

(Ia)

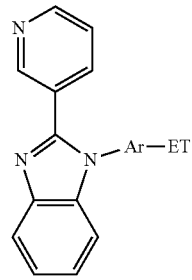

(Ib)

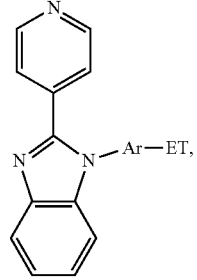

(Ic)

wherein
Ar=substituted or unsubstituted arylene with 6 to 20 ring-forming carbon atoms; or carbazolylene;
ET=substituted or unsubstituted aryl group with 13 to 40 ring-forming carbon atoms; or a substituted or unsubstituted heteroaryl group with 14 to 40 ring-forming atoms; and
excluding the compound (VI):

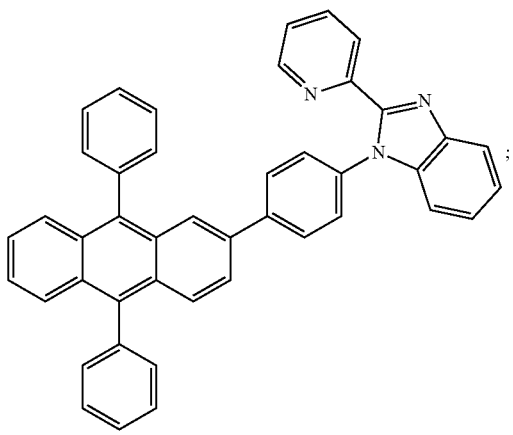

(VI)

and excluding a compound of formula Ia, Ib and Ic, wherein ET is an anthracen-9-yl group.

Another aspect is directed to compounds having the chemical formula Ia, Ib and/or Ic, as mentioned above, wherein Ar is selected from an arylene or carbazolyene group wherein the conjugation of π-electrons is reduced between the 1-benzimidazole moiety and ET.

Another aspect is directed to compounds having the chemical formula Ia, Ib and/or Ic, as mentioned above, wherein Ar is selected from a chemical formula comprising at least one m-phenylene group.

Another aspect is directed to compounds having the chemical formula Ia, Ib and/or Ic, as mentioned above, wherein Ar is selected from a group comprising a m-phenylene, biphenyl-2,2'-diyl, biphenyl-3,3'diyl, biphenyl-3,4'-diyl, fluoren-3,6-diyl, p-terphenyl-3,3'-diyl, m-terphenyl-4,4'-diyl, m-terphenyl-3,3'-diyl, m-terphenyl-2,2'-diyl, o-terphenyl-4,4'-diyl, o-terphenyl-3,3'-diyl, o-terphenyl-2,2'-diyl; or naphthalen-2,6-diyl.

Another aspect is directed to compounds having the chemical formula Ia, Ib and/or Ic, as mentioned above, wherein ET is selected from the group of acridine, acridine compounds substituted with aryl or heteroaryl groups.

Another aspect is directed to compounds having the chemical formula Ia, Ib and/or Ic, as mentioned above:

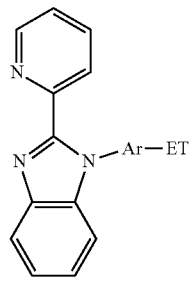

(Ia)

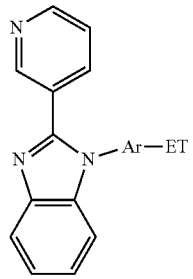

(Ib)

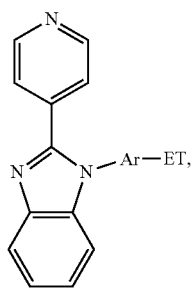

(Ic)

wherein
Ar=substituted or unsubstituted arylene with 6 to 20 ring-forming carbon atoms, preferably 6 to 18 ring-forming carbon atoms, and more preferred 6 to 13 ring-forming carbon atoms; or carbazolylene;
ET=substituted or unsubstituted aryl group with 13 to 40 ring-forming carbon atoms, preferably 14 to 26 ring-forming carbon atoms, and more preferred 14 to 22 ring-forming carbon atoms; or a substituted or unsubstituted heteroaryl group with 14 to 40 ring-forming atoms, preferably 20 to 24 ring-forming atoms.

Another aspect is directed to compounds having the chemical formula Ia, Ib and/or Ic, as mentioned above:

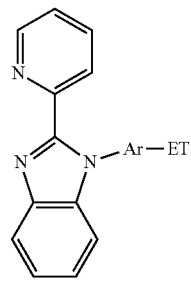

(Ia)

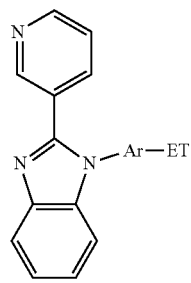

(Ib)

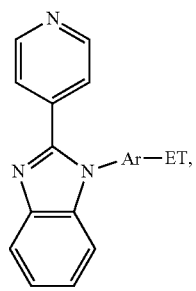

(Ic)

wherein
Ar=substituted or unsubstituted arylene with 6 to 20 ring-forming carbon atoms, preferably 6 to 18 ring-forming carbon atoms, and more preferred 6 to 13 ring-forming carbon atoms; or carbazolylene;
ET=substituted or unsubstituted aryl group with 13 to 40 ring-forming carbon atoms, preferably 14 to 26 ring-forming carbon atoms, and more preferred 14 to 22 ring-forming carbon atoms; or a substituted or unsubstituted heteroaryl group with 14 to 40 ring-forming atoms, preferably 20 to 24 ring-forming atoms; and excluding the compound (VI):

(VI)

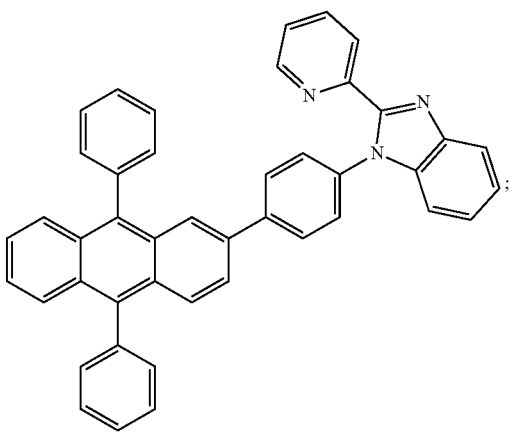

and excluding a compound of formula Ia Ib and Ic, wherein ET is an anthracen-9-yl group.

Another aspect is directed to compounds having the chemical formula Ia, Ib and/or Ic, as mentioned above, wherein Ar of Formula Ia, Ib and Ic is selected from the group of: unsubstituted arylene:

o-phenylene, m-phenylene, p-phenylene, biphenyl-2,2'-diyl, biphenyl-3,3'diyl, biphenyl-4,4'diyl, biphenyl-3,4'-diyl, p-terphenyl-4,4'-diyl, p-terphenyl-3,3'-diyl, p-terphenyl-2,2'-diyl, m-terphenyl-4,4'-diyl, m-terphenyl-3,3'-diyl, m-terphenyl-2,2'-diyl, o-terphenyl-4,4'-diyl, o-terphenyl-3,3'-diyl, o-terphenyl-2,2'-diyl; naphthalen-2,6-diyl, naphthalen-1,4-diyl; or substituted arylene or carbazolylene:

o-phenylene, m-phenylene, p-phenylene, biphenyl-2,2'-diyl group, biphenyl-3,3'diyl group, biphenyl-4,4'diyl group, biphenyl-3,4'-diyl group, fluoren-2,7-diyl group, fluoren-3,6-diyl group, carbazol-3,6-diyl group, carbazol-2,7-diyl, p-terphenyl-4,4'-diyl, p-terphenyl-3,3'-diyl, p-terphenyl-2,2'-diyl, m-terphenyl-4,4'-diyl, m-terphenyl-3,3'-diyl, m-terphenyl-2,2'-diyl, o-terphenyl-4,4'-diyl, o-terphenyl-3,3'-diyl, o-terphenyl-2,2'-diyl; naphthalen-2,6-diyl, naphthalen-1,4-diyl; and wherein the substituent of the substituted arylene or carbazolyene is selected from the group of an alkyl group with 1 to 15 carbon atoms, preferably 1 to 12 carbon atoms, more preferred 1 to 4 carbon atoms; an alkoxy group with 1 to 15 carbon atoms, preferably 1 to 5 carbon atoms and more preferred 1 to 2 carbon atoms.

Another aspect is directed to compounds having the chemical formula Ia, Ib and/or Ic, as mentioned above, wherein Ar of Formula Ia, Ib and Ic is selected from the group of: unsubstituted arylene:

o-phenylene, m-phenylene, p-phenylene, biphenyl-2,2'-diyl, biphenyl-3,3'diyl, biphenyl-4,4'diyl, biphenyl-3,4'-diyl, p-terphenyl-4,4'-diyl, p-terphenyl-3,3'-diyl, p-terphenyl-2,2'-diyl, m-terphenyl-4,4'-diyl, m-terphenyl-3,3'-diyl, m-terphenyl-2,2'-diyl, o-terphenyl-4,4'-diyl, o-terphenyl-3,3'-diyl, o-terphenyl-2,2'-diyl; naphthalen-2,6-diyl, naphthalen-1,4-diyl; or substituted arylene or carbazolylene:

o-phenylene, m-phenylene, p-phenylene, biphenyl-2,2'-diyl, biphenyl-3,3'diyl, biphenyl-4,4'diyl, biphenyl-3,4'-diyl, fluoren-2,7-diyl, fluoren-3,6-diyl, carbazol-3,6-diyl, carbazol-2,7-diyl, p-terphenyl-4,4'-diyl, p-terphenyl-3,3'-diyl, p-terphenyl-2,2'-diyl, m-terphenyl-4,4'-diyl, m-terphenyl-3,3'-diyl, m-terphenyl-2,2'-diyl, o-terphenyl-4,4'-diyl, o-terphenyl-3,3'-diyl, o-terphenyl-2,2'-diyl; naphthalen-2,6-diyl, naphthalen-1,4-diyl; and wherein the substituent of the substituted arylene or carbazolyene is selected from the group of an alkyl group with 1 to 15 carbon atoms, preferably 1 to 12 carbon atoms, more preferred 1 to 4 carbon atoms; an alkoxy group with 1 to 15 carbon atoms, preferably 1 to 5 carbon atoms and more preferred 1 to 2 carbon atoms; and excluding the compound (VI):

(VI)

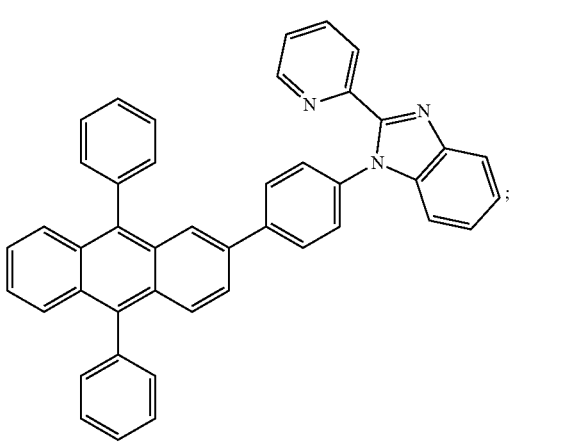

and excluding a compound of formula Ia, Ib and Ic, wherein ET is an anthracen-9-yl group.

Another aspect is directed to compounds having the chemical formula Ia, Ib and/or Ic, as mentioned above, wherein Ar of chemical formula Ia, Ib and/or Ic is selected from the group of A1 to A69:

(A1)

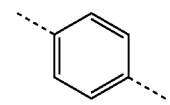

(A2)

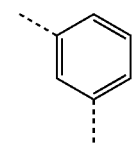

(A3)

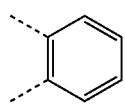

(A4)

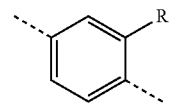

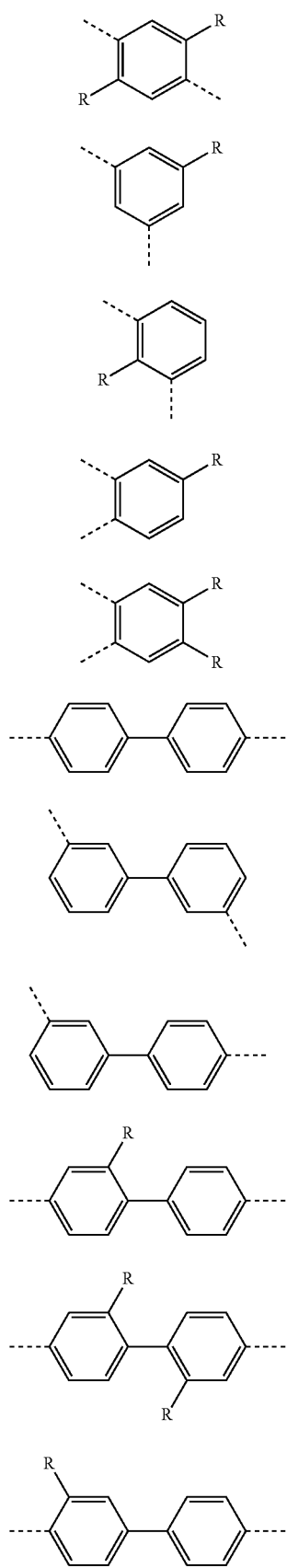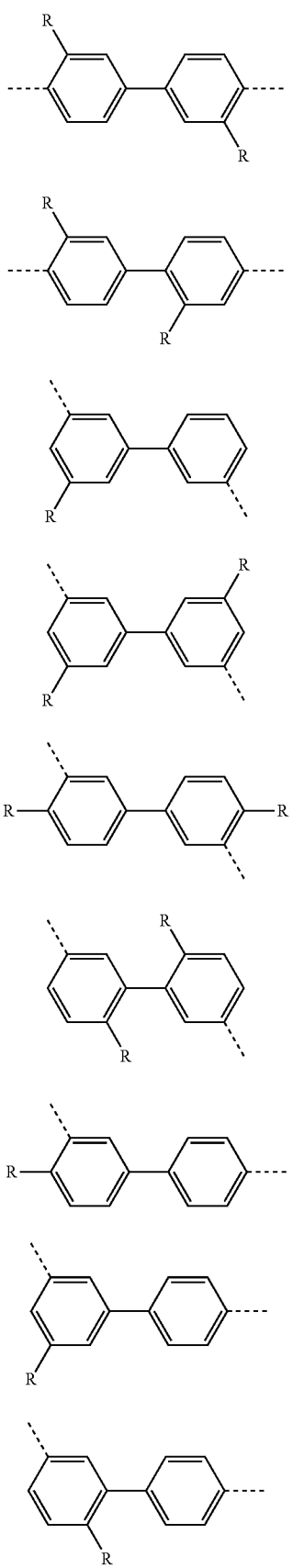

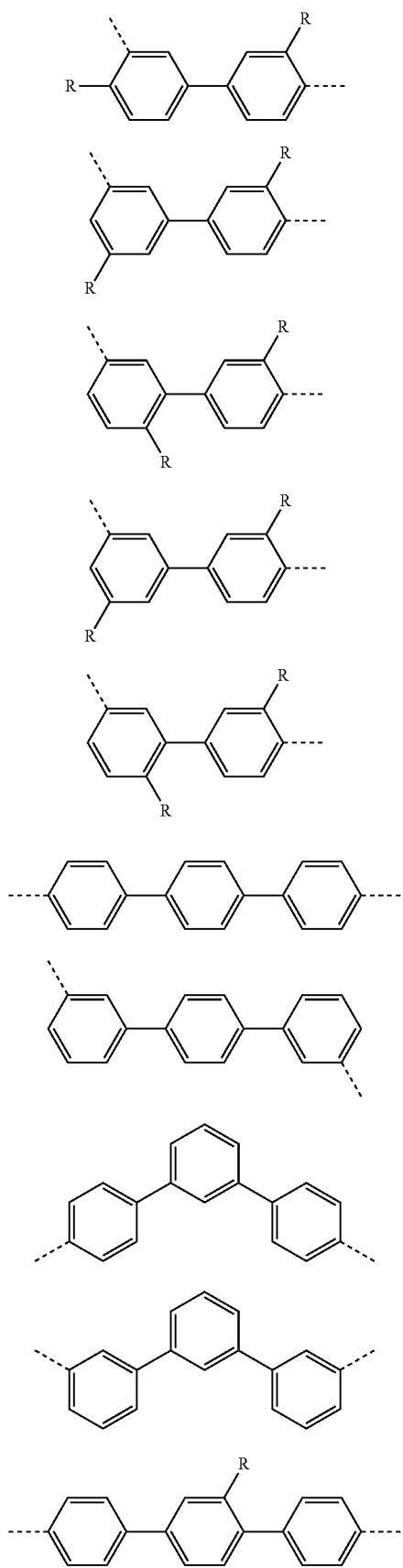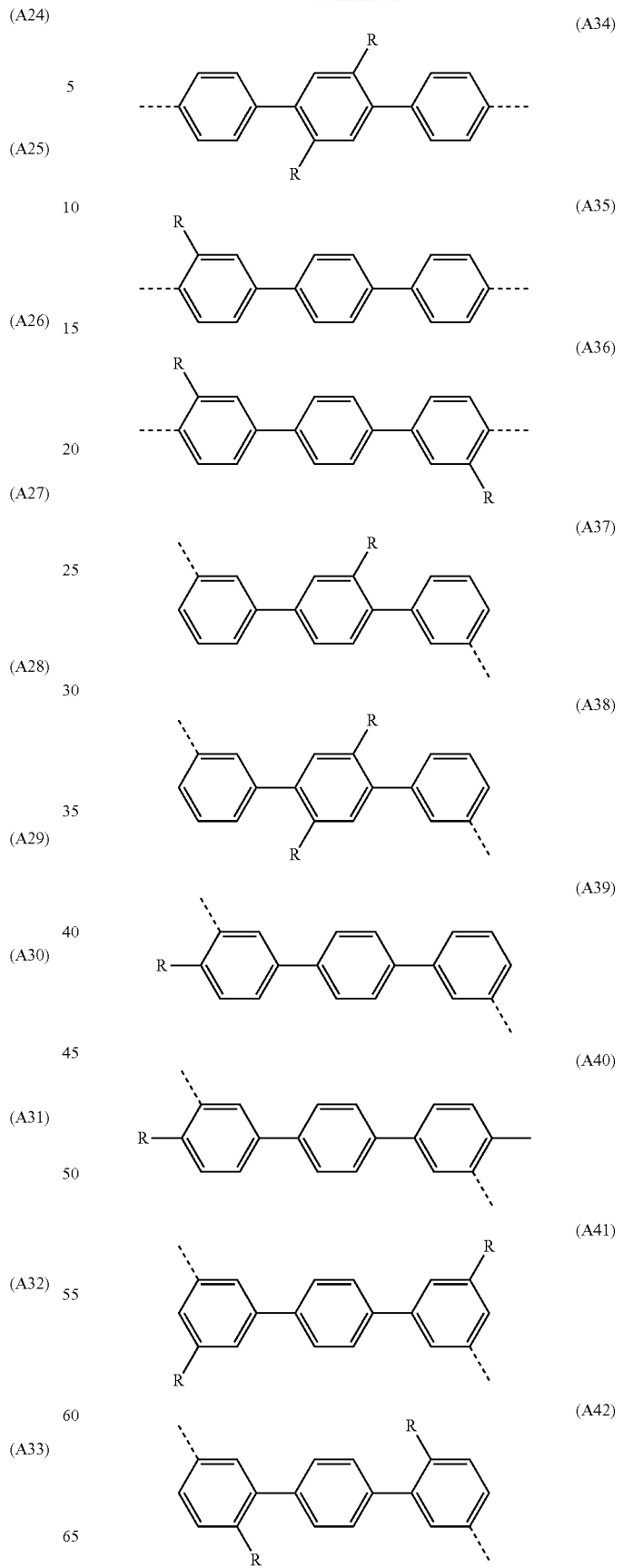

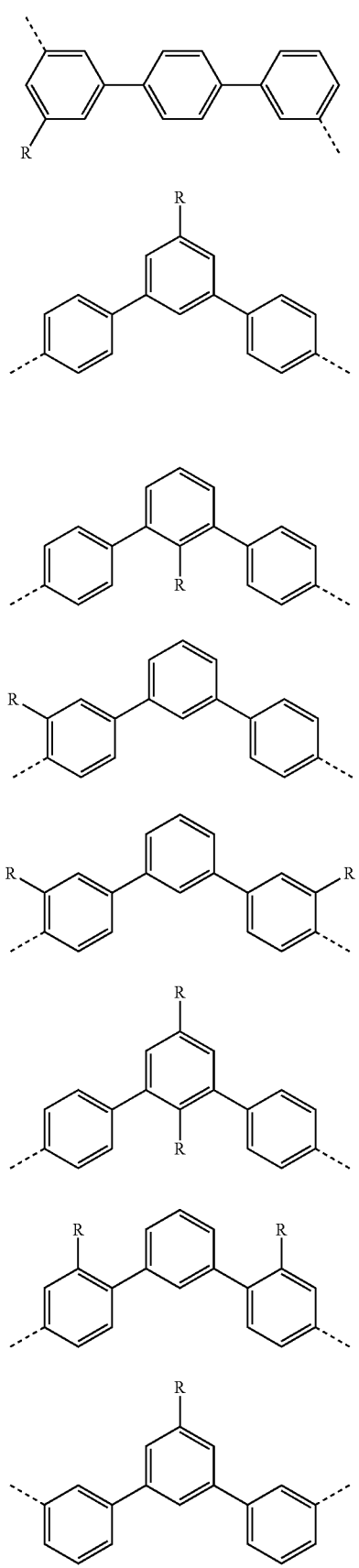
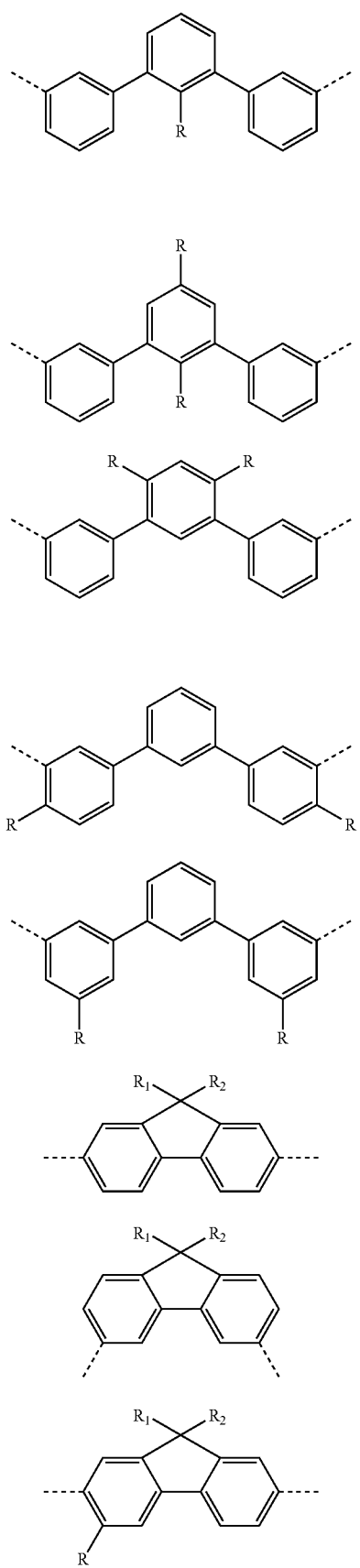

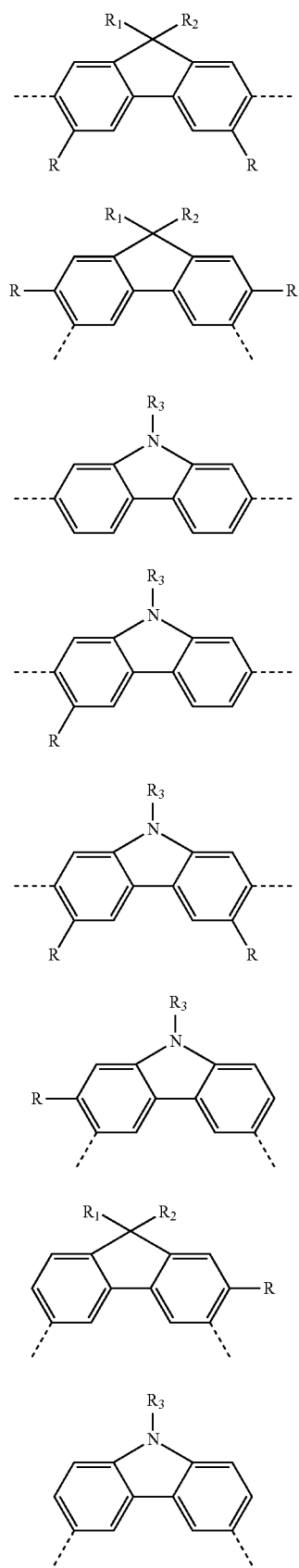

(A59)
(A60)
(A61)
(A62)
(A63)
(A64)
(A65)
(A66)

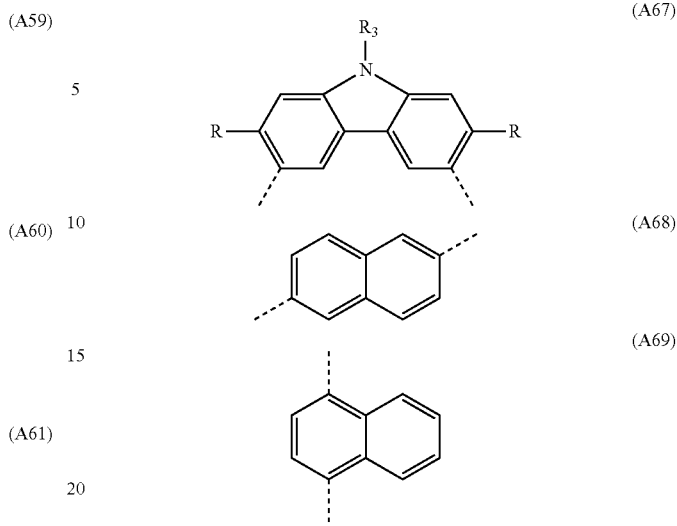

(A67)
(A68)
(A69)

wherein
R=H, R1, R2 or R3;
R1, R2 and R3 are same or independent selected from each other a linear, branched or cyclic alkyl group with 1 to 15 carbon atoms; an alkoxy group with 1 to 15 carbon atoms; an aryl group with 6 to 20 ring-forming carbon atoms; a heteroaryl group with 6 to 20 ring-forming atoms; preferably a linear, branched or cyclic alkyl group with 1 to 10 carbon atoms; an alkoxy group with 1 to 10 carbon atoms; an aryl group with 6 to 15 ring-forming carbon atoms, a heteroaryl group with 6 to 15 ring-forming atoms; further preferred a linear, branched or cyclic alkyl group with 1 to 6 carbon atoms; an alkoxy group with 1 to 5 carbon atoms; an aryl group with 6 to 14 ring-forming carbon atoms; a heteroaryl group with 6 to 14 ring-forming atoms; and more preferred a linear, branched or cyclic alkyl group with 1 to 4 carbon atoms; an alkoxy group with 1 to 2 carbon atoms; an aryl group with 6 to 10 carbon atoms; a heteroaryl group with 6 to 10 ring-forming atoms.

Another aspect is directed to compounds having the chemical formula Ia, Ib and/or Ic, as mentioned above, wherein ET of chemical formula Ia, Ib and/or Ic is selected from a group comprising:

an unsubstituted aryl group with 13 to 40 ring-forming carbon atoms; or a unsubstituted heteroaryl group with 14 to 40 ring-forming atoms, preferably ET is selected from a group comprising anthrancen-2-yl, anthracen-9yl, pyren-1-yl, pyren-2-yl, phenanthren-9-yl, perylen-2-yl, perylen-3-yl, triphenylen-1-yl, triphenylen-2-yl, benzo[f]tetraphen-4-yl, benzo[e]pyren-4-yl, cyclopenta[cd]fluoranthen-6-yl, benzo[f]tetraphen-10-yl, benzo[e]pyren-3-yl, chrysene-1-yl, rubicen-5-yl, rubicen-6-yl, fluoranthen-3-yl, dibenzo[jl]fluoranthen-3-yl, dibenzo[j,1]fluoranthen-9-yl, dibenzo[j,1]fluoranthen-10-yl, benzo[k]tetraphen-1-yl, benzo[k]tetraphen-3-yl, benzo[k]tetraphen-4-yl, benzo[k]tetraphen-7-yl, coronen-1-yl, dibenzo[ghi,mno]fluoranthen-1-yl, dinaptho[2,1-b:1',2'-d]furan-6-yl, acridin-9-yl, dibenzo[c,h]acridin-7-yl; or a substituted aryl group with 13 to 40 ring-forming carbon atoms; or a substituted heteroaryl group with 14 to 40 ring-forming atoms; preferably ET is selected from a group comprising anthrancen-2-yl, anthracen-9yl, pyren-1-yl, pyren-2-yl, phenanthren-9-yl, perylen-2-yl, perylen-3-yl, dinaptho[2,1-b:1',2'-d]furan-6-yl, acridin-9-yl, dibenzo[c,h]acridin-7-yl, fluoren-2-yl, fluoren-3-yl; wherein the substituent of the substituted aryl group or heteroaryl group is selected from a group comprising phenyl, 1-naphthyl, 2-naphthyl, 2-biphenyl, 3-biphenyl, 4-biphenyl, 1-pyrenyl, 2-pyrenyl, 2-phenanthrenyl, 9,9'-fluorenyl or 9,9'-xanthenyl group.

Another aspect is directed to compounds having the chemical formula Ia, Ib and/or Ic, as mentioned above, wherein ET of chemical formula Ia, Ib and/or Ic is selected from the group of B1 to B32:

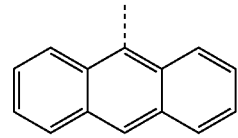
(B1)

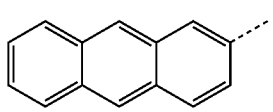
(B2)

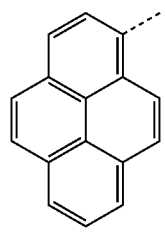
(B3)

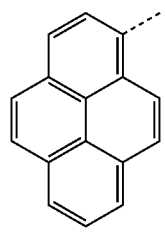
(B4)

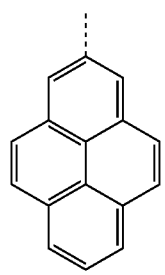
(B5)

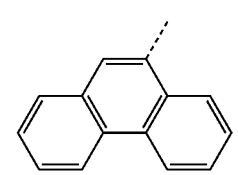
(B6)

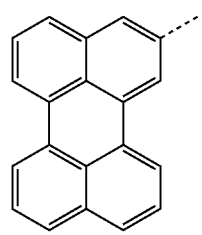
(B7)

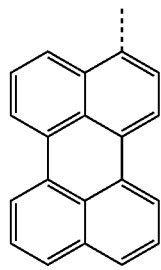
(B8)

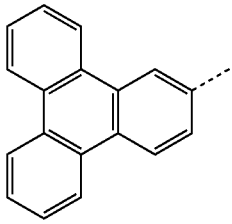
(B9)

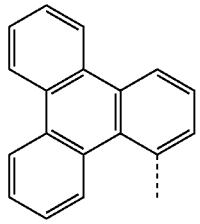
(B10)

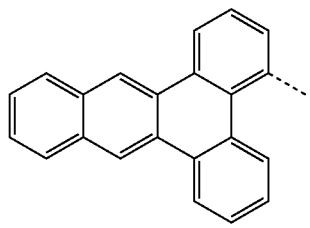
(B11)

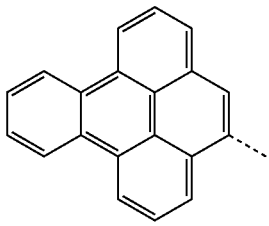
(B12)

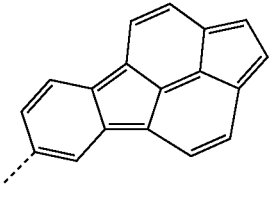
(B13)

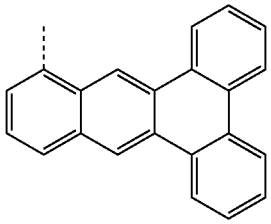

-continued
(B14)
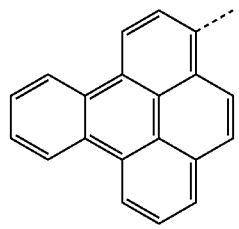
(B15)
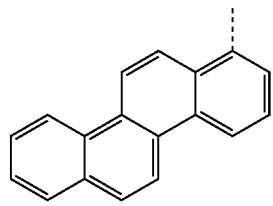
(B16)
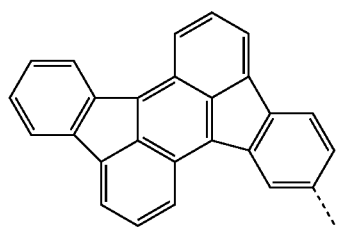
(B17)
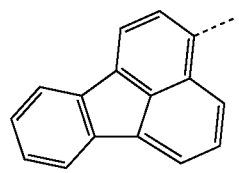
(B18)
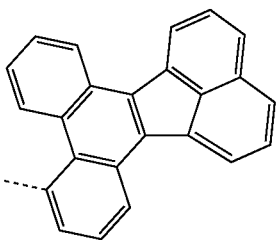
(B19)
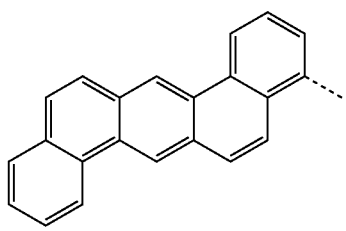
(B20)
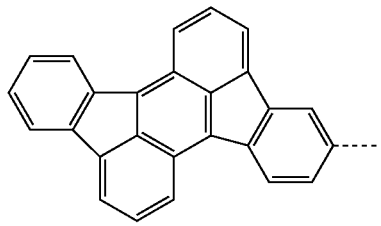
-continued
(B21)
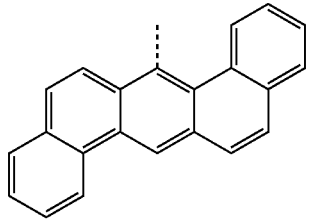
(B22)
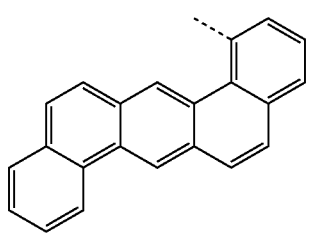
(B23)
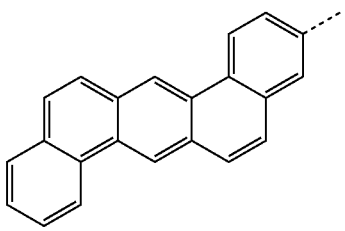
(B24)
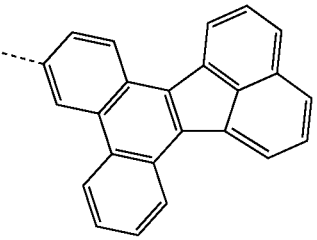
(B25)
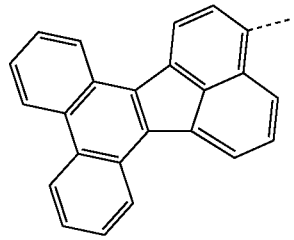
(B26)
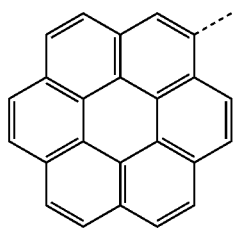

-continued

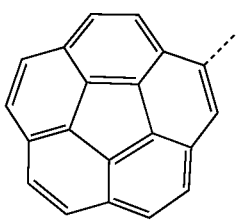
(B27)

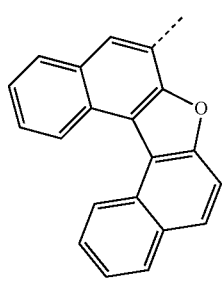
(B28)

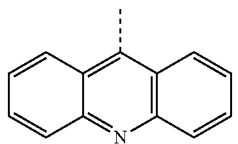
(B29)

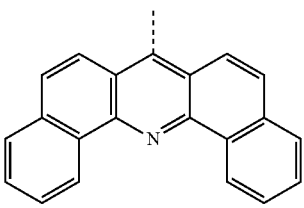
(B30)

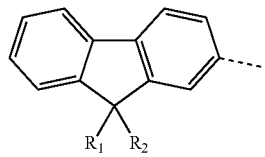
(B31)

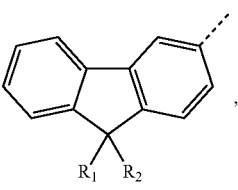
(B32)

, wherein
R1 and R2 are same or independent selected from each other a linear, branched or cyclic alkyl group with 1 to 15 carbon atoms; an alkoxy group with 1 to 15 carbon atoms; an aryl group with 6 to 20 ring-forming carbon atoms; a heteroaryl group with 6 to 20 ring-forming atoms; preferably a linear, branched or cyclic alkyl group with 1 to 10 carbon atoms; an alkoxy group with 1 to 10 carbon atoms; an aryl group with 6 to 15 ring-forming carbon atoms, a heteroaryl group with 6 to 15 ring-forming atoms; further preferred a linear, branched or cyclic alkyl group with 1 to 6 carbon atoms; an alkoxy group with 1 to 5 carbon atoms; an aryl group with 6 to 14 ring-forming carbon atoms; a heteroaryl group with 6 to 14 ring-forming atoms; and more preferred a linear, branched or cyclic alkyl group with 1 to 4 carbon atoms; an alkoxy group with 1 to 2 carbon atoms; an aryl group with 6 to 10 ring-forming carbon atoms; a heteroaryl group with 6 to 10 ring-forming atoms.

Another aspect is directed to compounds having the chemical formula Ia, Ib and/or Ic, as mentioned above, wherein the ET substituent of B1 to B32 is substituted with a phenyl, 1-naphthyl, 2-naphthyl, 2-biphenyl, 3-biphenyl, 4-biphenyl, 1-pyrenyl, 2-pyrenyl, 2-phenanthrenyl, 9,9'-fluorenyl or 9,9'-xanthenyl group.

Another aspect is directed to compounds having the chemical formula:

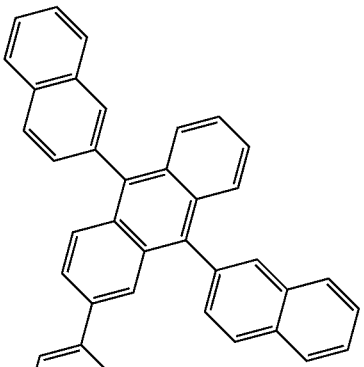
(MX 27)

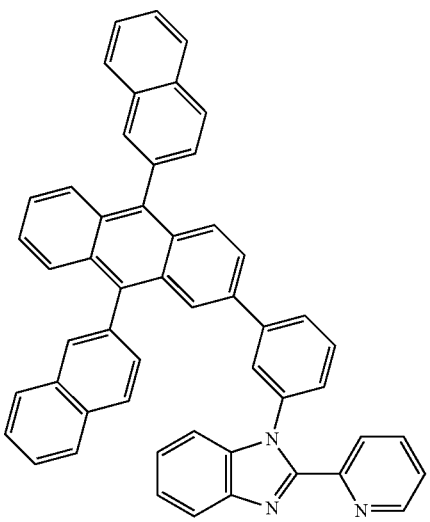
(MX 28)

-continued
(MX 29)
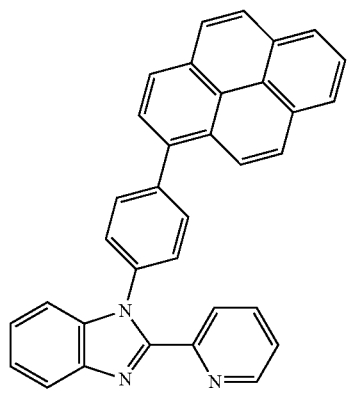
(MX 32)
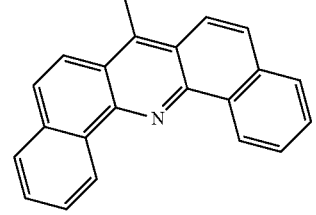
(MX 30)
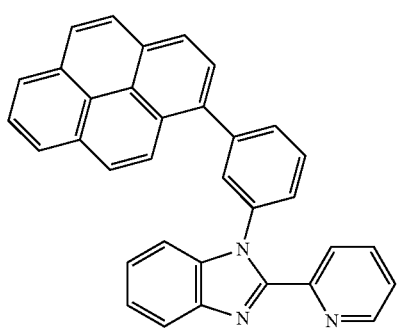
(MX 33)
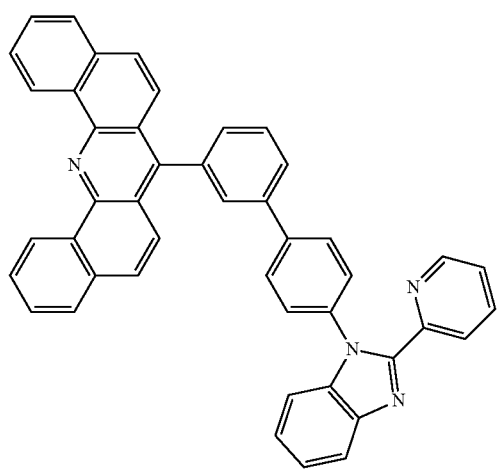
(MX 31)
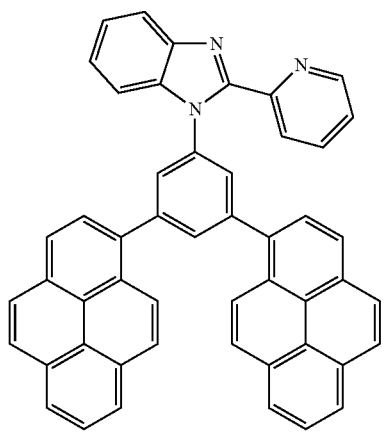
(MX 34)
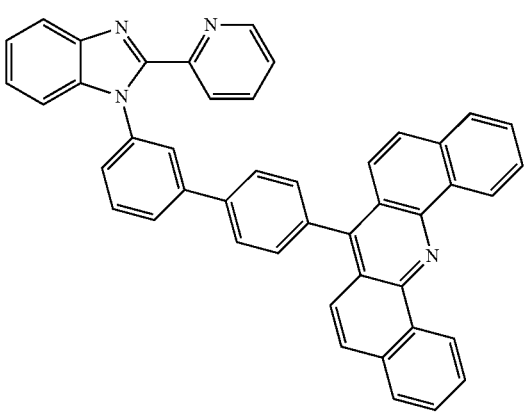

-continued (MX 35)

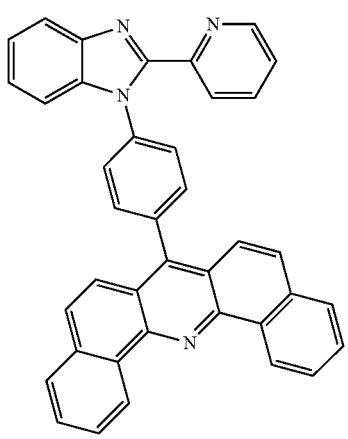

(MX 36)

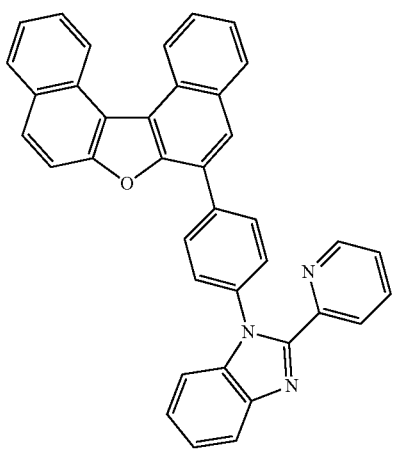

(MX 37)

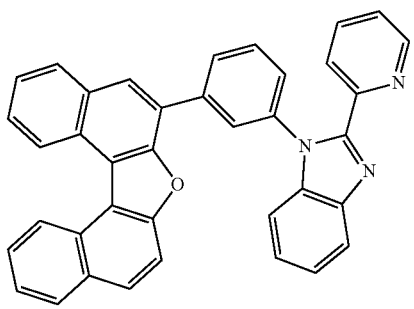

Preferably the compound can be selected from MX27, MX28, MX29, MX30, MX31, MX32, MX33, MX34 and MX35.

Further preferred the compound can be selected from MX32, MX33, MX34 and MX35.

Another aspect is directed to compounds having the chemical formula Ia, Ib and Ic, wherein ET is selected from the group of acridine compounds, acridine compounds substituted with aryl or heteroaryl groups.

More preferred is a chemical formula Ia, Ib and/or Ic, wherein ET is a dibenzo[c,h]acridin group.

Another aspect is directed to compounds having the chemical formula Ib, Ic and excluding formula Ia.

Another aspect is directed to compounds having the chemical formula Ia, Ic and excluding formula Ib.

Another aspect is directed to compounds having the chemical formula Ia, Ib and excluding formula Ic.

Another aspect is directed to compounds having the chemical formula Ia and excluding formula Ib and Ic.

Another aspect is directed to compounds having the chemical formula Ib and excluding formula Ia and Ic.

Another aspect is directed to compounds having the chemical formula Ic and excluding formula Ia and Ib.

Another aspect is directed to compounds having the chemical formula Ia, Ic and excluding formula Ib and wherein ET is an anthracen-9-yl group.

Another aspect is directed to compounds having the chemical formula Ia, Ib and excluding formula Ic and wherein ET is an anthracen-9-yl group.

Another aspect is directed to compounds having the chemical formula Ia and excluding formula Ib and Ic and wherein ET is an anthracen-9-yl group.

Another aspect is directed to compounds having the chemical formula Ib and excluding formula Ia and Ic and wherein ET is an anthracen-9-yl group.

Another aspect is directed to compounds having the chemical formula Ic and excluding formula Ia and Ib and wherein ET is an anthracen-9-yl group.

The compounds of formula Ia, Ib and/or Ic can be used as matrix compounds in an organic semiconductor layer, or charge transport layer, or charge injection layer, preferably in an electron transport layer, or electron injection layer.

Another aspect is directed to the use of the compounds of formula Ia, Ib and/or Ic according to the invention.

The compounds of formula Ia, Ib and/or Ic can be used as matrix compound/s in an organic semiconductor layer, or charge transport layer, or charge injection layer, preferably in an electron transport layer, or electron injection layer.

Another aspect is directed to the method of manufacture of the compounds.

General Synthetic Procedure for Boronic Esters

An oven-dried, three-necked, 1-L, round-bottomed flask fitted with a thermometer, magnetic stirring bar, a pressure-equalizing addition funnel capped with a rubber septum and argon inlet is charged with bromo derivative (45.6 mmol), sealed, evacuated and back filled with dry argon. Anhydrous THF (760 ml) is cannulated directly into the flask, the mixture is stirred until clear solution is formed and cooled to −78° C. (internal temperature). The addition funnel is charged with n-butyllithium solution (2.5M in hexanes, ~50 mmol, 1.1 eq), which is then added dropwise to the stirred reaction mixture while maintaining internal temperature between −78 and −70° C. The addition funnel is washed with two 3-mL portions of tetrahydrofuran and the reaction mixture is stirred an additional 1 hour at −78° C. 2-Isopropoxy-4,4,5,5-tetramethyl-1,3,2-dioxaborolane (72.96 mmol, 1.6 eq) is cannulated into the addition funnel and then added dropwise to the solution at −78° C. Resulting mixture is allowed to reach RT for 1.5 hours, and quenched by addition of methanol. pH is adjusted to ~5 by addition of 2M aqueous solution of hydrochloric acid and evaporated to a dryness using rotational evaporator. Residue is dissolved in chloroform, washed with water and brine, dried over magnesium sulfate and evaporated to dryness. Crude product is purified by re-crystallization or by column chromatography.

General Procedure for Ullmann Coupling Reactions

An oven-dried, two-necked, 1-L, round-bottomed flask equipped with a magnetic stirring bar, a septum and a reflux condenser, fitted with argon inlet, is charged with a 2-(pyridin-2-yl)-1H-benzo[d]imidazole (0.128 mmol, 1 eq.), iodo-aryl (19.2 mmol. 1.5 eq), copper iodide (0.042 mmol, 0.33 eq), 1,10-phenanthroline (0.081 mmol, 0.63eq) and $Cs_2CO_3$ (0.1885 mmol, 1.45 eq). The flask is sealed, evacuated and back filled with argon. Anhydrous DMF (500 ml) is cannulated directly into reaction flask, septum is replaced by stopper, and the mixture is stirred under argon at 150° C.

overnight. Reaction mixture is cooled down to RT, filtered through short Florisil pad (~3 cm) and evaporated to dryness. Residue is dissolved in chloroform, washed with EDTA solution (1%), water (3×) and brine (1×), dried over magnesium sulfate, filtered and evaporated to dryness. Residue is triturated with isopropyl alcohol overnight, filtered and dried. Finally, the solid is re-dissolved in dichloromethane, treated with 5 g of SiO$_2$, filtered and evaporated to dryness.

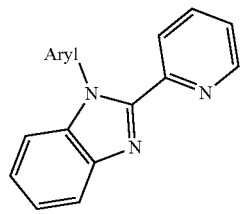

1-(4-bromophenyl)-2-(pyridin-2-yl)-1H-benzo imidazole (1)

Obtained using general Ullmann coupling procedure from 1-iodo-4-bromobenzene

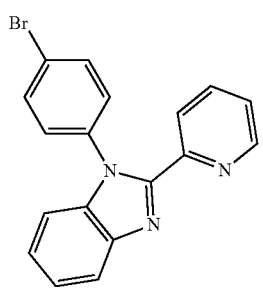 [SMILES: Brc1ccc(-n2c(-c3ccccn3)nc3ccccc32)cc1]

1-(3-bromophenyl)-2-(pyridin-2-yl)-1H-benzo[d] imidazole (2)

Obtained using general Ullmann coupling procedure from 1-iodo-4-bromobenzene

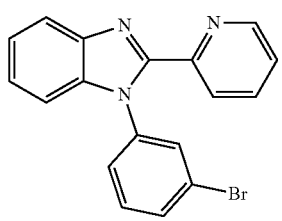 [SMILES: Brc1cccc(-n2c(-c3ccccn3)nc3ccccc32)c1]

7-(4-(2-(pyridin-2-yl)-1H-benzo[d]imidazol-1-yl) phenyl)dibenzo[c,h]acridine

Obtained using general Ullmann coupling procedure from 7-(4-iodophenyl)dibenzo[c,h]acridine

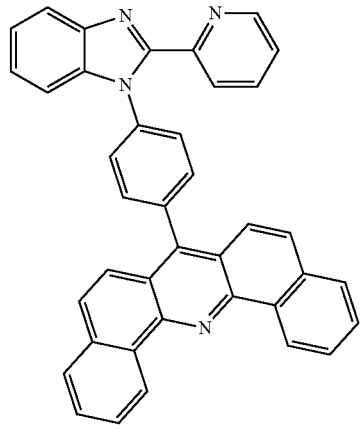 [SMILES: c1ccc(-c2nc3ccccc3n2-c2ccc(-c3c4ccc5ccccc5c4nc4c3ccc3ccccc34)cc2)nc1]

1-(3,5-dibromophenyl)-2-(pyridin-2-yl)-1H-benzo[d] imidazole (3)

2-(pyridin-2-yl)-1H-benzo[d]imidazole (3 g, 15.4 mmol, 1 eq.), 3,5-dibromofluorbenzene (4.3 g, 16.9 mmol, 1.1 eq), Cs$_2$CO$_3$ (9.9 g, 30.6 mmol, 2 eq) and 75 mL dry DMF were combined in a pressure tube and allowed to react for 2 days at 160° C. Then 1 mL (8 mmole, ~0.5 eq.) of 3,5-dibromofluorbenzen and 4.5 g (13.8 mmol, 0.9 eq.) of Cs$_2$CO$_3$ were added and the mixture reacted at 160° C. overnight. Then it is poured into 400 mL water and the precipitate collected by filtration. Crude product is purified by column chromatography yielding desired product as a pale yellow powder.

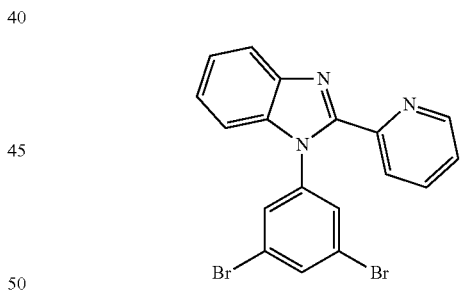

General Procedure for Suzuki Coupling Reactions

A 100-mL, two-necked, round-bottomed flask equipped with a stirring bar, a stopper and a reflux condenser fitted with a nitrogen inlet is charged with (6.8 mmol) boronic ester and benzimidazole-derivative (1) or (2) (7.74 mmol, 1.14 eq). The atmosphere is replaced by argon, deoxygenated glyme (35 ml), 2M aqueous solution of potassium carbonate (12 ml, 3.5 eq, deoxygenated by passing argon stream through the solution for 30 min), and tetrakis(triphenylphosphin)palladium(0) (0.204 mmol, 0.03 eq) are added in this order. The flask is sealed, the mixture is stirred under argon at 95° C. overnight. Aqueous solution of sodium sodium diethylcarbamodithioate sodium diethylcarbamodithioate trihydrate (3%, 50 ml) is added and the mixture is stirred for 30 min at RT. A heterogeneous mixture is poured into 10 fold excess of water, a precipitated product is collected by filtration using a sintered glass filter, washed on the filter with water (3×20 ml) and methanol (2×20 ml) and dried in vacuum at RT. Crude product is then purified by re-crystallization or by column chromatography.

1-(3(9,10-di(naphthalen-2-yl)anthracen-2-(phenyl)-2-(pyrid in-2-yl)-1H-benzo[d]imidazole Obtained using general Suzuki coupling procedure from (9,10-di(naphthalen-2-yl)anthracen-2-yl)boronic acid and (2).

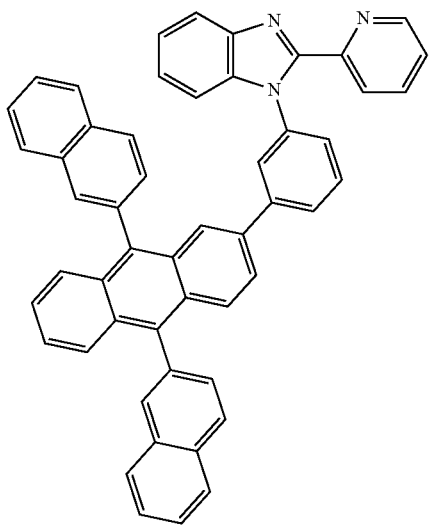 [SMILES: c1ccc(-c2nc3ccccc3n2-c2cccc(-c3ccc4c(-c5ccc6ccccc6c5)c5ccccc5c(-c5ccc6ccccc6c5)c4c3)c2)nc1]

1-(4-(9,10-di(naphthalen-2-yl)anthracen-2-yl)phenyl)-2-(pyridin-2-yl)-1H-benzo[d]imidazole Obtained using general Suzuki coupling procedure from (9,10-di(naphthalen-2-yl)anthracen-2-yl)boronic acid and (1).

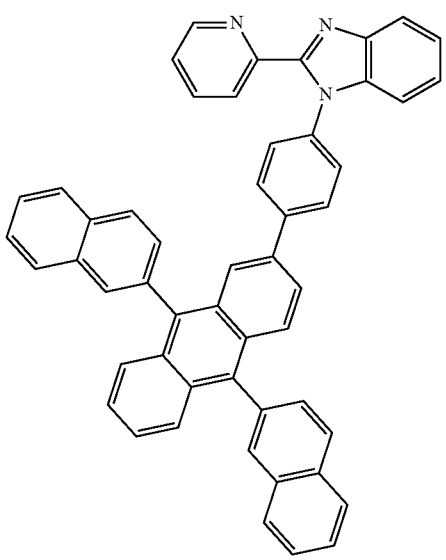 [SMILES: c1ccc(-c2nc3ccccc3n2-c2ccc(-c3ccc4c(-c5ccc6ccccc6c5)c5ccccc5c(-c5ccc6ccccc6c5)c4c3)cc2)nc1]

7-(3'-(2-(pyridin-2-yl)-1H-benzo[d]imidazol-1-yl)-[1,1'-biphenyl]-4-yl)dibenzo[c,h]acridine Obtained using general Suzuki coupling procedure from 7-(4-(4,4,5,5-tetramethyl-1,3,2-dioxaborolan-2-yl)phenyl)dibenzo[c,h]acridine and (2).

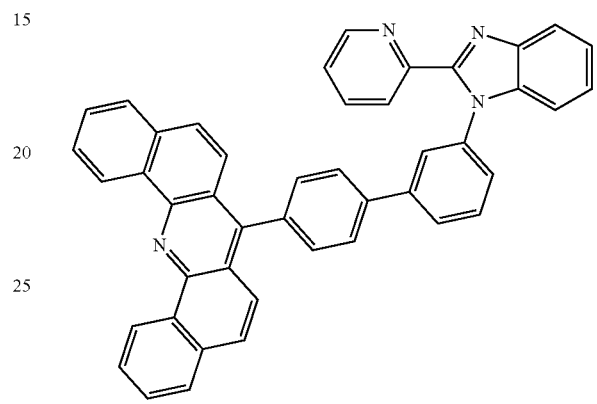

1-(3-(pyren-1-)phenyl)-2-(pyridin-2-yl)-1H-benzo[d]imidazole

Obtained using general Suzuki coupling procedure from pyren-1-ylboronic acid and (2).

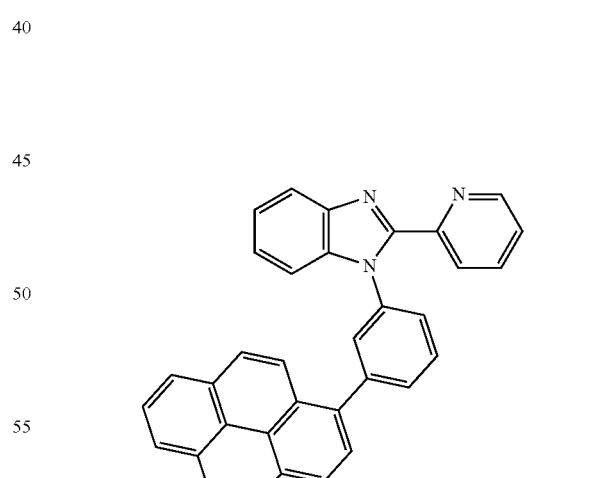

1-(4-(pyren-1-yl)phenyl)-2-(pyridin-2-yl)-1H-benzo[d]imidazole

Obtained using general Suzuki coupling procedure from pyren-1-ylboronic acid and (2).

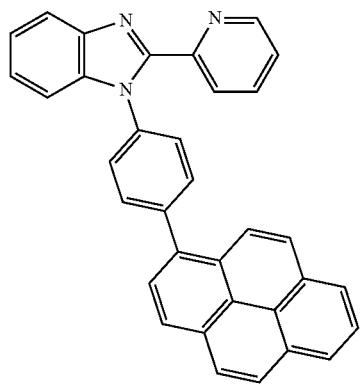 [SMILES: c1ccc(-c2nc3ccccc3n2-c2ccc(-c3ccc4ccc5cccc6ccc3c4c56)cc2)nc1]

1-(3,5-di(pyren-1-yl)phenyl)-2-(pyridin-2-yl)-1H-benzo imidazole

Obtained using general Suzuki coupling procedure from pyren-1-ylboronic acid and (3).

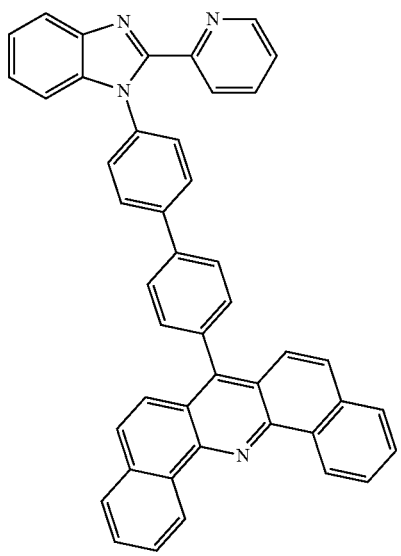

7-(4'-(2-(pyridin-2-yl)-1H-benzo[d]imidazol-1-yl)-[1,1'-biphenyl]-3-yl)-5,6,8,9-tetrahydrodibenzo[c,h]acridine Obtained using general Suzuki coupling procedure from 7-(3-(4,4,5,5-tetramethyl-1,3,2-dioxaborolan-2-yl)phenyl)-5,6,8,9-tetrahydrodibenzo[c,h]acridine and (1).

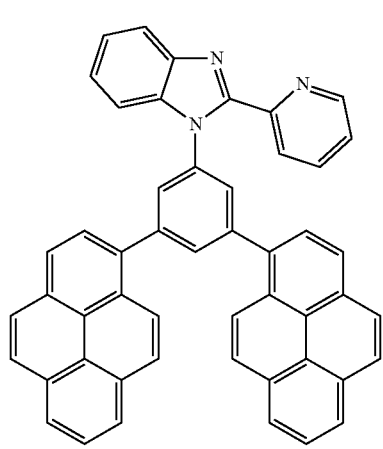 [SMILES: c1ccc(-c2nc3ccccc3n2-c2cc(-c3ccc4ccc5cccc6ccc3c4c56)cc(-c3ccc4ccc5cccc6ccc3c4c56)c2)nc1]

7-(4'-(2-(pyridin-2-yl)-1H-benzo[d]imidazol-1-yl)-[1,1'-biphenyl]-4-yl)dibenzo[c,h]acridine Obtained using general Suzuki coupling procedure from 7-(4-(4,4,5,5-tetramethyl-1,3,2-dioxaborolan-2-yl)phenyl)dibenzo[c,h]acridine and (1).

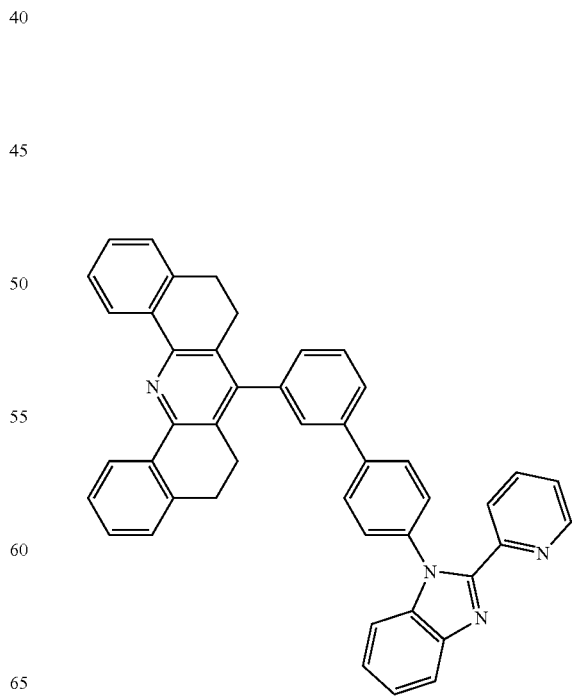

131
7-(4'-(2-(pyridin-2-yl)-1H-benzo[d]imidazol-1-yl)-[1,1'-biphenyl]-3-yl)dibenzo[c,h]acridine

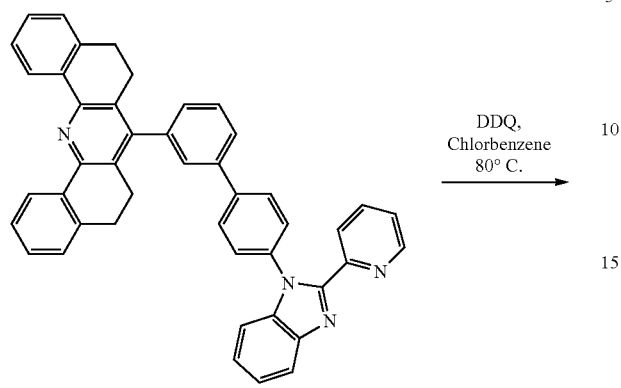

→ DDQ, Chlorbenzene 80° C.

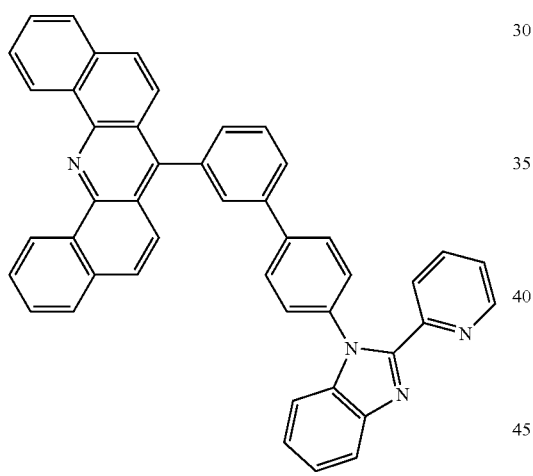

Under argon atmosphere a mixture of 7-(4'-(2-(pyridin-2-yl)-1H-benzo[d]imidazol-1-yl)-[1,1'-biphenyl]-3-yl)-5,6,8,9-tetrahydrodibenzo[c,h]acridine (3.3 g, 5.25 mmol), 4,5-dichloro-3,6-dioxocyclohexa-1,4-diene-1,2-dicarbonitrile (3.58 g, 15.75 mmol, 3 eq) and chlorobenzene(50 ml) is stirred overnight at 80° C. After cooling to room temperature, potassium hydroxide solution in methanol (4% wt., 250 ml) is added and the resulting suspension is stirred at RT for 30 min. Precipitated product was collected by filtration using sintered glass filter, rigorously washed with methanol, hot methanol (3×30 ml) and dried. Crude product is adsorbed on SiO2, which is then placed on the top of SiO2 pad (diameter ~8 cm, thickness ~4 cm) and washed with chlorobenzene (~two column volumes, 500 ml) followed by hot anisole/methanol mixture (4:1 vol.). Anisole fraction was evaporated to dryness yielding desired product as ochre solid.

132
Dinaphtho[2,1-b:1',2'-d]furan

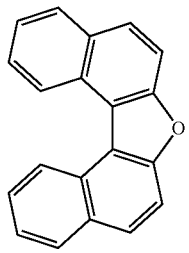 [SMILES: c1ccc2c(c1)ccc1oc3ccc4ccccc4c3c12]

[1,1'-Binaphthalene]-2,2'-diol (30.0 g, 0.105 mol, 1.0 eq.) was placed in a flask and flushed with argon. Anhydrous toluene (300 mL) was added, followed by trifluoromethanesulfonic acid (11.7 mL, 0.210 mol, 2.0 eq.). After further degassing, the mixture was refluxed for 48 hours. After cooling, the organic layer was extracted with water (500 mL), dried over MgSO4, and reduced under vacuum until precipitation. Hexane (300 mL) was then added, and the resulting suspension was stirred for 2 h before being filtered off. This solid was dissolved in DCM, and filtered over silica (elution with hexane/DCM 2:1). The volume of the fraction obtained was reduced to ca. 50 mL, and the resulting crystals were filtered off, yielding the title compound.

2-(Dinaphtho[2,1-b:1',2'-d]furan-6-yl)-4,4,5,5-tetramethyl-1,3,2-dioxaborolane

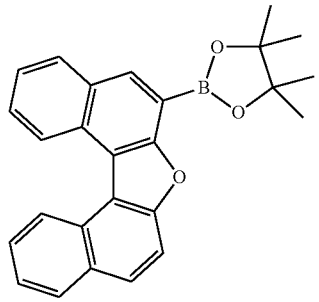 [SMILES: CC1(C)OB(c2cc3ccccc3c3c2oc2ccc4ccccc4c23)OC1(C)C]

Dinaphtho[2,1-b:1',2'-d]furan (14.1 g, 52.6 mmol, 1.0 eq.) was placed in a flask, degassed with argon, and dissolved in anhydrous THF (100 mL). The resulting solution was cooled down to 0° C., and n-butyllithium (1.6M in hexane, 36.2 mL, 57.8 mmol, 1.1 eq.) was added drop wise over a 20-min period. The resulting yellow suspension was stirred overnight at RT, and then quenched by drop wise addition of 2-isopropoxy-4,4,5,5-tetramethyl-1,3,2-dioxaborolane (32.2 mL, 157.8 mmol, 3.0 eq.). After stirring for another 20 h, the mixture was evaporated to dryness to give an orange oil. The crude material was purified by chromatography over silica (elution with hexane/DCM 9:1, then with DCM) yielding the desired material.

1-(4-(dinaphtho[2,1-b:1',2'-d]furan-6-yl)phenyl)-2-(pyridin-2-yl)-1H-benzo[d]imidazole(1)

Obtained using general Suzuki coupling procedure from 2-(dinaphtho[2,1-b:1',2'-d]furan-6-yl)-4,4,5,5-tetramethyl-1,3,2-dioxaborolane and (1)

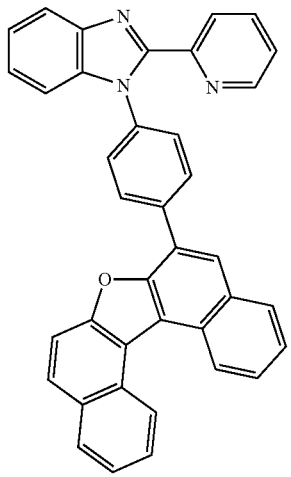 [SMILES: c1ccc(-c2nc3ccccc3n2-c2ccc(-c3cc4ccccc4c4c3oc3ccc5ccccc5c34)cc2)nc1]

1-(3-(Dinaphtho[2,1-b:1',2'-d]furan-6-yl)phenyl)-2-(pyridin-2-yl)-1H-benzo[d]imidazole Obtained using general Suzuki coupling procedure from 2-(dinaphtho[2,1-b:1',2'-d]furan-6-yl)-4,4,5,5-tetramethyl-1,3,2-dioxaborolane and (1)

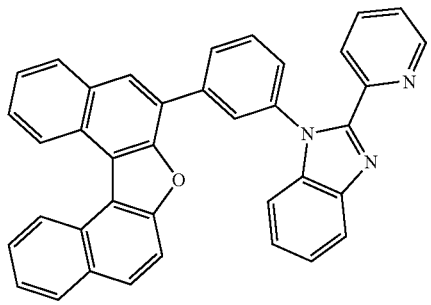 [SMILES: c1ccc(-c2nc3ccccc3n2-c2cccc(-c3cc4ccccc4c4c3oc3ccc5ccccc5c34)c2)nc1]

EXAMPLES

General procedure for ETL stacks of Examples 1 to 17 as well as of Comparative examples 1 to 7, comprising one or two electron transport layers.

Bottom Emission Devices

For bottom emission devices—Examples 1 to 9 and comparative examples 1 to 4, a 15 Ω/cm² glass substrate (available from Corning Co.) with 100 nm Ag was cut to a size of 50 mm×50 mm×0.7 mm, ultrasonically cleaned with isopropyl alcohol for 5 minutes and then with pure water for 5 minutes, and cleaned again with UV ozone for 30 minutes, to prepare a first electrode.

Then, 92 wt.-% of (N4,N4"-di(naphthalen-1-yl)-N4,N4"-diphenyl-[1,1':4',1"-terphenyl]-4,4"-diamine) and 8 wt.-% of 2,2',2"-(cyclopropane-1,2,3-triylidene)tris(2-(p-cyanotetrafluorophenyl)acetonitrile) was vacuum deposited on the ITO electrode, to form a HIL having a thickness of 10 nm. Then (N4,N4"-di(naphthalen-1-yl)-N4,N4"-diphenyl-[1,1':4',1"-terphenyl]-4,4"-diamine) was vacuum deposited on the HIL, to form a HTL having a thickness of 130 nm. 97 wt.-% of ABH113 (Sun Fine Chemicals) as a host and 3 wt.-% of NUBD370 (Sun Fine Chemicals) as a dopant were deposited on the HTL, to form a blue-emitting EML with a thickness of 20 nm.

ETL-Layer Stack of Bottom Emission Device

Then the ETL-layer stack is formed by depositing the first electron transport layer (ETL 1) including a matrix compound according to Example 1 to Example 9 and Comparative examples 1 to 4 by deposing the matrix compound from a first deposition source and the lithium organic complex from a second deposition source directly on the EML The second electron transport layer (ETL 2) for Examples 1 to 9 and Comparative example 3 including a matrix compound is formed by deposing the matrix compound from a third deposition source, since the matrix material is different to the matrix material of the first electron transport layer (ETL 1). For the Comparative examples 1, 2 and 4 only one electron transport layer ETL 1 is formed. Comparative example 1 contains no EIL. Comparative examples 2 and 4 contain an EIL. Comparative example 3 contains a first and second ETL but no EIL.

The wt.-% of the lithium organic complex for the ETL 1 can be taken from Table 6, whereby the wt.-% amount of the matrix compound is added to 100 wt.-%, respectively. That means, that the matrix compound of ETL 1 are added in a wt.-% amount such that the given wt.-% of the lithium organic complex for the ETL 1 and the matrix compound of the ETL 1 are in total 100 wt.-%, based on the weight of the ETL 1. Further, the thickness d (in nm) of the ETL 1 can be taken from Table 6. The cathode was evaporated at ultrahigh vacuum of $10^{-7}$ bar. Therefore, a thermal single co-evaporation of one or several metals was performed with a rate of 0, 1 to 10 nm/s (0.01 to 1 Å/s) in order to generate a homogeneous cathode with a thickness of 5 to 1000 nm. The cathode electrode was formed from 100 nm aluminum.

The OLED stack is protected from ambient conditions by encapsulation of the device with a glass slide. Thereby, a cavity is formed, which includes a getter material for further protection.

The beneficial effect of inventive compounds of formula Ia, Ib and Ic on the performance of bottom emission devices can be seen in Table 6.

Top Emission Devices

For top emission devices—Examples 10 to 17 and comparative examples 5 to 7—the anode electrode was formed from 100 nm silver on glass which was prepared by the same methods as described above.

Then, 92 wt.-% of biphenyl-4-yl(9,9-diphenyl-9H-fluoren-2-yl)-[4-(9-phenyl-9H-carbazol-3-yl)phenyl]-amine (CAS 1242056-42-3) and 8 wt.-% of 2,2',2"-(cyclopropane-1,2,3-triylidene)tris(2-(p-cyanotetrafluorophenyl)acetonitrile) was vacuum deposited on the ITO electrode, to form a HIL having a thickness of 10 nm. Then biphenyl-4-yl(9,9-diphenyl-9H-fluoren-2-yl)-[4-(9-phenyl-9H-carbazol-3-yl)phenyl]amine (CAS 1242056-42-3) was vacuum deposited on the HIL, to form a HTL having a thickness of 130 nm. 97 wt.-% of ABH113 (Sun Fine Chemicals) as a host and 3 wt.-% of NUBD370 (Sun Fine Chemicals) as a dopant were deposited on the HTL, to form a blue-emitting EML with a thickness of 20 nm.

ETL-Layer Stack of Top Emission Device

Then the ETL-layer stack is formed by depositing the first electron transport layer (ETL 1) including a matrix compound according to Example 10 to Example 17 and Comparative examples 5 to 6 by deposing the matrix compound from a first deposition source and the lithium organic complex from a second deposition source directly on the EML.

The second electron transport layer (ETL 2) for Examples 10 to 17 of a matrix compound is formed by deposing the matrix compound from a third deposition source, since the matrix material is different to the matrix material of the first electron transport layer (ETL 1). For the Comparative examples 5 and 7 only one electron transport layer ETL 1 and for comparative example 6 only one electron transport layer ETL 2 is formed. Comparative examples 5 to 7 and Examples 10 to 17 contain an EIL.

The wt.-% of the lithium organic complex for the ETL1 can be taken from Table 7, whereby the wt.-% amount of the matrix compound is added to 100 wt.-%, respectively.

The cathode electrode was formed from 13 nm magnesium (90 vol.-%) and silver (10 vol.-%) alloy, followed by 60 nm biphenyl-4-yl(9,9-diphenyl-9H-fluoren-2-yl)-[4-(9-phenyl-9H-carbazol-3-yl)phenyl]-amine (CAS 1242056-42-3).

The OLED stack is protected from ambient conditions by encapsulation of the device with a glass slide. Thereby, a cavity is formed, which includes a getter material for further protection.

The beneficial effect of inventive compounds of formula Ia, Ib and Ic on the performance of top emission devices can be seen in Table 7.

To assess the performance of the inventive examples compared to the prior art, the current efficiency is measured under ambient conditions (20° C.). Current voltage measurements are performed using a Keithley 2400 sourcemeter, and recorded in V. At 10 mA/cm$^2$ for bottom emission and 15 mA/cm$^2$ for top emission devices, a calibrated spectrometer CAS140 from Instrument Systems is used for measurement of CIE coordinates and brightness in Candela. Lifetime LT of the device is measured at ambient conditions (20° C.) and 15 mA/cm$^2$, using a Keithley 2400 sourcemeter, and recorded in hours. The brightness of the device is measured using a calibrated photo diode. The lifetime LT is defined as the time till the brightness of the device is reduced to 97% of its initial value.

In bottom emission devices, the emission is predominately Lambertian and quantified in percent external quantum efficiency (EQE). To determine the efficiency EQE in % the light output of the device is measured using a calibrated photodiode at 10 mA/cm$^2$.

In top emission devices, the emission is forward directed, non-Lambertian and also highly dependent on the mircocavity. Therefore, the efficiency EQE will be higher compared to bottom emission devices. To determine the efficiency EQE in % the light output of the device is measured using a calibrated photodiode at 15 mA/cm$^2$.

Bottom Emission Device Stacks

In Table 6 bottom emission device stacks without a second ETL or EIL are compared with examples containing a second ETL and EIL.

Comparative example 1 and 2 (see Table 6) contains a single ETL and Comparative example 3 contains a first and a second ETL but no EIL layer are compared with examples 1 and 2 containing a first ETL and second ETL. The voltage of Comparative example 1 is comparable to Comparative example 2, which additionally contains an EIL. Table 6 shows that the voltage of Comparative example 2 is increased by 0.1 V compared to Comparative example 1. As can be seen in Table 6, for the Comparative examples 1 to 3 the voltage is very high and efficiency EQE very low.

Example 1 contains a first and second ETL and EIL. Compared to Comparative example 2, the voltage of Example 1 is decreased by 1 V and the efficiency EQE is improved from 5.9 to 6.4% (see Table 6). Insertion of a second ETL between the first ETL and EIL has a clear beneficial effect on conductivity and efficiency (see Table 6).

Example 2 contains a first and second ETL and an EIL of Li organic complex Li-2. The voltage is improved by 0.8 V and the efficiency EQE is improved from 5.9 to 6.5% compared to Comparative example 2, which does not contain the second ETL (see Table 6). The beneficial effect of the second ETL on conductivity and efficiency is independent of the exact nature of the EIL (see Table 6).

Examples 1 to 9 clearly demonstrate that the new matrix compound according to formula Ia, Ib and Ic provides an beneficial effect on conductivity and efficiency compared to the Comparative examples 1 to 4, see Table 6 below.
Effect of LUMO Level of ETL1 relative to ETL2

In Examples 2 to 5 in Table 6, the LUMO level of the matrix compound in the first ETL is varied between −2.64 eV (Example 2) and −2.36 eV (Example 5). The voltage remains constant at 4 V, while the efficiency EQE is improved from 6.5% in Example 2 to 7.6% in Example 5. The beneficial effect of the second ETL on voltage is independent of the LUMO level of the ETL1. The beneficial effect on the efficiency EQE is most pronounced for layer compositions, for which the offset in LUMO level is not more than 0.15 eV.
Effect of Different Ar Groups on the LUMO Level and Device Performance In Example 5 and 6 in Table 6, the effect of the Ar group on device performance is studied. In Example 5, MX 28 is used as undoped ETL. In MX 28, Ar is meta-phenylene. In Example 6, MX 27 is used and Ar is para-phenylene. The LUMO level for both compounds is the same (−2.51 eV, see Table 4). Use of compound MX 28 with Ar=meta-phenylene results in lower voltage and higher efficiency compared to MX 27 with Ar=para-phenylene (4 vs 4.2 V and 7.6 vs 6.4% EQE, respectively).

Additionally, the effect of different biphenylene Ar groups on device performance has been studied. As can be seen in Table 6, the effect of different stereoisomers of the Ar group on the LUMO level is very small: −2.57 eV for MX 33 compared to −2.59 eV for MX 34.

The effect on device performance is not as pronounced as seen for Ar groups which are selected from phenylene. The efficiency is increased for MX 33 compared to MX 34, see Examples 7 and 8 in Table 6.

In summary, Ar is preferably selected from meta-phenylene group over para-phenylene group. The effect of different stereoisomers of biphenylene groups on device performance is less pronounced.
Effect of Different ET Moieties on the LUMO Level and Device Performance In Example 5 and Example 7, see Table 6, the effect of different ET moieties is investigated. In Example 5, the ET moiety is an anthracen-2-yl ET moiety with a LUMO level of −2.51 eV. In Example 7, dibenzo[c,h]acridin-7-yl ET moiety is used with a LUMO level of −2.57 eV. As can be seen in Table 6, the efficiency is increased and voltage reduced for anthracen-2-yl ET moiety compared to dibenzo[c,h]acridin-7-yl ET moiety. The higher (=closer to vacuum level) the LUMO level of ETL2 compared to ETL1, the lower the voltage and the higher the EQE efficiency.

In Example 9, compound MX 29 with a pyren-1-yl moiety is used. The LUMO level is −2.33 eV, compared to −2.22 eV for MX 12 in ETL1. Voltage and, in particular, efficiency are improved over Comparative Example 4 without ETL2, see Table 6.

In summary, a wide range of different Ar and ET moieties can be employed to reduce the voltage and increase the EQE efficiency of OLEDs. In particular, this approach is successful even for a wide range of LUMO levels of the matrix compounds used in ETL1 and inventive compounds of formula Ia, Ib and Ic used in ETL2. Additionally, various electron injection layers can be used. These features are particularly beneficial for mass production of organic electronic devices, as the properties of compounds of formula Ia, Ib and Ic can be fine-tuned in terms of synthetic ease and cost without having to redesign the remaining device stack.

TABLE 6

Voltage, external quantum efficiency (EQE) and lifetime of bottom emission OLEDs (V, EQE at 10 mA/cm$^2$; LT at 15 mA/cm$^2$)

| | ETL1 | wt.-% Li organic complex*[1] | d (ETL1)/ nm | ETL2*[2] | d (ETL2)/ nm | EIL | wt.-% Li organic complex*[3] | d (EIL)/ nm | V at 10 mA/cm$^2$/V | EQE*[4]/ % | LT at 15 mA/cm2 (RT)/h |
|---|---|---|---|---|---|---|---|---|---|---|---|
| Comparative example 1 | MX 11: Li-2 | 55 | 36 | — | — | — | — | — | 4.6 | 6 | 150 |
| Comparative example 2 | MX 11: Li-2 | 55 | 36 | — | — | MX 12: Li-1 | 30 | 3 | 4.7 | 5.9 | 110 |
| Comparative example 3 | MX 11: Li-2 | 55 | 10 | MX 28 | 25 | — | — | — | 8.9 | 3.9 | — |
| Comparative example 4 | MX 12: Li-2 | 50 | 36 | — | — | Li-2 | — | 1 | 4.6 | 5.7 | 300 |
| Example 1 | MX 11: Li-2 | 55 | 10 | MX 28 | 25 | MX 12: Li-1 | 30 | 3 | 3.7 | 6.4 | 60 |
| Example 2 | MX 11: Li-2 | 55 | 10 | MX 28 | 25 | Li-2 | — | 1 | 3.9 | 6.5 | 55 |
| Example 3 | MX 5: Li-2 | 50 | 10 | MX 28 | 25 | Li-2 | — | 1 | 3.9 | 7.2 | 25 |
| Example 4 | MX 6: Li-2 | 50 | 10 | MX 28 | 25 | Li-2 | — | 1 | 3.9 | 6.9 | 35 |
| Example 5 | MX 8: Li-2 | 50 | 10 | MX 28 | 25 | Li-2 | — | 1 | 4 | 7.6 | 40 |
| Example 6 | MX 8: Li-2 | 50 | 10 | MX 27 | 25 | Li-2 | — | 1 | 4.2 | 6.4 | 65 |
| Example 7 | MX 8: Li-2 | 50 | 10 | MX 33 | 25 | Li-2 | — | 1 | 4.2 | 6.9 | 40 |
| Example 8 | MX 8: Li-2 | 50 | 10 | MX 34 | 25 | Li-2 | — | 1 | 4.1 | 6.7 | 60 |
| Example 9 | MX 12: Li-2 | 50 | 5 | MX 29 | 30 | Li-2 | — | 1 | 4.4 | 6.1 | 10 |

*[1] the wt.-% of the matrix compound MX and the wt.-% of the lithium organic complex are in total 100 wt.-% based on the weight of the ETL1.
*[2] the wt.-% of the matrix compound of the second electron transport layer ETL2 is 100 wt.-% based on the weight of the ETL2.
*[3] the wt.-% of the matrix compound MX and the wt.-% of the lithium organic complex are in total 100 wt.-% based on the weight of the EIL.
*[4] detecting the light output efficiency with a calibrated photo diode.

Top Emission Device Stacks

In Table 7 top emission device stacks without a second ETL are compared with examples containing a second ETL.

In comparative example 5, see Table 7 below, the device contains a first ETL and electron injection layer but does not contain an undoped second ETL. The first ETL comprises matrix compound MX 26 doped with Li organic complex Li-2. The voltage is 4.8 V and the EQE efficiency is 12.1%.

In comparative example 6, see Table 7 below, the device contains an undoped ETL of MX 33 and an electron injection layer but no first ETL. The voltage is 5.3 V and the EQE efficiency is 9.8%.

In Example 10, see Table 7 below, the device contains a first ETL comprising MX 26 doped with Li organic complex Li-2, a second ETL containing MX 33, and an electron injection layer. The voltage is improved by 0.5 V compared to comparative example 5 and by 1 V compared to comparative example 6. The EQE efficiency is improved from 12.1 to 12.4% compared to comparative example 5 and improved from 9.8 to 12.4% compared to comparative example 6.

The undoped second ETL comprising compounds of formula Ia, Ib and Ic have a clear beneficial effect on voltage and efficiency in top emission devices compared to the comparative examples 5 to 7.

TABLE 7

Voltage, external quantum efficiency (EQE) and lifetime of top emission OLEDs (V, EQE at 15 mA/cm²; LT at 15 mA/cm²)

| | ETL1 | wt.-% Li organic complex*[1] | d (ETL1)/ nm | ETL2*[2] | d (ETL2)/ nm | EIL | wt.-% Li organic complex*[3] | d (EIL)/ nm | V at 10 mA/cm²/V | EQE*[4]/ % | LT at 15 mA/cm2 (RT)/h |
|---|---|---|---|---|---|---|---|---|---|---|---|
| Comparative example 5 | MX 26: Li-2 | 50 | 36 | — | — | LiQ | 100 | 1.5 | 4.8 | 12.1 | 58 |
| Comparative example 6 | — | — | — | MX 33 | 36 | LiQ | 100 | 1.5 | 5.3 | 9.8 | 1 |
| Example 10 | MX 26: Li-2 | 50 | 12 | MX 33 | 21 | LiQ | 100 | 1.5 | 4.3 | 12.4 | 12 |
| Example 11 | MX 26: Li-2 | 50 | 10 | MX 33 | 24 | LiQ | 100 | 1.5 | 4.2 | 12.3 | 6 |
| Example 12 | MX 26: Li-2 | 50 | 6 | MX 33 | 27 | LiQ | 100 | 1.5 | 4.2 | 13.2 | 3 |
| Example 13 | MX 26: Li-2 | 50 | 4 | MX 33 | 30 | LiQ | 100 | 1.5 | 4 | 12.6 | 6 |
| Comparative example 7 | MX 25: Li-2 | 50 | 36 | — | — | LiQ | 100 | 1.5 | 4.9 | 11.4 | 78 |
| Example 14 | MX 25: Li-2 | 50 | 13 | MX 33 | 21 | LiQ | 100 | 1.5 | 4.3 | 12.8 | 5 |
| Example 15 | MX 25: Li-2 | 50 | 10 | MX 33 | 24 | LiQ | 100 | 1.5 | 4.3 | 13 | 3 |
| Example 16 | MX 25: Li-2 | 50 | 6 | MX 33 | 28 | LiQ | 100 | 1.5 | 4.2 | 13 | 3 |
| Example 17 | MX 25: Li-2 | 50 | 3 | MX 33 | 30 | LiQ | 100 | 1.5 | 4.2 | 13 | 1 |

*[1] the wt.-% of the matrix compound MX and the wt.-% of the lithium organic complex are in total 100 wt.-% based on the weight of the ETL1.
*[2] the wt.-% of the matrix compound of the second electron transport layer ETL2 is 100 wt.-% based on the weight of the ETL2.
*[3] the wt.-% of the matrix compound MX and the wt.-% of the lithium organic complex are in total 100 wt.-% based on the weight of the EIL.
*[4] detecting the light output efficiency with a calibrated photo diode.

Effect of the Thickness of ETL1 and ETL2 on Device Performance in Top Emission Devices In Example 10 to 13, the effect of thickness of ETL1 and ETL2 on voltage and efficiency is summarized. The thickness of ETL1 is step-wise reduced from 12 to 4 nm and the thickness of ETL2 is step-wise increased from 21 to 30 nm. As can be seen in Table 7, the voltage is further reduced the thinner ETL1 and the thicker ETL2. The sum of the thickness of ETL1 and ETL2 is kept constant at approx. 34 nm. The lowest voltage is achieved for 4 nm ETL1 and 30 nm ETL2 (Example 13). The highest EQE efficiency is achieved for 6 nm ETL1 and 27 nm ETL2 (Example 12).

In summary, the voltage can be reduced by nearly a volt compared to the state of the art through the inventive device stack. The EQE efficiency can be improved from 12.1 to 13.2% by tailoring the thickness of the ETL1 and ETL2 in the inventive device stack.

The effect of the thickness of ETL1 and ETL2 has also been tested for a different composition of ETL1.

In comparative example 7, the ETL1 contains matrix compound MX 25 and the same Li metal organic complex as in comparative examples 5 and 6. The voltage is 4.9 V and the EQE efficiency 11.4%.

In example 14, the same device stack is used as for comparative example 7, but with an undoped ETL2 using inventive compound of formula (1a, 1b or 1c). The voltage is improved by 0.6 V and the EQE efficiency is increased from 11.4 to 12.8%.

In example 14 to 17, the thickness of the ETL1 is step-wise reduced from 13 to 3 nm and the thickness of ETL2 increased from 21 to 30 nm. The sum of the ETL1 and ETL2 thickness is kept constant at approx. 34 nm. As can be seen in Table 6, the voltage is stable at 4.2 to 4.3. The EQE efficiency also remains stable at 12.8 to 13% EQE.

In summary, the voltage and efficiency remain stable over a wide range of ETL1 and ETL2 thicknesses as long as the sum of ETL1 and ETL2 thickness are kept in the same range.

These features are very important for mass production of organic electronic devices, as deviations from the target thickness of ETL1 have little effect on performance, if compensated through the ETL2 thickness. Therefore, a wide process window is given for the ETL1 thickness.

Effect of the LUMO Level of ETL1 on Device Performance in Top Emission Devices

In example 10 and 14, two devices with different ETL1 compositions are compared. In example 10, the LUMO level of the matrix compound in ETL1 is −2.46 V. In example 14, the LUMO level of the matrix compound in ETL1 is −2.59 V. As can be seen, identical voltages can be achieved even for very different LUMO levels of ETL1. The EQE efficiency is improved over the state of the art in both examples.

In summary, the inventive device stack using compounds according to chemical formula Ia, Ib and Ic in the undoped second ETL results in reduced voltage and increased EQE efficiency for a wide range of LUMO levels in ETL1 and ETL2. Additionally, the properties of the electron injection layer have little impact on performance. The beneficial effect is observed over a wide range of ETL layer thickness and effective both in bottom and top emission devices. In conclusion, the inventive device stack comprising compounds according to chemical formula Ia, Ib and Ic offer significant advantages for mass production.

Measurement of Energy Levels of ETL2 Relative to ETL1

Redox potentials are determined via cyclic voltammetry in tetrahydrofurane (THF), using the Ferrocene/Ferrocenium (Fc/Fc$^+$) redox couple as internal reference. A simple rule is very often used for the conversion of redox potentials into electron affinities and ionization potential: IP (in eV)=4.84 eV+e*Eox (wherein Eox is given in volts vs. ferrocene/ferrocenium (Fc/Fc$^+$) and EA (in eV)=4.84 eV+e*Ered (Ered is given in volts vs. Fc/Fc$^+$) respectively (see B. W. D'Andrade, Org. Electron. 6, 11-20 (2005)), e* is the elemental charge. Processes are known for the correction of the electrochemical potentials in the case other reference electrodes or other redox pairs are used (see A. J. Bard, L. R. Faulkner, "Electrochemical Methods: Fundamentals and Applications", Wiley, 2. Ausgabe 2000). The information about the influence of the solution used can be found in N. G. Connelly et al., Chem. Rev. 96, 877 (1996). It is common practice, even if not exactly correct to use the terms "energy of the HOMO" $E_{(HOMO)}$ and "energy of the LUMO" $E_{(LUMO)}$ respectively as synonyms for the ionization energy and electron affinity (Koopmans theorem). It has to be taken in consideration, that the ionization potentials and the electron affinities are given in such a way that a larger value represents a stronger binding of a released or respectively of an absorbed electron. The energy scale of the frontier molecular orbitals (HOMO, LUMO) is opposed to this. Therefore, in a rough approximation, is valid: $IP=-E_{(HOMO)}$ and $EA=E_{(LUMO)}$. The given potentials correspond to the solid-state potentials.

TABLE 8

LUMO energy levels of matrix compounds

| Matrix compound | LUMO vs Fc/Fc+ in THF/V | LUMO/ eV |
| --- | --- | --- |
| MX 11 | −2.2 | −2.64 |
| MX 12 | −2.62 | −2.22 |
| MX 25 | −2.25 | −2.59 |
| MX 6 | −2.42 | −2.42 |
| MX 8 | −2.48 | −2.36 |
| MX 5 | −2.38 | −2.46 |
| MX 28 | −2.33 | −2.51 |
| MX 27 | −2.33 | −2.51 |
| MX 34 | −2.25 | −2.59 |
| MX 29 | −2.51 | −2.33 |
| MX 33 | −2.27 | −2.57 |
| MX 26 | −2.38 | −2.46 |
| MX 36 | −2.54 | −2.3 |

Technical Effect of the Invention

Devices containing compounds of chemical formula Ia, Ib and/or Ic in the undoped second ETL according to the present inventions show a significantly lower voltage and improved EQE compared to prior art devices. A device comprising organic light-emitting diodes (OLED) according to the present invention can be driven at lower voltage while maintaining the same brightness. Further, the power consumption is reduced and the battery life can be extended, for example in a portable electronic device or display.

The ETL layer stack according to this invention may also be employed for other emission colors, for example green, red, and white-light emitting devices. From the foregoing detailed description and examples, it will be evident that modifications and variations can be made to the compositions and methods of the invention without departing from the spirit and scope of the invention. Therefore, it is intended that all modifications and/or combinations of embodiments made to the invention without departing from the spirit and scope of the invention come within the scope of the appended claims.

The invention claimed is:

1. An organic light-emitting diode (OLED) comprising an emission layer and an electron transport layer stack of at least two electron transport layers, wherein a first electron transport layer and a second electron transport layer comprises at least one matrix compound, wherein the matrix compound or compounds of the first electron transport layer is/are different to the matrix compound or compounds of the second electron transport layer; and in addition, the first electron transport layer comprises a dopant of a lithium halide and/or lithium organic complex; and the second electron transport layer is free of a dopant; wherein at least one matrix compound of the second electron transport layer has the chemical formula Ia, Ib and/or Ic:

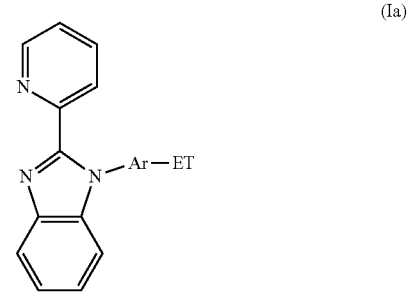

(Ia)

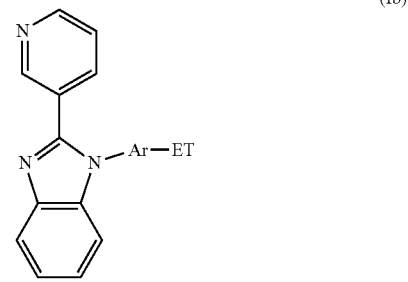

(Ib)

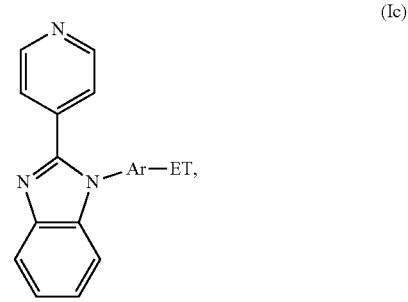

(Ic)

wherein

Ar=substituted or unsubstituted arylene with 6 to 20 ring-forming carbon atoms; or carbazolylene;

ET=substituted or unsubstituted aryl group with 13 to 40 ring-forming carbon atoms; or a substituted or unsubstituted heteroaryl group with 14 to 40 ring-forming atoms.

2. The OLED according to claim 1, wherein the matrix compound or compounds of the first electron transport layer is/are a phosphine oxide compound substituted with aryl, heteroaryl or alkyl groups.

3. The OILED according to claim 1, wherein the electron transport layer stack has three electron transport layers, wherein the first electron transport layer and the third electron transport layer comprise the same or different matrix compound and the same or different dopant; and the second electron transport layer contains a matrix compound or matrix compounds that differs from the matrix compound or matrix compounds of the first and third transport layers and the second electron transport layer is free of a dopant.

4. The OLED according to claim 3, wherein the matrix compound of the first electron transport layer, or of the first electron transport layer and of the third electron transport layer, is selected from a phosphine oxide compound substituted with aryl, heteroaryl or alkyl groups.

5. The OLED according to claim 3, wherein
the first electron transport layer comprises a matrix material selected from the group comprising
a phosphine oxide compound substituted with aryl, heteroaryl or alkyl groups;
the second electron transport layer comprises a matrix material having the chemical formula Ia, Ib and/or Ic;
the third electron transport layer comprises a matrix material selected from the group comprising
a phosphine oxide compound substituted with aryl heteroaryl or alkyl groups; and/or
a benzimidazole compound substituted with aryl, heteroaryl or alkyl groups.

6. The OLED according to claim 1, wherein
the second electron transport layer comprises at least one matrix material having the chemical formula Ia, Ib and/or Ic:

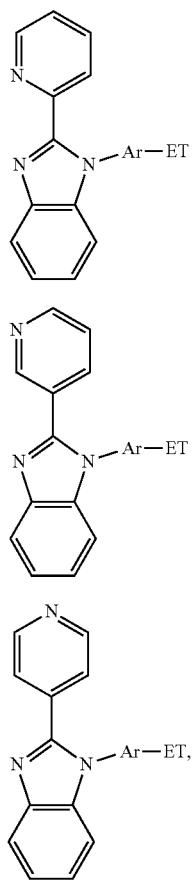

wherein
Ar=substituted or unsubstituted arylene with 6 to 18 ring-forming carbon atoms; or carbazolylene;
ET=substituted or unsubstituted aryl group with 14 to 26 ring-forming carbon atoms; or a substituted or unsubstituted heteroaryl group with 20 to 24 ring-forming atoms.

7. The OILED according to claim 1, wherein Ar of chemical formula Ia, Ib and Ic is selected from the group of:
unsubstituted arylene:
o-phenylene, m-phenylene, p-phenylene, biphenyl-2,2'-diyl, biphenyl-3,3'diyl, biphenyl-4,4'diyl, biphenyl-3,4'-diyl, p-terphenyl-4,4'-diyl, p-terphenyl-3,3'-diyl, p-terphenyl-2,2'-diyl, m-terphenyl-4,4'-diyl, m-terphenyl-3,3'-diyl, m-terphenyl-2,2'-diyl, o-terphenyl-4,4'-diyl, o-terphenyl-3,3'-diyl, o-terphenyl-2,2'-diyl; naphthalen-2,6-diyl, naphthalen-1,4-diyl; or
substituted arylene or carbazolylene:
o-phenylene, m-phenylene, p-phenylene, biphenyl-2,2'diyl, biphenyl-3,3'diyl, biphenyl-4,4'diyl, biphenyl-3,4'-diyl, fluoren-2,7-diyl, fluoren-3,6-diyl, carbazolen-3,6-diyl, carbazolen-2,7-diyl, p-terphenyl-4,4'-diyl, p-terphenyl-3,3'-diyl, p-terphenyl-2,2'-diyl, m-terphenyl-4,4'-diyl, m-terphenyl-3,3'-diyl, m-terphenyl-2,2'-diyl, o-terphenyl-4,4'-diyl, o-terphenyl-3,3'-diyl, o-terphenyl-2,2'-diyl; naphthalen-2,6-diyl, naphthalen-1,4-diyl; and
wherein the substituent of the substituted arylene or carbazolylene is selected from the group of an alkyl group with 1 to 15 carbon atoms.

8. The OILED according to claim 1, wherein Ar of chemical formula Ia, Ib and/or Ic is selected from the group of A1 to A69:

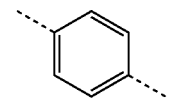
(A1)

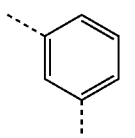
(A2)

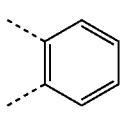
(A3)

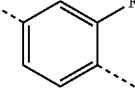
(A4)

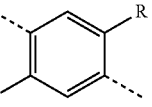
(A5)

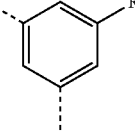
(A6)

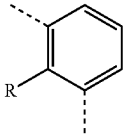
(A7)

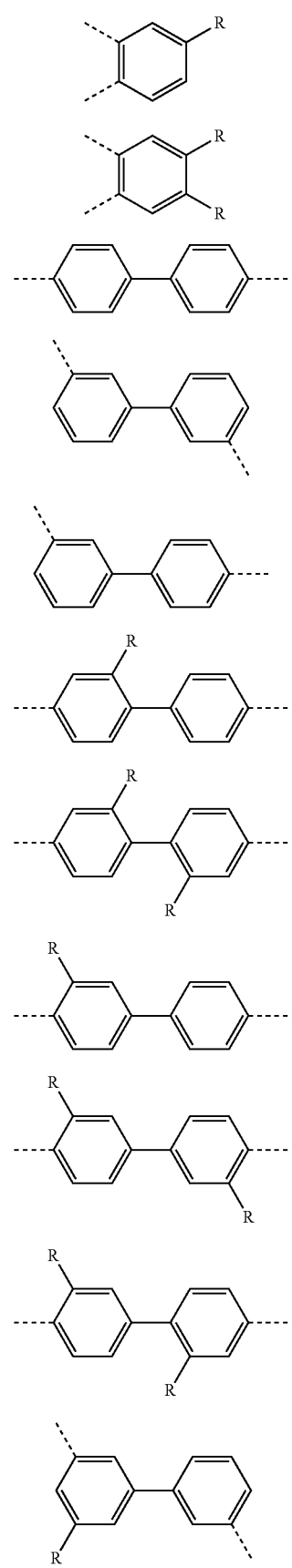
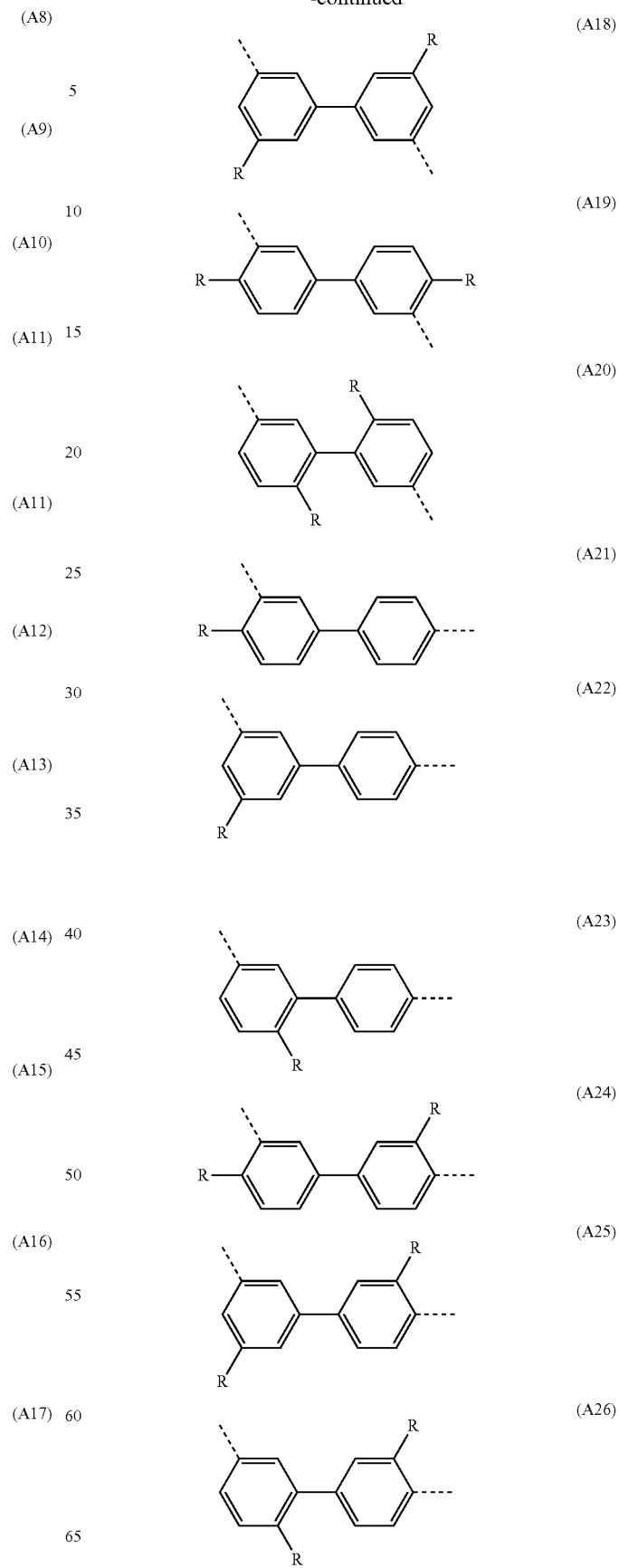

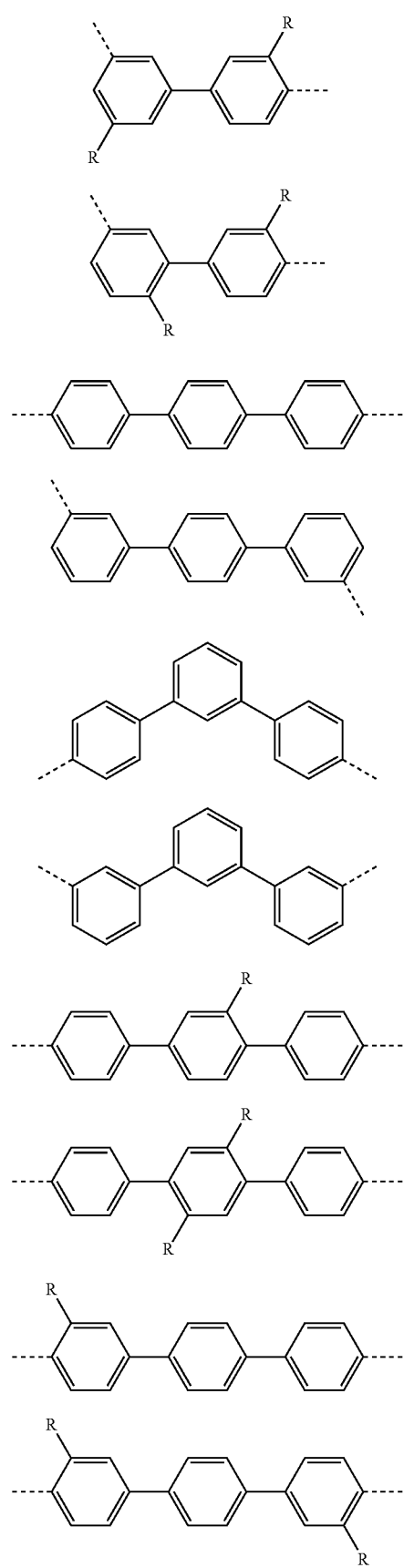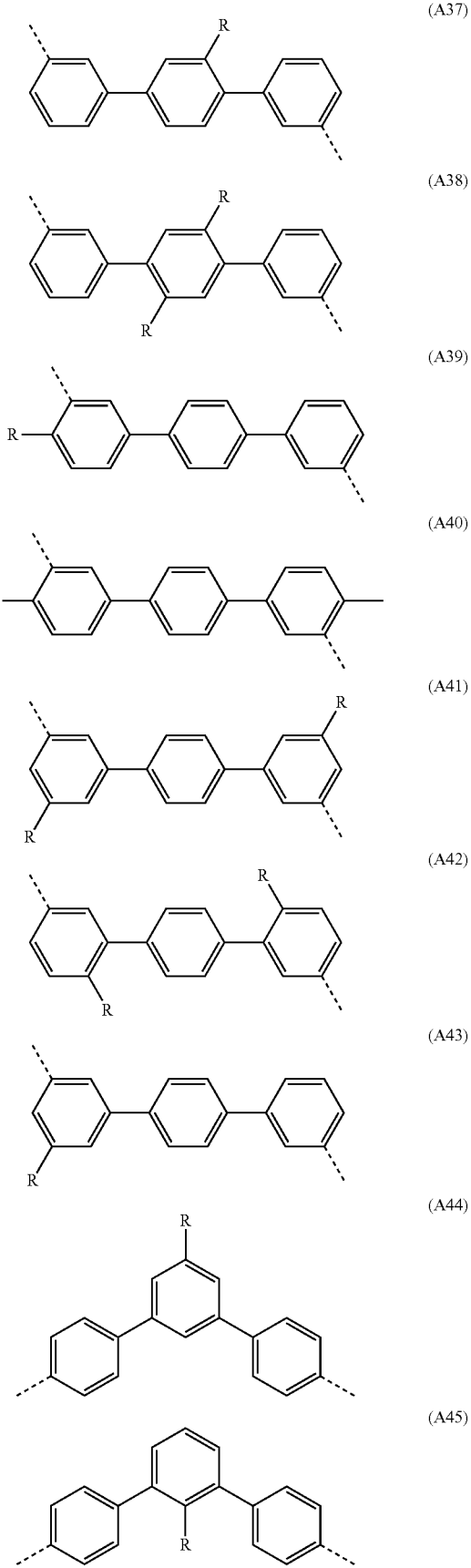

-continued
(A46)
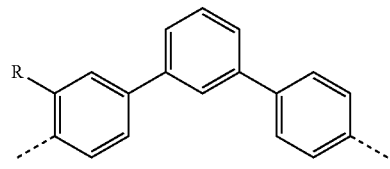
(A47)
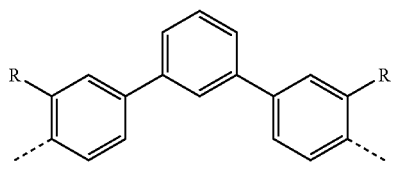
(A48)
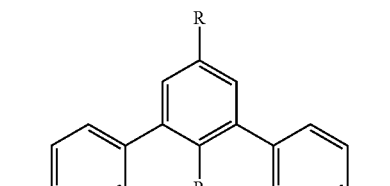
(A49)
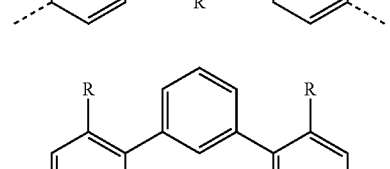
(A50)
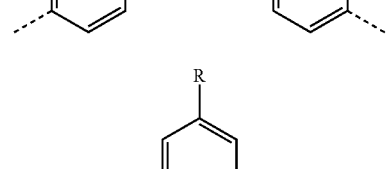
(A51)
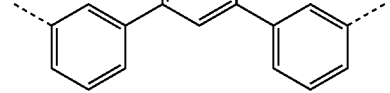
(A52)
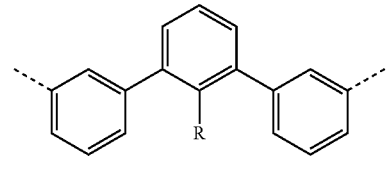
(A53)
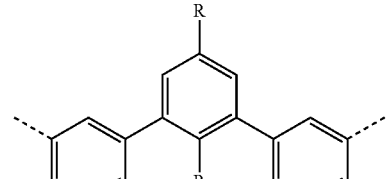
-continued
(A54)
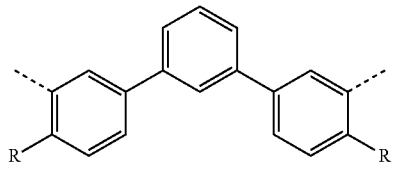
(A55)
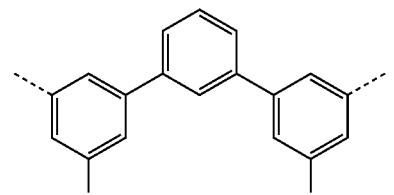
(A56)
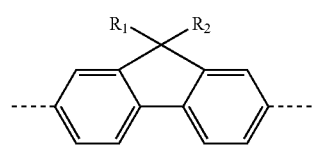
(A57)
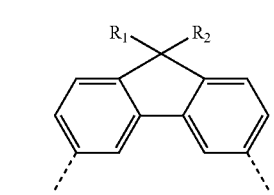
(A58)
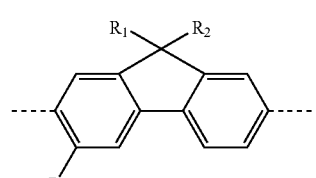
(A59)
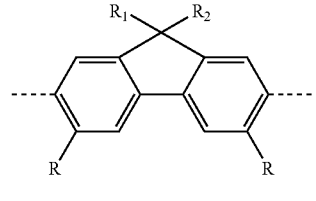
(A60)
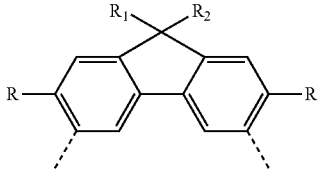
(A61)
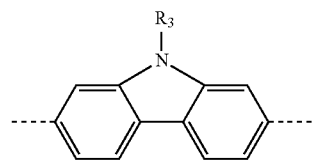

-continued (A62)

(A63)

(A64)

(A65)

(A66)

(A67)

(A68)

(A69)

wherein
R=H, R1, R2 or R3:
R1, R2 and R3 are same or independent selected from each other a linear, branched or cyclic alkyl group with 1 to 15 carbon atoms, an alkoxy group with 1 to 15 carbon atoms, an aryl group with 6 to 20 ring-forming carbon atoms, a heteroaryl group with 6 to 20 ring-forming atoms.

9. The OLED according to claim 1, wherein ET of chemical formula Ia, Ib and/or Ic is selected from the group of B1 to B32:

(B1)

(B2)

(B3)

(B4)

(B5)

(B6)

(B7)

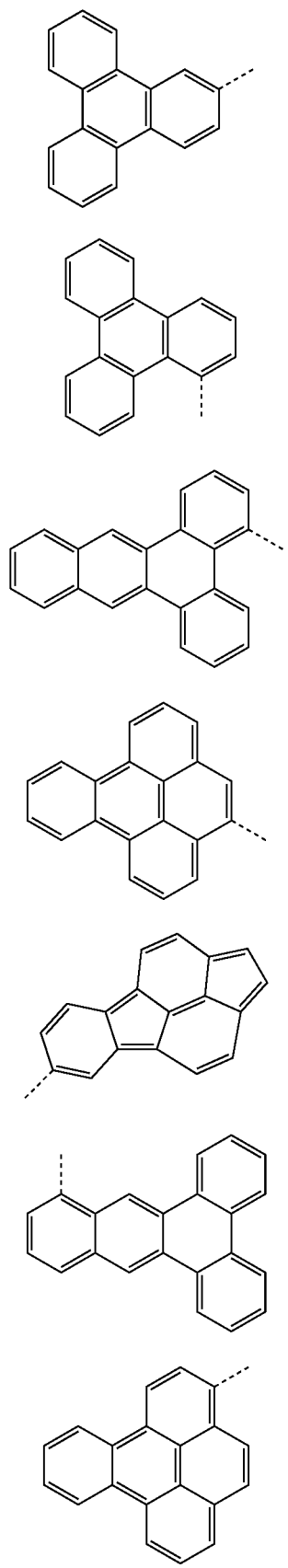
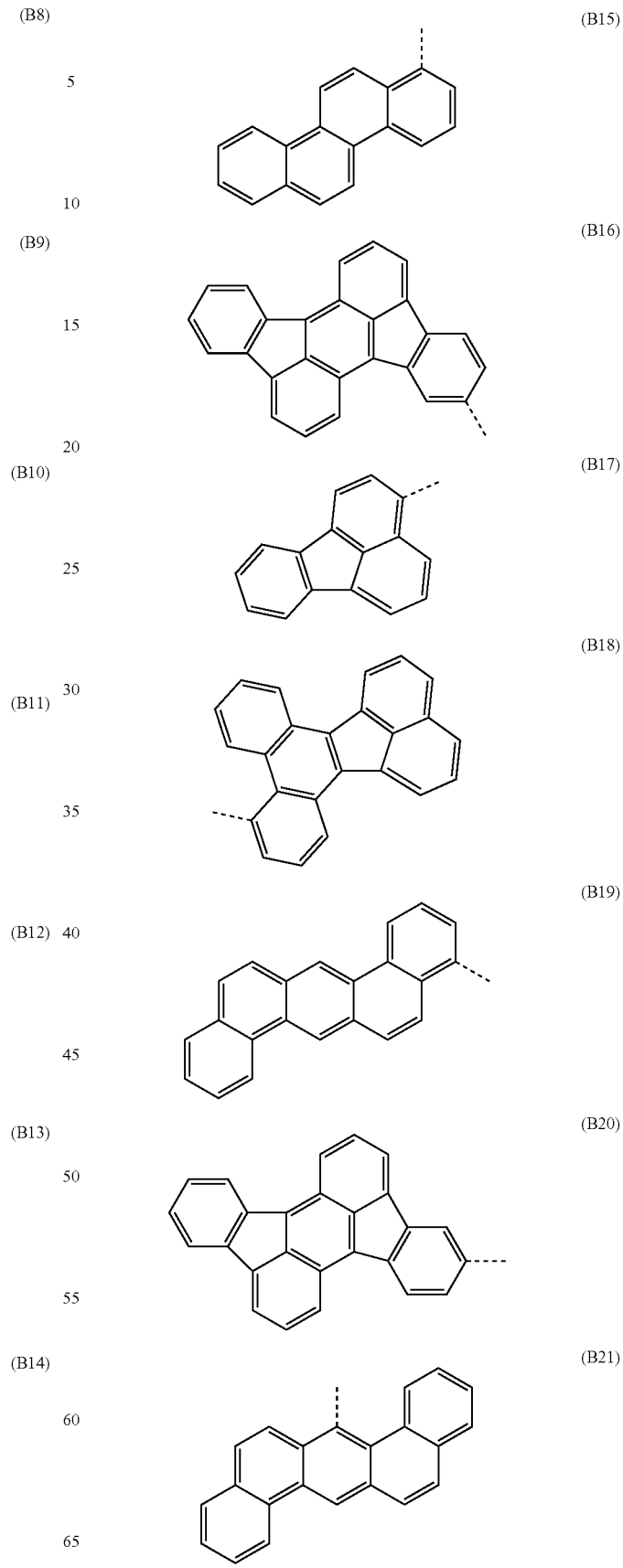

(B22) 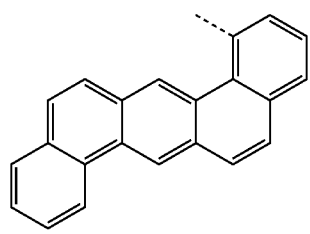

(B23) 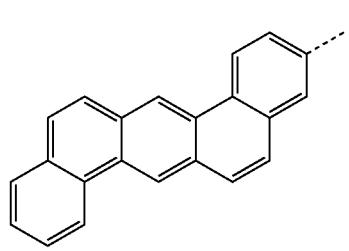

(B24) 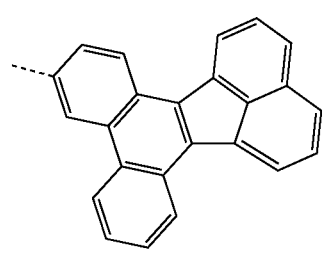

(B25) 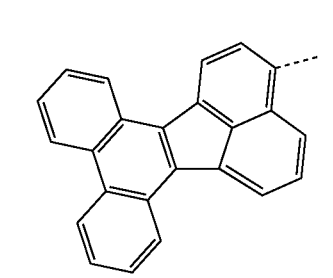

(B26) 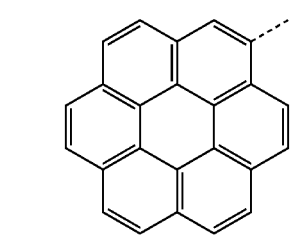

(B27) 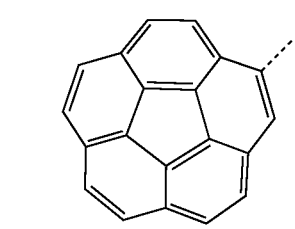

(B28) 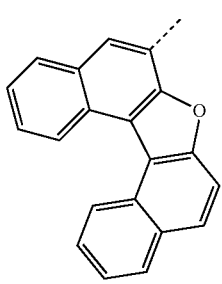

(B29) 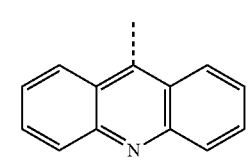

(B30) 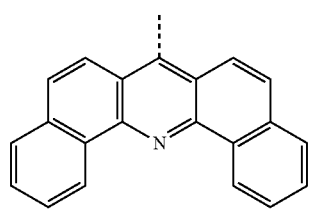

(B31) 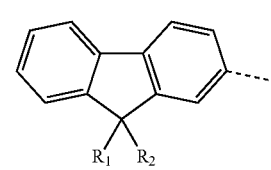

(B32) 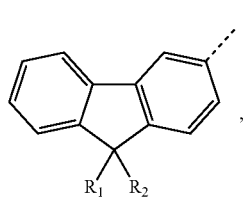

wherein

R1 and R2 are same or independent selected from each other a linear, branched or cyclic alkyl group with 1 to 15 carbon atoms, an alkoxy group with 1 to 15 carbon atoms, an aryl group with 6 to 20 ring-forming carbon atoms, a heteroaryl group with 6 to 20 ring-forming atoms.

10. The OED according to claim 1, wherein the second electron transport layer comprises at least one matrix material selected from the group of:

(MX 27)
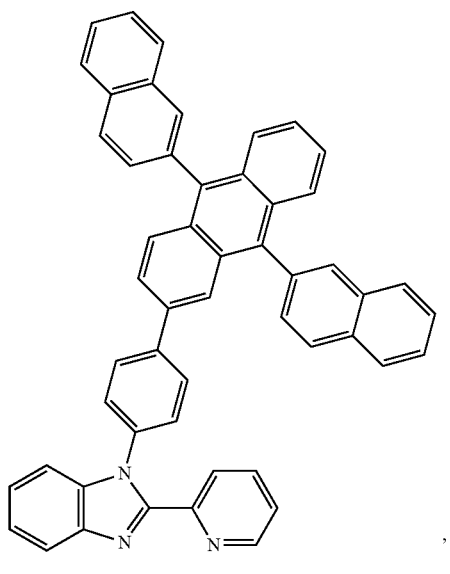
(MX 28)
(MX 29)
(MX 30)
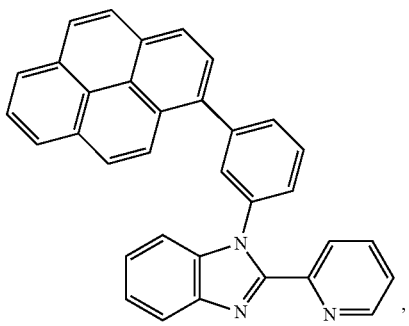
(MX 31)
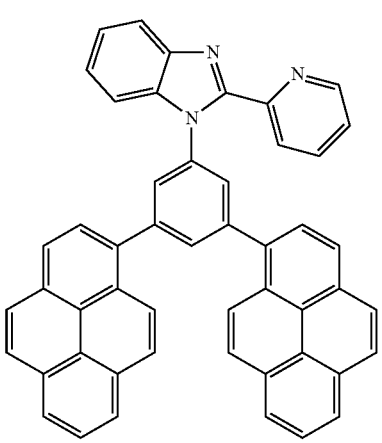
(MX 32)
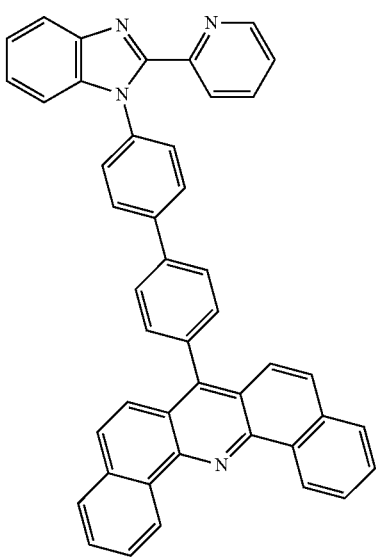

(MX 33)

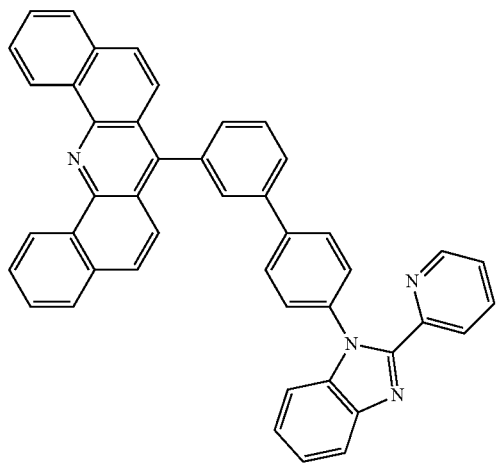

(MX 34)

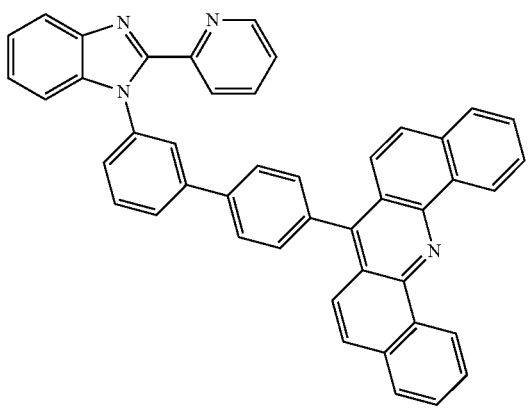

(MX 35)

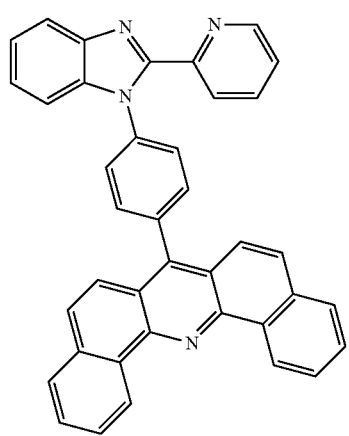

(MX 36)

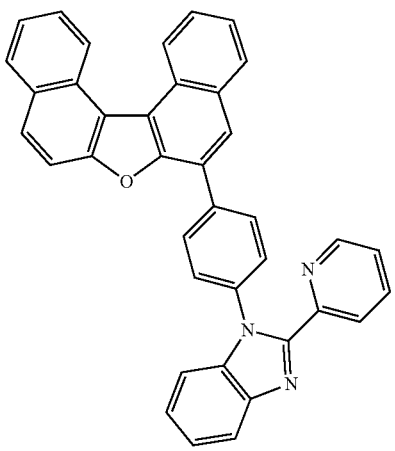

, and (MX 37)

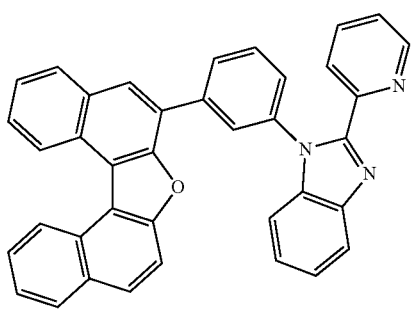

.

11. A method of manufacturing an organic light-emitting diode (OLED) according to claim 1, the method comprising:
providing at least three deposition sources, releasing the matrix compound or compounds of the first electron transport layer from a first deposition source, releasing the lithium halide and/or lithium organic complex from a second deposition source, and releasing the at least one matrix compound of the second electron transport layer from a third deposition source; and/or depositing (i) the matrix compound or compounds of the first electron transport layer, (ii) the lithium halide and/or lithium organic complex, and/or (iii) the at least one matrix compound of the second electron transport layer via vacuum thermal evaporation; and/or depositing (i) the matrix compound or compounds of the first electron transport layer, (ii) the lithium halide and/or lithium organic complex, and/or (iii) the at least one matrix compound of the second electron transport layer via solution processing.

12. A compound having the chemical formula Ia, Ib and/or Ic:

(Ia)

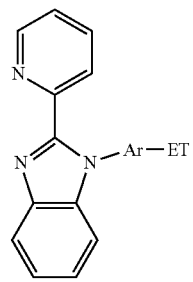

-continued

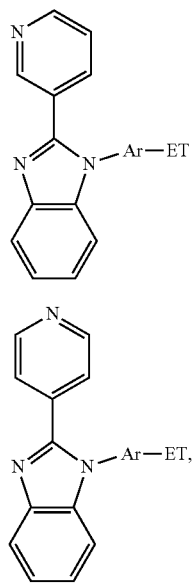

(Ib)

(Ic)

wherein
Ar=substituted or unsubstituted arylene with 6 to 20 ring-forming carbon atoms;
ET=a substituted or unsubstituted heteroaryl group with 14 to 24 ring-forming atoms.

13. The compound according to claim 12, wherein Ar is selected from a group comprising a m-phenylene, biphenyl-2,2'diyl, biphenyl-3,3'diyl, biphenyl 3,4' diyl, fluoren-3,6-diyl, p-terphenyl-3,3'-diyl, m-terphenyl-4,4'-diyl, m-terphenyl-3,3'-diyl, m-terphenyl-2,2'-diyl, o-terphenyl-4,4'-diyl, o-terphenyl-3,3'-diyl, o-terphenyl-2,2'-diyl; or naphthalen-2,6-diyl.

14. The compound according to claim 12, wherein ET is selected from the group of acridine or acridine compounds substituted with aryl or heteroaryl groups.

15. The compound according to claim 12, wherein the compound is selected from the matrix materials of

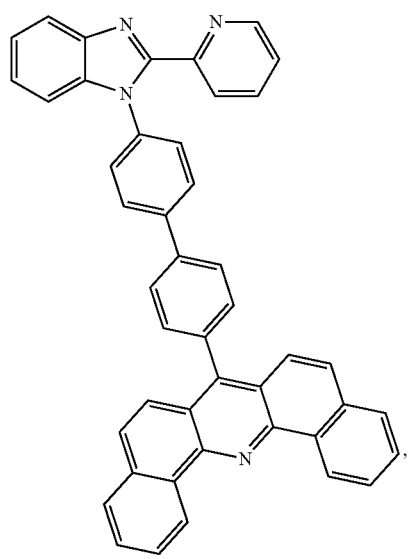

(MX 32)

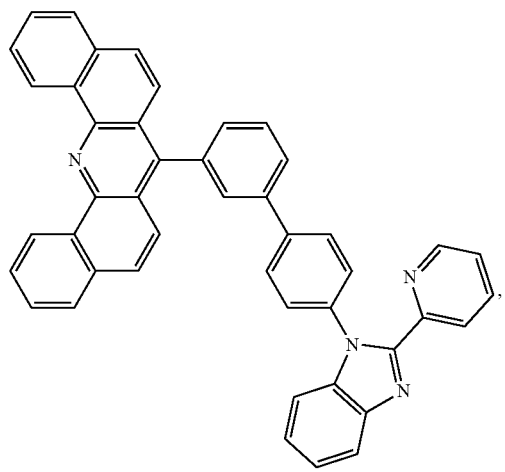

(MX 33)

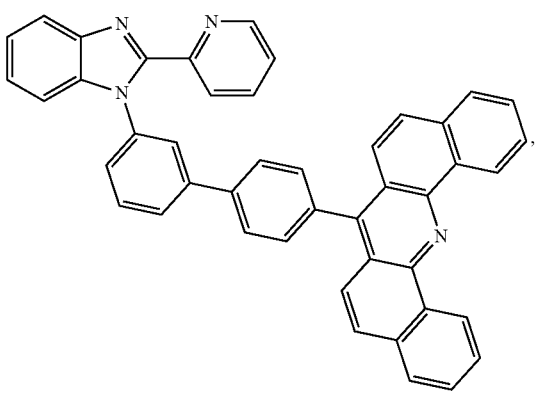

(MX 34)

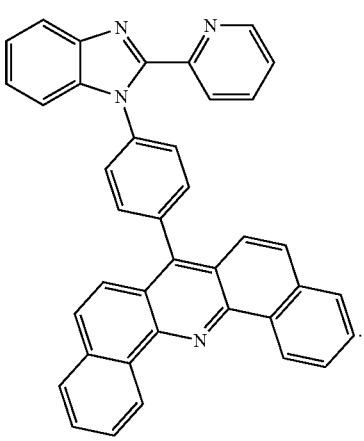

(MX 35)

16. An organic semiconductor layer, a charge transport layer, or a charge injection layer comprising a compound of formula Ia, Ib and/or Ic according to claim 12 as a matrix compound.

17. The MED according to claim 1, wherein
the second electron transport layer comprises at least one matrix material selected from the group of:

(MX 27)
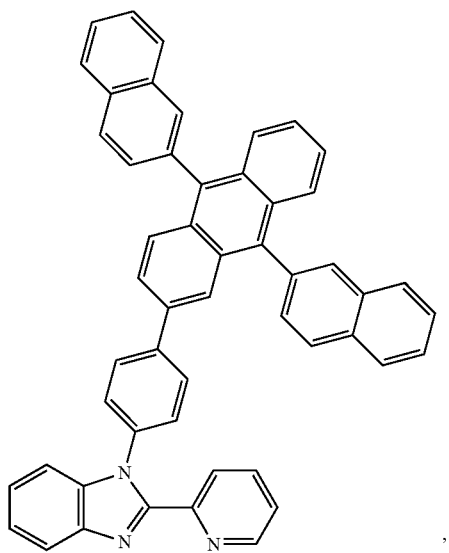
(MX 28)
(MX 29)
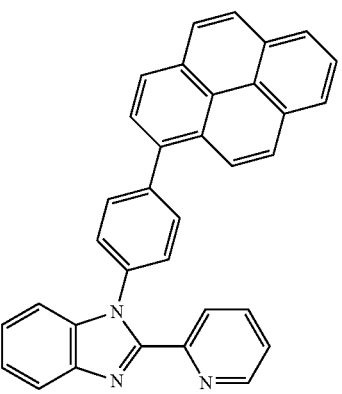
(MX 30)
* * * * *

UNITED STATES PATENT AND TRADEMARK OFFICE
CERTIFICATE OF CORRECTION

PATENT NO. : 11,081,652 B2  
APPLICATION NO. : 15/572336  
DATED : August 3, 2021  
INVENTOR(S) : Ulrich Denker et al.

Page 1 of 1

It is certified that error appears in the above-identified patent and that said Letters Patent is hereby corrected as shown below:

In the Claims

Column 142, Line 57, Claim 3, and Column 144, Line 1, Claim 7 and Line 26, Claim 8, each occurrence of the "OILED" according to claim 1, should read --OLED--.

Column 156, Line 65, Claim 10, the "OED" according to claim 1, should read --OLED--.

Column 162, Line 65, Claim 17, the "MED" according to claim 1, should read --OLED--.

Signed and Sealed this  
Twenty-first Day of December, 2021

Drew Hirshfeld  
*Performing the Functions and Duties of the*  
*Under Secretary of Commerce for Intellectual Property and*  
*Director of the United States Patent and Trademark Office*